US009522185B2

(12) United States Patent
Croll et al.

(10) Patent No.: US 9,522,185 B2
(45) Date of Patent: Dec. 20, 2016

(54) HUMAN ANTIBODIES TO GFR α3 AND METHODS OF TREATING PAIN ASSOCIATED WITH OSTEOARTHRITIS OR BONE CANCER

(71) Applicant: Regeneron Pharmaceuticals, Inc., Tarrytown, NY (US)

(72) Inventors: Susan D. Croll, Pleasantville, NY (US); Lynn Macdonald, White Plains, NY (US); Andrew J. Murphy, Croton-on-Hudson, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 14/577,362

(22) Filed: Dec. 19, 2014

(65) Prior Publication Data

US 2015/0110801 A1 Apr. 23, 2015

Related U.S. Application Data

(62) Division of application No. 13/971,965, filed on Aug. 21, 2013, now Pat. No. 8,968,736.

(60) Provisional application No. 61/692,029, filed on Aug. 22, 2012.

(51) Int. Cl.
| | |
|---|---|
| G01N 33/53 | (2006.01) |
| A61K 39/395 | (2006.01) |
| A61K 45/06 | (2006.01) |
| C07K 16/28 | (2006.01) |
| A61K 39/00 | (2006.01) |

(52) U.S. Cl.
CPC ........... *A61K 39/3955* (2013.01); *A61K 45/06* (2013.01); *C07K 16/28* (2013.01); *C07K 16/2863* (2013.01); *A61K 2039/505* (2013.01); *C07K 2317/21* (2013.01); *C07K 2317/31* (2013.01); *C07K 2317/33* (2013.01); *C07K 2317/565* (2013.01); *C07K 2317/76* (2013.01); *C07K 2317/92* (2013.01)

(58) Field of Classification Search
CPC . C07K 16/00; C07K 2317/24; C07K 2319/30; C07K 2317/31; C07K 2317/622; C07K 14/475; C07K 16/2875; C07K 16/46; C07K 14/48; C07K 16/18; C07K 16/2803; C07K 16/468; C07K 16/2863; C07K 2317/565; C07K 2317/76; A61K 2039/505; A61K 2039/507; A61K 2207/15; A61K 2267/0318; G01N 33/53; G01N 33/5058; C12N 15/1136
See application file for complete search history.

(56) References Cited

U.S. PATENT DOCUMENTS

| | | | |
|---|---|---|---|
| 6,677,135 B1 | 1/2004 | Sanicola-Nadel et al. | |
| 6,861,509 B1 * | 3/2005 | Sanicola-Nadel | C07K 14/71 530/300 |
| 6,927,044 B2 | 8/2005 | Stahl et al. | |
| 7,026,138 B1 | 4/2006 | de Sauvage et al. | |
| 7,138,251 B1 | 11/2006 | Fox et al. | |
| 7,691,973 B2 | 4/2010 | de Sauvage et al. | |
| 8,062,640 B2 | 11/2011 | Sleeman et al. | |
| 2004/0101920 A1 | 5/2004 | Radziejewski et al. | |
| 2006/0216289 A1 | 9/2006 | de Sauvage et al. | |
| 2007/0081992 A1 | 4/2007 | Pardridge et al. | |
| 2007/0232535 A1 | 10/2007 | de Sauvage et al. | |
| 2010/0166768 A1 | 7/2010 | Sleeman et al. | |
| 2010/0331527 A1 | 12/2010 | Davis et al. | |
| 2011/0195454 A1 | 8/2011 | McWhirter et al. | |

FOREIGN PATENT DOCUMENTS

| | | |
|---|---|---|
| WO | 2005103081 A2 | 11/2005 |
| WO | 2006138721 A1 | 12/2006 |
| WO | 2007146968 A2 | 12/2007 |
| WO | 2010077854 A1 | 7/2010 |

OTHER PUBLICATIONS

Anger. Neurotoxicology 1991. 12: 403-13.*
Tayebati. Mech. Ageing Dev. 2006. 127: 100-8.*
Wang et al. Adv. Drug Delivery Rev. 2003. 55:949-965.*
White et al. Nat Rev. Drug discovery. 2005. 4: 834-844.*
Pawson et al. 2003, Science 300:445-452.*
Marchand et al. Nat. Rev. Neurosci. 2005. 6: 521-532.*
Wang et al., (2006) "Structure of Artemin Complexed with its Receptor GFRalpha3: Convergent Recognition of Glial Cell Line-Derived Neurotrophic Factors," Structure, 14(6):1083-1092.
Wu et al., (1987) "Receptor-Mediated in Vitro Gene Transformation by a Soluble DNA Carrier System," J. Biol. Chem., 262(10):4429-4432.
Yan et al., (1995) "In Vivo Neurotrophic Effects of GDNF on Neonatal and Adult Facial Motor Neurons," Nature, 373:341-344.
Airaksinen et al., (1999) "GDNF Family Neurotrophic Factor Signaling: Four Masters, One Servant?," Mol. Cell. Neurosci., 13(5):313-325.
Airaksinen and Saarma, (2002) "The GDNF Family Signaling, Biological Functions and Therapeutic Value," Nat. Rev. Neurosci., 3(5):383-394.
Airaksinen et al., (2006) "Evolution of the GDNF Family Ligands and Receptors," Brain Behav. Evol., 68(3):181-190.
Al-Lazikani et al., (1997) "Standard Conformations for the Canonical Structures of Immunoglobulins," J. Mol. Biol., 273(4):927-948.
Altschul et al., (1990) "Basic Local Alignment Search Tool," J. Mol. Biol., 215(3):403-410.

(Continued)

*Primary Examiner* — Chang-Yu Wang
(74) *Attorney, Agent, or Firm* — Brownstein Hyatt Farber Schreck, LLP; Anna D. DiGabriele Petti; Cara L. Crowley-Weber

(57) ABSTRACT

The present invention provides antibodies that bind to human GFRα3 and methods of using same. According to certain embodiments of the invention, the antibodies are fully human antibodies that bind to human GFRα3. The antibodies of the invention are useful for the treatment of diseases and disorders associated with one or more GFRα3 biological activities, including the treatment of acute or chronic pain conditions, or inflammatory conditions.

9 Claims, 9 Drawing Sheets

(56) References Cited

OTHER PUBLICATIONS

Altschul et al., (1997) "Gapped BLAST and PSI-BLAST: a New Generation of Protein Database Search Programs," Nucleic Acids Res., 25:3389-3402.
Baloh et al., (1997) "TmR2. a Novel receptor that Mediates Neurturin and GDNF Signaling through Ret," Neuron 18, (5):793-802.
Banerjee et al., (2011) "ARTEMIN Synergizes with TWIST1 to Promote Metastasis and Poor Survival Outcome in Patients with ER Negative Mammary Carcinoma," Breast Cancer Res., 13(6):R112.
Buj-Bello et al., (1995) "GDNF is an Age-Specific Survival Factor for Sensory and Autonomic Neurons," Neuron 15, (4):821-828.
Buj-Bello et al., (1997) "Neurturin Responsiveness Requires a GPI-Linked Receptor and the Ret Receptor Tyrosine Kinase," Nature, 387(6634):721-724.
Ceyhan et al., (2006) "The Neurotrophic Factor Artemin Promotoes Pancreatic Cancer Invasion," Ann. Surg., 244(2):274-281.
Ceyhan et al., (2007) "The Neurotrophic Factor Artemin Influences the Extent of Neural Damage and Growth in Chronic Pancreatitis," Gut, 56(4):534-544.
Ehring, (1999) "Hydrogen Exchange/Electrospray Ionization Mass Spectrometry Studies of Structural Features of Proteins and Protein/protein Interactions," Anal. Biochem., 267(2):252-259.
Elitt et al., (2006) "Artemin Overexpression in Skin Enhances Expression of TRPV1 and TRPA 1 in Cutaneous Sensory Neurons and Leads to Behavioral Sensitivity to Heat and Cold," J. Neurosci., 26(33):8578-8587.
Engen et al., (2001) "Investigating Protein Structure and Dynamics by Hydrogen Exchange MS," Anal. Chern., 73(9):256A-265A.
Gonnet et al., (1992) "Exhaustive Matching of the Entire Protein Sequence Database," Science, 256(5062):1443-1445.
Henderson et al., (1994) "GDNF: a Potent Survival Factor of Motoneurons Present in Peripheral Nerve and Muscle," Science, 268(5187):1062-1064.
International Search Report and Written Opinion with respect to PCT/US2013/055921, mailed Oct. 29, 2013.
Junghans et al., (1990) "Anti-Tac-H, a Humanized Antibody to the Interleukin 2 Receptor with New Features for Immunotherapy in Malignant and Immune Disorders," Cancer Res., 50(5):1495-1502.
Kang et al., (2009) "Artemin is Oncogenic for Human Mammary Carcinoma Cells," Oncogene, 28(19):2034-2045.
Kang et al., (2010) "Artemin is Estrogen Regulated and Mediates Antiestrogen Resistance in Mammary Carcinoma," Oncogene, 29(22):3228-3240.
Klein et al., (1997) "A GPI-Linked Protein that Interacts with Reet to Form a Candidate Neurturin Receptor," Nature, 387(6634):717-721.
Kotzbauer et al., (1996) "Neurturin, a Relative of Glial-Cell-Line-Derived Neurotrophic Factor," Nature, 384(6608):467-470.
Kufer et al., (2004) "A Revival of Bispecific Antibodies," Trends Biotechnol., 22(5):238-244.
Langer, (1990) "New Methods of Drug Delivery," Science, 249(4976):1527-1533.
Li et al., (2011) "miR-223 Regulates Migration and Invasion by Targeting Artemin in Human Esophageal Carcinoma," J. Biomed. Sci., 18:24.
Lindsay et al., (1996) "GDNF in a Bind with Known Orphan: Accessory Implicated in a New Twist," Neuron 17, (4):571-574.
Malin et al., (2006) "Glial Cell Line-Derived Neurotrophic Factor Family Members Sensitize Nociceptors in Vitro and Produce Thermal Hyperalgesia in Vivo," J. Neurosci., 26(33):8588-8599.
Martin et al., (1989) "Modeling Antibody Hypervariable Loops: a Combined Algorithm," Proc. Natl. Acad. Sci., USA, 86(23):9268-9272.
Masure et al., (1998) "Molecular Cloning, Expression and Tissue Distribution of Glial-Cell-Line-Derived Neurotrophic Factor Family Receptor alpha-3 (GFRalpha-3)," Eur. J. Biochem., 251(3):622-630.
Nomoto et al., (1998) "Molecular Cloning and Expression Analysis of GFR alpha-3, a Novel cDNA Related to GDNFR alpha and NTNR alpha," Biochem. Biophys. Res. Commun., 244(3):849-853.
Orozco et al., (2001) "GFRalph3 is Expressed Predominantly in Nociceptive Sensor Neurons," Eur. J. Neurosci., 13(11),2177-2182.
Padlan et al., (1995) "Identification of Specificity-Determining Residues in Antibodies," FASEB, 9(1):133-139.
Pandey et al., (2010) "Artemin Stimulates Oncogenicity and Invasiveness of Humen Endometrial Carcinoma Cells," Endocrinology, 151(3) 909-920.
Pearson, (1994) "Using the FASTA Program to Search Protein and DNA Sequence Databases," Methods Mol. Biol., 24:307-331.
Powell et al., (1998) "Compendium of Excipients for Parenterai Formulations," PDA J. Pharm. Sci. Technol., 52(5):238-311.
R&D Systems, (Jun. 7, 2005) "Anti-mouse GFRalpha3 Antibody," Internet citation, www.mdysystems.com/pdf/AF2645.
Reddy et al., (2000) "Elimination of Fc Receptor-Dependent Effector Functions of a Modified IgG4 Monoclonai Antibody to Human CD4," J. Immunol., 164(4):1925-1933.
Reineke, (2004) "Antibody Epitope Mapping Using Arrays of Synthetic Peptides," Methods Mol. Biol., 248:443-463.
Rudikoff et al., (1982) "Single Amino Acid Substitution Altering Antigen-Binding Specificity," Proc. Natl. Acad. Sci., USA, 79:1979-1983.
Sanicola et al., (1997) "Glial Cell Line-Derived Neurotrophic Factor-Dependent RET Activation can be Mediated by Two Different Cell-Surface Accessory Proteins," Proc. Natl. Acad. Sci., USA, 94(12):6238-6243.
Schaar et al., (1993) "Regional and Cell-Specific Expression of GDNF in Rat Brain," Exp. Neurol., 124(2):368-371.
Shields et al., (2002) "Lack of Fucose on Human IgG1 N-Linked Oligosaccharide Improves Binding to Human FCgamma RIII and Antibody-Dependent Cellular Toxicity," J. Biol. Chem., 277(30):26733-26740.
Springer et al., (1994) "Expression of GDNF mRNA in Rat and Human Nervous Tissue," Exp. Neurol., 127(2):167-170.
Tanaka et al., (2011) "Modulation of Visceral Hypersensitivity by Glial Cell Line-Derived Neurotrophic Factor Family Receptor alpha-3 in Colorectal Afferents," Am. J. Physiol. Gastrointest. Liver Physiol., 300(3):G418-G424.
Tang et al., (2010) "Artemin-Stimulated Progression of Human Non-Small Cell Lung Carcinoma is Mediated by BCL2," Mol. Cancer Ther., 9(6):1697-1708.
Tomer et al., (2000) "Characterization of a Discontinuous Epitope of the Human Immunodeficiency Virus (HIV) Core Protein p24 by Epitope Excision and Differential Chemical Modification Followed by Mass Spectrometric Peptide Mapping Analysis," Protein Sci., 9(3):487-496.
Trupp et al., (1995) "Peripheral Expression and Biological Activities of GDNF, a New Neurotrophic Factor for Avian and Mammalian Peripheral Neurons," J. Cell Biol., 130(1):137-148.
Tutt et al., (1991) "Trispecific F(ab')3 Derivatives that Use Cooperative Signaling via the TCR/CD3 Complex and CD2 to Activate and Redirect Resting Cytotoxic T cells," J. Immunol., 147(1):60-69.
Vajdos et al., (2002) "Comprehensive Functional Maps of the Antigen-Binding Site of an Anti-ErbB2 Antibody Obtained with Shotgun Scanning Mutagenesis," J. Mol. Biol., 320(2):415-428.
Deberry et al. (2015) "Artemin Immunotherapy is Effective in Preventing and Reversing Cystitis-Induced Bladder Hyperalgesia via TRPA1 Regulation," The Journal of Pain, 16(7):628-636.
Lippoldt et al. (2016) "Inflammatory and neuropathic cold allodynia are selectively mediated by the neurotrophic factor receptor GFRα3," PNAS Early Edition, www.pnas.org/cgi/doi/10.1073/pnas.1603294113, pp. 1-6.
Thornton (2013) "Artemin-GFRalpha3 interactions partially contribute to acute inflammatory hypersensitivity," Neuroscience Letters 545:23-28.

* cited by examiner

Figure 9

| Antibody | Biotin-human GFRα3 captured (nm) | Amount of Antibody 1 bound (nm) | H4H2236N3 | H4H2342P | H4H2295S | H4H2294S | H4H2291S | H4H2357S | H4H2355S | H4H2296S | H4H2243N2 | H4H2212N | H4H2352S | H4H2292S | H4H2350P |
|---|---|---|---|---|---|---|---|---|---|---|---|---|---|---|---|
| H4H2236N3 | 1.07 ± 0.08 | 2.64 ± 0.18 | 0.00 | -0.01 | 0.03 | 0.00 | 0.06 | 0.04 | 0.00 | 0.02 | 0.02 | 1.79 | 1.91 | 1.81 | 1.35 |
| H4H2342P | 1.09 ± 0.08 | 2.69 ± 0.17 | 0.20 | 0.06 | 0.31 | 0.23 | 0.45 | 0.25 | 0.16 | 0.28 | 0.11 | 1.76 | 1.72 | 1.85 | 1.46 |
| H4H2295S | 1.14 ± 0.15 | 2.83 ± 0.27 | 0.01 | 0.01 | 0.05 | 0.02 | 0.20 | 0.05 | 0.02 | 0.07 | 0.01 | 1.81 | 1.85 | 1.80 | 1.35 |
| H4H2294S | 1.22 ± 0.04 | 2.91 ± 0.09 | 0.05 | 0.01 | 0.04 | 0.02 | 0.12 | 0.03 | 0.00 | 0.04 | 0.03 | 1.92 | 1.99 | 1.92 | 1.42 |
| H4H2291S | 1.16 ± 0.04 | 2.89 ± 0.08 | 0.01 | -0.01 | 0.00 | 0.00 | 0.05 | 0.00 | 0.00 | -0.01 | 0.00 | 1.96 | 2.03 | 1.94 | 1.44 |
| H4H2357S | 1.15 ± 0.03 | 2.82 ± 0.07 | 0.04 | -0.01 | 0.12 | 0.00 | 0.18 | 0.04 | 0.00 | 0.06 | 0.01 | 1.90 | 2.00 | 1.92 | 1.35 |
| H4H2355S | 1.15 ± 0.03 | 2.73 ± 0.07 | 0.18 | 0.06 | 0.20 | 0.05 | 0.31 | 0.16 | 0.07 | 0.18 | 0.09 | 1.95 | 1.97 | 1.92 | 1.44 |
| H4H2296S | 1.29 ± 0.13 | 2.88 ± 0.23 | 0.07 | 0.03 | 0.05 | 0.04 | 0.18 | 0.06 | 0.02 | 0.07 | 0.06 | 1.76 | 2.01 | 1.87 | 1.27 |
| H4H2243N2 | 1.10 ± 0.08 | 2.42 ± 0.17 | 0.30 | 0.15 | 0.39 | 0.29 | 0.52 | 0.32 | 0.24 | 0.33 | 0.06 | 0.22 | 0.46 | 1.70 | 1.20 |
| H4H2212N | 1.09 ± 0.08 | 2.32 ± 0.15 | 2.14 | 2.17 | 2.15 | 2.12 | 2.69 | 2.38 | 2.05 | 2.36 | 0.16 | 0.05 | 0.08 | 1.76 | 1.36 |
| H4H2352S | 1.15 ± 0.03 | 2.74 ± 0.16 | 2.15 | 2.08 | 2.31 | 2.25 | 2.63 | 2.45 | 2.12 | 2.35 | 0.13 | 0.05 | 0.10 | 0.15 | 1.43 |
| H4H2292S | 1.17 ± 0.04 | 2.82 ± 0.08 | 2.24 | 2.16 | 2.31 | 2.31 | 2.81 | 2.43 | 2.07 | 2.36 | 1.91 | 1.78 | 0.34 | 0.11 | 1.53 |
| H4H2350P | 1.09 ± 0.07 | 3.31 ± 0.15 | 1.98 | 1.80 | 2.05 | 2.00 | 2.57 | 2.23 | 1.77 | 2.10 | 1.72 | 1.57 | 2.06 | 1.74 | 0.25 |

SEQUENCE LISTING

```
<160> NUMBER OF SEQ ID NOS: 411

<210> SEQ ID NO 1
<211> LENGTH: 360
<212> TYPE: DNA
<213> ORGANISM: Artificial Sequence
<220> FEATURE:
<223> OTHER INFORMATION: Synthetic

<400> SEQUENCE: 1
gaagtgcagc tggtggagtc tgggggaggc ttggtacagc ctggcaggtc cctgagactc      60
tcctgtgcag cctctggatt cacctttaat gattatgcca tgcactgggt ccggcaagct     120
ccagggaagg gcctggagtg ggtctcaggt attagttgga atagtggtaa cataggctat     180
gcggactctg tgaagggccg attcaccatc tccagagaca acgccaagaa ctccctgtat     240
ctacagatga acagtctgag agctgaggac acggccttgt atttctgtgc aagagatacc     300
cgtatggcaa ctcgtccctt tgactactgg ggccaggaa ccctggtcac cgtctcctca      360

<210> SEQ ID NO 2
<211> LENGTH: 120
<212> TYPE: PRT
<213> ORGANISM: Artificial Sequence
<220> FEATURE:
<223> OTHER INFORMATION: Synthetic

<400> SEQUENCE: 2
```

```
Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Asn Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Phe Cys
                85                  90                  95

Ala Arg Asp Thr Arg Met Ala Thr Arg Pro Phe Asp Tyr Trp Gly Gln
            100                 105                 110

Gly Thr Leu Val Thr Val Ser Ser
        115                 120

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggattcacct ttaatgatta tgcc                                          24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Asn Asp Tyr Ala
 1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
attagttgga atagtggtaa cata                                          24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Ser Trp Asn Ser Gly Asn Ile
 1               5

<210> SEQ ID NO 7
<211> LENGTH: 39
<212> TYPE: DNA
```

<213> ORGANISM: Artificial Sequence
<220> FEATURE:
<223> OTHER INFORMATION: Synthetic

<400> SEQUENCE: 7
gcaagagata cccgtatggc aactcgtccc tttgactac         39

<210> SEQ ID NO 8
<211> LENGTH: 13
<212> TYPE: PRT
<213> ORGANISM: Artificial Sequence
<220> FEATURE:
<223> OTHER INFORMATION: Synthetic

<400> SEQUENCE: 8

Ala Arg Asp Thr Arg Met Ala Thr Arg Pro Phe Asp Tyr
 1               5                  10

<210> SEQ ID NO 9
<211> LENGTH: 318
<212> TYPE: DNA
<213> ORGANISM: Artificial Sequence
<220> FEATURE:
<223> OTHER INFORMATION: Synthetic

<400> SEQUENCE: 9
gacatccaga tgacccagtc tccttccacc ctgtctgcat ctgtaggaga cagagtcacc      60
atcacttgcc gggccagtca gagtattagt aggtggttgg cctggtatca gcagaagcca     120
gggaaagccc ctaagctcct gatctataag gcgtctagtt tagaaagtgg ggtcccatca     180
aggttcagcg gcagtggatc tgggacagaa ttcactctca ccatcagcag cctgcagcct     240
gatgattttg caagttatta ctgccaacag tataatagtt attcaacttt tggccagggg     300
accaagctgg agatcaaa                                                  318

<210> SEQ ID NO 10
<211> LENGTH: 106
<212> TYPE: PRT
<213> ORGANISM: Artificial Sequence
<220> FEATURE:
<223> OTHER INFORMATION: Synthetic

<400> SEQUENCE: 10

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Arg Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Ser Tyr Tyr Cys Gln Gln Tyr Asn Ser Tyr Ser Thr
                85                  90                  95

Phe Gly Gln Gly Thr Lys Leu Glu Ile Lys
            100                 105

<210> SEQ ID NO 11
<211> LENGTH: 18
<212> TYPE: DNA
<213> ORGANISM: Artificial Sequence

```
<220> FEATURE:
<223> OTHER INFORMATION: Synthetic

<400> SEQUENCE: 11
cagagtatta gtaggtgg                                                      18

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Gln Ser Ile Ser Arg Trp
 1               5

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 aaggcgtct                                                                 9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Lys Ala Ser
 1

<210> SEQ ID NO 15
<211> LENGTH: 24
<212> TYPE: DNA
<213> ORGANISM: Artificial Sequence
<220> FEATURE:
<223> OTHER INFORMATION: Synthetic

<400> SEQUENCE: 15
caacagtata atagttattc aact                                               24

<210> SEQ ID NO 16
<211> LENGTH: 8
<212> TYPE: PRT
<213> ORGANISM: Artificial Sequence
<220> FEATURE:
<223> OTHER INFORMATION: Synthetic

<400> SEQUENCE: 16

Gln Gln Tyr Asn Ser Tyr Ser Thr
 1               5

<210> SEQ ID NO 17
<211> LENGTH: 360
<212> TYPE: DNA
<213> ORGANISM: Artificial Sequence
<220> FEATURE:
<223> OTHER INFORMATION: Synthetic

<400> SEQUENCE: 17
```

```
gaggtgcagc tgttggagtc tgggggaggc ttggtacagc ctggggggtc cctgagactc      60
tcctgtgcag cctctggatt cacctttagc agctatgcca tgagctgggt ccgccagggg     120
ccagggaagg gctggagtg gtctcaggt attagtggta gtggtggcag cacatacaac      180
gcagactccg tgaagggccg gttcaccatc tccagagaca attccaagaa cacgctgtat    240
ttgcaaatga acagcctgag agccgaggac acggccgtat attactgtgc gaaagattct    300
gggacctact ggtactactt tgactactgg ggccagggaa tcctggtcac cgtctcctca    360
```

<210> SEQ ID NO 18
<211> LENGTH: 120
<212> TYPE: PRT
<213> ORGANISM: Artificial Sequence
<220> FEATURE:
<223> OTHER INFORMATION: Synthetic

<400> SEQUENCE: 18

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Gly Pro Gly Lys Gly Leu Glu Trp Val
        35                  40                  45

Ser Gly Ile Ser Gly Ser Gly Ser Thr Tyr Asn Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gly Thr Tyr Trp Tyr Tyr Phe Asp Tyr Trp Gly Gln
            100                 105                 110

Gly Ile Leu Val Thr Val Ser Ser
        115                 120
```

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19

```
ggattcacct ttagcagcta tgcc                                              24
```

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

```
Gly Phe Thr Phe Ser Ser Tyr Ala
 1               5
```

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
attagtggta gtggtggcag caca                                         24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Ile Ser Gly Ser Gly Gly Ser Thr
1               5

<210> SEQ ID NO 23
<211> LENGTH: 39
<212> TYPE: DNA
<213> ORGANISM: Artificial Sequence
<220> FEATURE:
<223> OTHER INFORMATION: Synthetic

<400> SEQUENCE: 23
gcgaaagatt ctgggaccta ctggtactac tttgactac                         39

<210> SEQ ID NO 24
<211> LENGTH: 13
<212> TYPE: PRT
<213> ORGANISM: Artificial Sequence
<220> FEATURE:
<223> OTHER INFORMATION: Synthetic

<400> SEQUENCE: 24

Ala Lys Asp Ser Gly Thr Tyr Trp Tyr Tyr Phe Asp Tyr
1               5                   10

<210> SEQ ID NO 25
<211> LENGTH: 339
<212> TYPE: DNA
<213> ORGANISM: Artificial Sequence
<220> FEATURE:
<223> OTHER INFORMATION: Synthetic

<400> SEQUENCE: 25
gacatcgtga tgacccagtc tccagactcc ctggctgtgt ctctgggcga gagggccacc      60
atcaactgca gtccagcca gaatatttta tacagctccg acaataagaa ctacttagct      120
tggtaccaga gaaaccagg acagcctcct aagctgctca tttactgggc atctacccga      180
gaatccgggg tccctgaccg attcagtggc agcgggtctg ggacagattt cactctcacc      240
atcatcagcc tgcaggctga agatgtggca ttatattact gtcatcaata ttatactact      300
cctccgacgt tcggccaagg gaccaaagtg gaaatcaaa                           339

<210> SEQ ID NO 26
<211> LENGTH: 113
<212> TYPE: PRT
<213> ORGANISM: Artificial Sequence
<220> FEATURE:
<223> OTHER INFORMATION: Synthetic

<400> SEQUENCE: 26

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Ile Leu Tyr Ser

```
            20                  25                  30
Ser Asp Asn Lys Asn Tyr Leu Ala Trp Tyr Gln Lys Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ile Ser Leu Gln Ala Glu Asp Val Ala Leu Tyr Tyr Cys His Gln
                85                  90                  95

Tyr Tyr Thr Thr Pro Pro Thr Phe Gly Gln Gly Thr Lys Val Glu Ile
            100                 105                 110

Lys

<210> SEQ ID NO 27
<211> LENGTH: 36
<212> TYPE: DNA
<213> ORGANISM: Artificial Sequence
<220> FEATURE:
<223> OTHER INFORMATION: Synthetic

<400> SEQUENCE: 27
cagaatattt tatacagctc cgacaataag aactac                              36

<210> SEQ ID NO 28
<211> LENGTH: 12
<212> TYPE: PRT
<213> ORGANISM: Artificial Sequence
<220> FEATURE:
<223> OTHER INFORMATION: Synthetic

<400> SEQUENCE: 28

Gln Asn Ile Leu Tyr Ser Ser Asp Asn Lys Asn Tyr
1               5                   10

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 tgggcatct                                                            9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Trp Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
```

```
catcaatatt atactactcc tccgacg                                          27
```

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

His Gln Tyr Tyr Thr Thr Pro Pro Thr
 1               5

<210> SEQ ID NO 33
<211> LENGTH: 369
<212> TYPE: DNA
<213> ORGANISM: Artificial Sequence
<220> FEATURE:
<223> OTHER INFORMATION: Synthetic

<400> SEQUENCE: 33

```
gaggtgcagt tattggagtc tgggggggaac ttggtacagc cggggggggtc cctgagactc    60
tcctgtgcag cctctggatt caccttttagc agttatgcca tgacctgggt ccgccaggct   120
ccagggaagg ggctggagtg ggtctcaact attagtggta gtggtaccag cacatattac   180
gcagactccg tgaagggccg gttcaccatc tccaggaca attccaggga cacggtgttt   240
ctacaaatga acagcctgag agccgaggac acggccgtat attactgttc gaaaccttct   300
gcattacgat tttttacattg gttagctatg gacgtctggg gccaagggac cctggtcacc   360
gtctcctca                                                            369
```

<210> SEQ ID NO 34
<211> LENGTH: 123
<212> TYPE: PRT
<213> ORGANISM: Artificial Sequence
<220> FEATURE:
<223> OTHER INFORMATION: Synthetic

<400> SEQUENCE: 34

Glu Val Gln Leu Leu Glu Ser Gly Gly Asn Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Thr Ile Ser Gly Ser Gly Thr Ser Thr Tyr Tyr Ala Asp Ser Val
    50                  55                  60

Lys Gly Arg Phe Thr Ile Ser Arg Asp Asn Ser Arg Asp Thr Val Phe
65                  70                  75                  80

Leu Gln Met Asn Ser Leu Arg Ala Glu Asp Thr Ala Val Tyr Tyr Cys
                85                  90                  95

Ser Lys Pro Ser Ala Leu Arg Phe Leu His Trp Leu Ala Met Asp Val
            100                 105                 110

Trp Gly Gln Gly Thr Leu Val Thr Val Ser Ser
        115                 120

<210> SEQ ID NO 35
<211> LENGTH: 24
<212> TYPE: DNA
<213> ORGANISM: Artificial Sequence
<220> FEATURE:

<223> OTHER INFORMATION: Synthetic

<400> SEQUENCE: 35
ggattcacct ttagcagtta tgcc                                          24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Phe Thr Phe Ser Ser Tyr Ala
1               5

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
attagtggta gtggtaccag caca                                          24

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

Ile Ser Gly Ser Gly Thr Ser Thr
1               5

<210> SEQ ID NO 39
<211> LENGTH: 48
<212> TYPE: DNA
<213> ORGANISM: Artificial Sequence
<220> FEATURE:
<223> OTHER INFORMATION: Synthetic

<400> SEQUENCE: 39
tcgaaacctt ctgcattacg atttttacat tggttagcta tggacgtc                48

<210> SEQ ID NO 40
<211> LENGTH: 16
<212> TYPE: PRT
<213> ORGANISM: Artificial Sequence
<220> FEATURE:
<223> OTHER INFORMATION: Synthetic

<400> SEQUENCE: 40

Ser Lys Pro Ser Ala Leu Arg Phe Leu His Trp Leu Ala Met Asp Val
1               5                   10                  15

<210> SEQ ID NO 41
<211> LENGTH: 321
<212> TYPE: DNA
<213> ORGANISM: Artificial Sequence
<220> FEATURE:
<223> OTHER INFORMATION: Synthetic

<400> SEQUENCE: 41

-continued

```
gacatccaga tgacccagtc tccatcctca ctgtctgcat ttgtaggaga cagagtcacc    60
atcacttgtc gggcgagtca ggacattagg aattatttag actggtttca gcagaaacca   120
gggaaagccc ctaagtccct gatctatgct gcatccaatt tgcaaagtgg ggtcccatca   180
aggttcggcg gcagtggatc tgggacagat ttcactctca ccatcaacag cctgcagcct   240
gaagattttg taacttatta ctgccagcag tataattctt accctcccac tttcggcgga   300
gggaccaagg tggagatcaa a                                             321
```

<210> SEQ ID NO 42
<211> LENGTH: 107
<212> TYPE: PRT
<213> ORGANISM: Artificial Sequence
<220> FEATURE:
<223> OTHER INFORMATION: Synthetic

<400> SEQUENCE: 42

```
Asp Ile Gln Met Thr Gln Ser Pro Ser Ser Leu Ser Ala Phe Val Gly
 1               5                   10                  15

Asp Arg Val Thr Ile Thr Cys Arg Ala Ser Gln Asp Ile Arg Asn Tyr
            20                  25                  30

Leu Asp Trp Phe Gln Gln Lys Pro Gly Lys Ala Pro Lys Ser Leu Ile
        35                  40                  45

Tyr Ala Ala Ser Asn Leu Gln Ser Gly Val Pro Ser Arg Phe Gly Gly
    50                  55                  60

Ser Gly Ser Gly Thr Asp Phe Thr Leu Thr Ile Asn Ser Leu Gln Pro
65                  70                  75                  80

Glu Asp Phe Val Thr Tyr Tyr Cys Gln Gln Tyr Asn Ser Tyr Pro Pro
                85                  90                  95

Thr Phe Gly Gly Gly Thr Lys Val Glu Ile Lys
            100                 105
```

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43

```
caggacatta ggaattat                                                  18
```

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

```
Gln Asp Ile Arg Asn Tyr
 1               5
```

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45

```
gctgcatcc                                                             9
```

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Ala Ala Ser
 1

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
cagcagtata attcttaccc tcccact                                          27

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Gln Gln Tyr Asn Ser Tyr Pro Pro Thr
 1               5

<210> SEQ ID NO 49
<211> LENGTH: 372
<212> TYPE: DNA
<213> ORGANISM: Artificial Sequence
<220> FEATURE:
<223> OTHER INFORMATION: Synthetic

<400> SEQUENCE: 49
caggttcaac tggtgcagtc tggagctgag gtgaagaagc ctggggcctc agtgaaggtc      60
tcctgcaagg cttctggtta cacctttacc agctatggta tcatctgggt gcgacaggcc     120
cctggacaag gcttgagtg gatgggatgg atcagcggtt acaatggtaa cacaaactat      180
gcacagaatc tccagggcag agtcaccatg accacagaca cttccacgac cacagcctac     240
atggagctga ggagcctgag atctgacgac acggccgtgt attactgtgc gagatggggt     300
atagcaactc gtccctacta ctactacggt atggacgtct ggggccaagg gaccacggtc     360
accgtctcct ca                                                         372

<210> SEQ ID NO 50
<211> LENGTH: 124
<212> TYPE: PRT
<213> ORGANISM: Artificial Sequence
<220> FEATURE:
<223> OTHER INFORMATION: Synthetic

<400> SEQUENCE: 50

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Gly Ile Ile Trp Val Arg Gln Ala Pro Gly Gln Gly Leu Glu Trp Met
            35                  40                  45

Gly Trp Ile Ser Gly Tyr Asn Gly Asn Thr Asn Tyr Ala Gln Asn Leu
 50                  55                  60

Gln Gly Arg Val Thr Met Thr Thr Asp Thr Ser Thr Thr Thr Ala Tyr
 65                  70                  75                  80

Met Glu Leu Arg Ser Leu Arg Ser Asp Asp Thr Ala Val Tyr Tyr Cys
                 85                  90                  95

Ala Arg Trp Gly Ile Ala Thr Arg Pro Tyr Tyr Tyr Gly Met Asp
             100                 105                 110

Val Trp Gly Gln Gly Thr Thr Val Thr Val Ser Ser
        115                 120

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51
ggttacacct ttaccagcta tggt                                        24

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Gly Tyr Thr Phe Thr Ser Tyr Gly
 1               5

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
atcagcggtt acaatggtaa caca                                        24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Ser Gly Tyr Asn Gly Asn Thr
 1               5

<210> SEQ ID NO 55
<211> LENGTH: 51
<212> TYPE: DNA
<213> ORGANISM: Artificial Sequence
<220> FEATURE:
<223> OTHER INFORMATION: Synthetic

<400> SEQUENCE: 55
gcgagatggg gtatagcaac tcgtccctac tactactacg gtatggacgt c          51

<210> SEQ ID NO 56
<211> LENGTH: 17
<212> TYPE: PRT
<213> ORGANISM: Artificial Sequence
<220> FEATURE:
<223> OTHER INFORMATION: Synthetic

<400> SEQUENCE: 56

Ala Arg Trp Gly Ile Ala Thr Arg Pro Tyr Tyr Tyr Gly Met Asp
 1               5                  10                  15

Val

<210> SEQ ID NO 57
<211> LENGTH: 321
<212> TYPE: DNA
<213> ORGANISM: Artificial Sequence
<220> FEATURE:
<223> OTHER INFORMATION: Synthetic

<400> SEQUENCE: 57
gacatccaga tgacccagtc tccatcctca ctgtctgcat ctgtaggaga cagagtcacc      60
atcacttgtc gggcgagtca ggacattacc aattatttag cctggtttca gcagaaacca     120
gggaaagccc ctaagtccct gatctatgct gcatccagtt tgcaaagtgg ggtcccatca     180
aagttcagcg gcagtggatc tgggacagat ttcactctca ccatcagcag cctgcagcct     240
gaagattttg caacttatta ctgccaacag tataatagtt accctcccac tttcggccct     300
gggaccaaag tggatatcaa a                                                321

<210> SEQ ID NO 58
<211> LENGTH: 107
<212> TYPE: PRT
<213> ORGANISM: Artificial Sequence
<220> FEATURE:
<223> OTHER INFORMATION: Synthetic

<400> SEQUENCE: 58

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Thr Asn Tyr
             20                  25                  30

Leu Ala Trp Phe Gln Gln Lys Pro Gly Lys Ala Pro Lys Ser Leu Ile
         35                  40                  45

Tyr Ala Ala Ser Ser Leu Gln Ser Gly Val Pro Ser Lys Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                 85                  90                  95

Thr Phe Gly Pro Gly Thr Lys Val Asp Ile Lys
            100                 105

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59
caggacatta ccaattat				18

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Asp Ile Thr Asn Tyr
 1               5

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 gctgcatcc				9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Ala Ala Ser
 1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
caacagtata atagttaccc tcccact				27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Gln Gln Tyr Asn Ser Tyr Pro Pro Thr
 1               5

<210> SEQ ID NO 65
<211> LENGTH: 363
<212> TYPE: DNA
<213> ORGANISM: Artificial Sequence
<220> FEATURE:
<223> OTHER INFORMATION: Synthetic

<400> SEQUENCE: 65
gaggtgcagc tgttggagtc tgggggaggc ttggtacagc cggggggtc cctgagagtc				60 tcctgtgcag cctctggatt cacctttagc acctctgcca tgagctgggt ccgccaggct				120

```
ccagggaagg ggcttgagtg ggtctcaggt attagtggta ttggaggtgg tagcacatac    180
tacgcagact ccgtgaaggg ccggttcacc atctccagag acaattccaa gaacacgctg    240
tatctgcaaa tgaacagcct gagagccgag gacacggccg tatatttctg tgcgaaattt    300
tataagtgga attcatatat ttttgatctc tggggccagg ggacaatggt caccgtctct    360
tca                                                                  363
```

<210> SEQ ID NO 66
<211> LENGTH: 121
<212> TYPE: PRT
<213> ORGANISM: Artificial Sequence
<220> FEATURE:
<223> OTHER INFORMATION: Synthetic

<400> SEQUENCE: 66

```
Glu Val Gln Leu Leu Glu Ser Gly Gly Gly Leu Val Gln Pro Gly Gly
 1               5                  10                  15

Ser Leu Arg Val Ser Cys Ala Ala Ser Gly Phe Thr Phe Ser Thr Ser
            20                  25                  30

Ala Met Ser Trp Val Arg Gln Ala Pro Gly Lys Gly Leu Glu Trp Val
        35                  40                  45

Ser Gly Ile Ser Gly Ile Gly Gly Ser Thr Tyr Tyr Ala Asp Ser
    50                  55                  60

Val Lys Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Phe
                85                  90                  95

Cys Ala Lys Phe Tyr Lys Trp Asn Ser Tyr Ile Phe Asp Leu Trp Gly
            100                 105                 110

Gln Gly Thr Met Val Thr Val Ser Ser
        115                 120
```

<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67

```
ggattcacct ttagcacctc tgcc                                            24
```

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

```
Gly Phe Thr Phe Ser Thr Ser Ala
 1               5
```

<210> SEQ ID NO 69
<211> LENGTH: 27
<212> TYPE: DNA
<213> ORGANISM: Artificial Sequence
<220> FEATURE:
<223> OTHER INFORMATION: Synthetic

<400> SEQUENCE: 69
attagtggta ttggaggtgg tagcaca 27

<210> SEQ ID NO 70
<211> LENGTH: 9
<212> TYPE: PRT
<213> ORGANISM: Artificial Sequence
<220> FEATURE:
<223> OTHER INFORMATION: Synthetic

<400> SEQUENCE: 70

Ile Ser Gly Ile Gly Gly Gly Ser Thr
1               5

<210> SEQ ID NO 71
<211> LENGTH: 39
<212> TYPE: DNA
<213> ORGANISM: Artificial Sequence
<220> FEATURE:
<223> OTHER INFORMATION: Synthetic

<400> SEQUENCE: 71
gcgaaatttt ataagtggaa ttcatatatt tttgatctc                    39

<210> SEQ ID NO 72
<211> LENGTH: 13
<212> TYPE: PRT
<213> ORGANISM: Artificial Sequence
<220> FEATURE:
<223> OTHER INFORMATION: Synthetic

<400> SEQUENCE: 72

Ala Lys Phe Tyr Lys Trp Asn Ser Tyr Ile Phe Asp Leu
1               5                   10

<210> SEQ ID NO 73
<211> LENGTH: 321
<212> TYPE: DNA
<213> ORGANISM: Artificial Sequence
<220> FEATURE:
<223> OTHER INFORMATION: Synthetic

<400> SEQUENCE: 73
gaaattgtgt tgacgcagtc tccagacacc ctatctttgt ctccagggga aagagccacc    60
ctctcctgca gggccagtca gagtgttagt agcagctact tgcctggta ccagcagaag   120 cctggccagg ctcccaggct cctcatgtat agtgcatcca gcagggccac tggcatccca   180
gacaggttca gtggcagtgg gtctgggaca gacttctctc tcaccatcag cagattggag   240
cctgaagatt ttgcagtgta ttactgtcag cagtatggta ggtcactcac tttcggcgga   300
gggaccaagg tggagatcaa g                                            321

<210> SEQ ID NO 74
<211> LENGTH: 107
<212> TYPE: PRT
<213> ORGANISM: Artificial Sequence
<220> FEATURE:
<223> OTHER INFORMATION: Synthetic

<400> SEQUENCE: 74

Glu Ile Val Leu Thr Gln Ser Pro Asp Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Phe Ala Trp Tyr Gln Gln Lys Pro Gly Gln Ala Pro Arg Leu Leu

```
            35                  40                  45
Met Tyr Ser Ala Ser Ser Arg Ala Thr Gly Ile Pro Asp Arg Phe Ser
         50                  55                  60

Gly Ser Gly Ser Gly Thr Asp Phe Ser Leu Thr Ile Ser Arg Leu Glu
 65                  70                  75                  80

Pro Glu Asp Phe Ala Val Tyr Tyr Cys Gln Gln Tyr Gly Arg Ser Leu
                 85                  90                  95

Thr Phe Gly Gly Gly Thr Lys Val Glu Ile Lys
            100                 105

<210> SEQ ID NO 75
<211> LENGTH: 21
<212> TYPE: DNA
<213> ORGANISM: Artificial Sequence
<220> FEATURE:
<223> OTHER INFORMATION: Synthetic

<400> SEQUENCE: 75
cagagtgtta gtagcagcta c                                              21

<210> SEQ ID NO 76
<211> LENGTH: 7
<212> TYPE: PRT
<213> ORGANISM: Artificial Sequence
<220> FEATURE:
<223> OTHER INFORMATION: Synthetic

<400> SEQUENCE: 76

Gln Ser Val Ser Ser Ser Tyr
 1               5

<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77 agtgcatcc                                                             9

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Ser Ala Ser
 1

<210> SEQ ID NO 79
<211> LENGTH: 24
<212> TYPE: DNA
<213> ORGANISM: Artificial Sequence
<220> FEATURE:
<223> OTHER INFORMATION: Synthetic

<400> SEQUENCE: 79
cagcagtatg gtaggtcact cact                                           24

<210> SEQ ID NO 80
<211> LENGTH: 8
```

<212> TYPE: PRT
<213> ORGANISM: Artificial Sequence
<220> FEATURE:
<223> OTHER INFORMATION: Synthetic

<400> SEQUENCE: 80

Gln Gln Tyr Gly Arg Ser Leu Thr
 1               5

<210> SEQ ID NO 81
<211> LENGTH: 360
<212> TYPE: DNA
<213> ORGANISM: Artificial Sequence
<220> FEATURE:
<223> OTHER INFORMATION: Synthetic

<400> SEQUENCE: 81
gaggtgcagc tgttggagtc tgggggaggc ttggtacagt ctggggggtc actgagactc      60
tcctgtgcag cctctggatt cagctttaac aactatgcca tgagctgggt ccgccaggct     120
ccagggaagg ggctggagtg ggtctcattt attagtggta gtggtggtag tacatactac     180
gcagactccg tgaagggccg gttcaccatc tccagagaca attccaagaa tacgctgtat     240
ctgcaaatga acagcctgag agtcgaggac acggccgttt tttactgtgc gaaagacaga     300
tacaactatg gtaccttctt tgactactgg ggccagggaa ccctggtcac cgtctcctca     360

<210> SEQ ID NO 82
<211> LENGTH: 120
<212> TYPE: PRT
<213> ORGANISM: Artificial Sequence
<220> FEATURE:
<223> OTHER INFORMATION: Synthetic

<400> SEQUENCE: 82

Glu Val Gln Leu Leu Glu Ser Gly Gly Gly Leu Val Gln Ser Gly Gly
 1               5                  10                  15

Ser Leu Arg Leu Ser Cys Ala Ala Ser Gly Phe Ser Phe Asn Asn Tyr
            20                  25                  30

Ala Met Ser Trp Val Arg Gln Ala Pro Gly Lys Gly Leu Glu Trp Val
        35                  40                  45

Ser Phe Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Phe Tyr Cys
                85                  90                  95

Ala Lys Asp Arg Tyr Asn Tyr Gly Thr Phe Phe Asp Tyr Trp Gly Gln
            100                 105                 110

Gly Thr Leu Val Thr Val Ser Ser
        115                 120

<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83
ggattcagct ttaacaacta tgcc                                             24

<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

Gly Phe Ser Phe Asn Asn Tyr Ala
 1               5

<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85
attagtggta gtggtggtag taca                                          24

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Ile Ser Gly Ser Gly Gly Ser Thr
 1               5

<210> SEQ ID NO 87
<211> LENGTH: 39
<212> TYPE: DNA
<213> ORGANISM: Artificial Sequence
<220> FEATURE:
<223> OTHER INFORMATION: Synthetic

<400> SEQUENCE: 87
gcgaaagaca gatacaacta tggtaccttc tttgactac                          39

<210> SEQ ID NO 88
<211> LENGTH: 13
<212> TYPE: PRT
<213> ORGANISM: Artificial Sequence
<220> FEATURE:
<223> OTHER INFORMATION: Synthetic

<400> SEQUENCE: 88

Ala Lys Asp Arg Tyr Asn Tyr Gly Thr Phe Phe Asp Tyr
 1               5                  10

<210> SEQ ID NO 89
<211> LENGTH: 339
<212> TYPE: DNA
<213> ORGANISM: Artificial Sequence
<220> FEATURE:
<223> OTHER INFORMATION: Synthetic

<400> SEQUENCE: 89
gacatcgtga tgacccagtc tccagactcc ctggctgtgt ctctgggcga gagggccacc    60
atcaactgca aatccagcca gagtgtttta tacagctcca acaataagaa ctacttaact   120
tggtaccagc agaaaccagg acagcctcct aaattgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttatagtact    300
cctccgacgt tcggcctagg gaccaaggtg gaaatcaaa                            339

<210> SEQ ID NO 90
<211> LENGTH: 113
<212> TYPE: PRT
<213> ORGANISM: Artificial Sequence
<220> FEATURE:
<223> OTHER INFORMATION: Synthetic

<400> SEQUENCE: 90

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Thr Phe Gly Leu Gly Thr Lys Val Glu Ile
            100                 105                 110

Lys

<210> SEQ ID NO 91
<211> LENGTH: 36
<212> TYPE: DNA
<213> ORGANISM: Artificial Sequence
<220> FEATURE:
<223> OTHER INFORMATION: Synthetic

<400> SEQUENCE: 91
cagagtgttt tatacagctc caacaataag aactac                               36

<210> SEQ ID NO 92
<211> LENGTH: 12
<212> TYPE: PRT
<213> ORGANISM: Artificial Sequence
<220> FEATURE:
<223> OTHER INFORMATION: Synthetic

<400> SEQUENCE: 92

Gln Ser Val Leu Tyr Ser Ser Asn Asn Lys Asn Tyr
1               5                   10

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 tgggcatct                                                             9

<210> SEQ ID NO 94
<211> LENGTH: 3
<212> TYPE: PRT

<213> ORGANISM: Artificial Sequence
<220> FEATURE:
<223> OTHER INFORMATION: Synthetic

<400> SEQUENCE: 94

Trp Ala Ser
 1

<210> SEQ ID NO 95
<211> LENGTH: 27
<212> TYPE: DNA
<213> ORGANISM: Artificial Sequence
<220> FEATURE:
<223> OTHER INFORMATION: Synthetic

<400> SEQUENCE: 95
cagcaatatt atagtactcc tccgacg                                              27

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

Gln Gln Tyr Tyr Ser Thr Pro Pro Thr
 1               5

<210> SEQ ID NO 97
<211> LENGTH: 372
<212> TYPE: DNA
<213> ORGANISM: Artificial Sequence
<220> FEATURE:
<223> OTHER INFORMATION: Synthetic

<400> SEQUENCE: 97
gaagtgcagc tggtggagtc tgggggaggc ttggtacagc ctggggagtc cctgagactc          60
tcctgtgcag cctctggatt caccttagc aactatgcca tgagctgggt ccgccaggct         120
ccagggaagg gctggagtg gtctcagtt attagtggta gtggtggtag cacatactac          180
gcagactccg tgaagggccg gttcaccatg tccagagaca attccaagaa cacgctgtat        240
ctgcaaatga acagcctgag agccgaggac acggccgtat attactgtgc gaaaccccg         300 agtagagcag ctcgatactt caactacggt atggacgtct ggggccaagg gaccacggtc        360
accgtctcct ca                                                            372

<210> SEQ ID NO 98
<211> LENGTH: 124
<212> TYPE: PRT
<213> ORGANISM: Artificial Sequence
<220> FEATURE:
<223> OTHER INFORMATION: Synthetic

<400> SEQUENCE: 98

Glu Val Gln Leu Val Glu Ser Gly Gly Gly Leu Val Gln Pro Gly Glu
 1               5                  10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Val Ile Ser Gly Ser Gly Gly Ser Thr Tyr Tyr Ala Asp Ser Val
    50                  55                  60

Lys Gly Arg Phe Thr Met Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Pro Ser Arg Ala Ala Arg Tyr Phe Asn Tyr Gly Met Asp
            100                 105                 110

Val Trp Gly Gln Gly Thr Thr Val Thr Val Ser Ser
        115                 120

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99
ggattcacct ttagcaacta tgcc                                    24

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

Gly Phe Thr Phe Ser Asn Tyr Ala
1               5

<210> SEQ ID NO 101
<211> LENGTH: 24
<212> TYPE: DNA
<213> ORGANISM: Artificial Sequence
<220> FEATURE:
<223> OTHER INFORMATION: Synthetic

<400> SEQUENCE: 101
attagtggta gtggtggtag caca                                    24

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

Ile Ser Gly Ser Gly Gly Ser Thr
1               5

<210> SEQ ID NO 103
<211> LENGTH: 51
<212> TYPE: DNA
<213> ORGANISM: Artificial Sequence
<220> FEATURE:
<223> OTHER INFORMATION: Synthetic

<400> SEQUENCE: 103
gcgaaacccc cgagtagagc agctcgatac ttcaactacg gtatggacgt c       51

<210> SEQ ID NO 104
<211> LENGTH: 17
<212> TYPE: PRT

<210> SEQ ID NO 104
<211> LENGTH: 16 (implied)
<213> ORGANISM: Artificial Sequence
<220> FEATURE:
<223> OTHER INFORMATION: Synthetic

<400> SEQUENCE: 104

Ala Lys Pro Pro Ser Arg Ala Ala Arg Tyr Phe Asn Tyr Gly Met Asp
1               5                   10                  15

Val

<210> SEQ ID NO 105
<211> LENGTH: 321
<212> TYPE: DNA
<213> ORGANISM: Artificial Sequence
<220> FEATURE:
<223> OTHER INFORMATION: Synthetic

<400> SEQUENCE: 105

```
gccatccgga tgacccagtc cccatcttcc gtgtctgcat ctgtaggaga cagagtcacc    60
atcacttgtc gggcgagtca gggtattagc agctggttag cctggtatca gcagaaacca   120
gggaaagccc ctaagctcct gatctatgct gcatccagtt tgcaaagtgg ggtcccatca   180
aggttcagcg gcagtggatc tgggacagat tcactctca ccatcagcag cctgcagcct   240
gaagattttg caacttacta ttgtcaacag gctaacagtt tcccgttcac tttcggcgga   300
gggaccaagg tggagatcaa a                                             321
```

<210> SEQ ID NO 106
<211> LENGTH: 107
<212> TYPE: PRT
<213> ORGANISM: Artificial Sequence
<220> FEATURE:
<223> OTHER INFORMATION: Synthetic

<400> SEQUENCE: 106

Ala Ile Arg Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Gly Gly Thr Lys Val Glu Ile Lys
            100                 105

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
cagggtatta gcagctgg                                                  18

<210> SEQ ID NO 108
<211> LENGTH: 6

```
<212> TYPE: PRT
<213> ORGANISM: Artificial Sequence
<220> FEATURE:
<223> OTHER INFORMATION: Synthetic

<400> SEQUENCE: 108

Gln Gly Ile Ser Ser Trp
 1               5

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 gctgcatcc                                                                  9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Ala Ala Ser
 1

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
caacaggcta acagtttccc gttcact                                             27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Gln Gln Ala Asn Ser Phe Pro Phe Thr
 1               5

<210> SEQ ID NO 113
<211> LENGTH: 363
<212> TYPE: DNA
<213> ORGANISM: Artificial Sequence
<220> FEATURE:
<223> OTHER INFORMATION: Synthetic

<400> SEQUENCE: 113
gaagtgcagc tggtggagtc tgggggaggc gtggtccagc ctgggaggtc cctgagactc          60
tcctgtgcag cgtctggatt caccttcagt agctatggca tgcactgggt ccgccaggct         120
ccgggcaagg gctggagtg gtgtcattt atatggtatg atggaagtaa taaatactat           180
gcagactccg tgaagggccg attcaccatc tccagagaca attccaagaa cacgctgtat         240
ctgcaaatga acagcctgac agccgaggac acggctgtat attattgtgc gagaagaggt         300
```

```
atcctaactg gaactaccgc ttttgatatc tggggccaag ggacaatggt caccgtctct        360
tca                                                                     363
```

<210> SEQ ID NO 114
<211> LENGTH: 121
<212> TYPE: PRT
<213> ORGANISM: Artificial Sequence
<220> FEATURE:
<223> OTHER INFORMATION: Synthetic

<400> SEQUENCE: 114

```
Glu Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ser Phe Ile Trp Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Thr Ala Glu Asp Thr Ala Val Tyr Tyr Cys
                 85                  90                  95

Ala Arg Arg Gly Ile Leu Thr Gly Thr Thr Ala Phe Asp Ile Trp Gly
            100                 105                 110

Gln Gly Thr Met Val Thr Val Ser Ser
        115                 120
```

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115

```
ggattcacct tcagtagcta tggc                                               24
```

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

```
Gly Phe Thr Phe Ser Ser Tyr Gly
  1               5
```

<210> SEQ ID NO 117
<211> LENGTH: 24
<212> TYPE: DNA
<213> ORGANISM: Artificial Sequence
<220> FEATURE:
<223> OTHER INFORMATION: Synthetic

<400> SEQUENCE: 117

```
atatggtatg atggaagtaa taaa                                               24
```

<210> SEQ ID NO 118
<211> LENGTH: 8

```
<212> TYPE: PRT
<213> ORGANISM: Artificial Sequence
<220> FEATURE:
<223> OTHER INFORMATION: Synthetic

<400> SEQUENCE: 118

Ile Trp Tyr Asp Gly Ser Asn Lys
 1               5

<210> SEQ ID NO 119
<211> LENGTH: 42
<212> TYPE: DNA
<213> ORGANISM: Artificial Sequence
<220> FEATURE:
<223> OTHER INFORMATION: Synthetic

<400> SEQUENCE: 119
gcgagaagag gtatcctaac tggaactacc gcttttgata tc                          42

<210> SEQ ID NO 120
<211> LENGTH: 14
<212> TYPE: PRT
<213> ORGANISM: Artificial Sequence
<220> FEATURE:
<223> OTHER INFORMATION: Synthetic

<400> SEQUENCE: 120

Ala Arg Arg Gly Ile Leu Thr Gly Thr Thr Ala Phe Asp Ile
 1               5                  10

<210> SEQ ID NO 121
<211> LENGTH: 321
<212> TYPE: DNA
<213> ORGANISM: Artificial Sequence
<220> FEATURE:
<223> OTHER INFORMATION: Synthetic

<400> SEQUENCE: 121
gacatccaga tgacccagtc tccatcctcc ctgtctgcat ctgtgggaga cagagtcacc       60
atcacttgcc gggcaagtca gagcattagc agttatttga attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatccggag tctgatacct     240
gaagattttg caacttacta ctgtcaacag acttacaata cccccattca ctttcggccct    300 gggaccaagg tggaaatcaa a                                                321

<210> SEQ ID NO 122
<211> LENGTH: 107
<212> TYPE: PRT
<213> ORGANISM: Artificial Sequence
<220> FEATURE:
<223> OTHER INFORMATION: Synthetic

<400> SEQUENCE: 122

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60
```

Ser Gly Ser Gly Thr Asp Phe Thr Leu Thr Ile Arg Ser Leu Ile Pro
 65                  70                  75                  80

Glu Asp Phe Ala Thr Tyr Tyr Cys Gln Gln Thr Tyr Asn Thr Pro Phe
                 85                  90                  95

Thr Phe Gly Pro Gly Thr Lys Val Glu Ile Lys
            100                 105

<210> SEQ ID NO 123
<211> LENGTH: 18
<212> TYPE: DNA
<213> ORGANISM: Artificial Sequence
<220> FEATURE:
<223> OTHER INFORMATION: Synthetic

<400> SEQUENCE: 123
cagagcatta gcagttat                                              18

<210> SEQ ID NO 124
<211> LENGTH: 6
<212> TYPE: PRT
<213> ORGANISM: Artificial Sequence
<220> FEATURE:
<223> OTHER INFORMATION: Synthetic

<400> SEQUENCE: 124

Gln Ser Ile Ser Ser Tyr
 1               5

<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125 gctgcatcc                                                         9

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Ala Ala Ser
 1

<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127
caacagactt acaataccccc attcact                                   27

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Gln Gln Thr Tyr Asn Thr Pro Phe Thr
1               5

<210> SEQ ID NO 129
<211> LENGTH: 363
<212> TYPE: DNA
<213> ORGANISM: Artificial Sequence
<220> FEATURE:
<223> OTHER INFORMATION: Synthetic

<400> SEQUENCE: 129

```
caggtgcagc tggtggagtc tgggggaggc gtggtccagc ctggagggtc cctgagactc      60
tcctgtgcag cgtctggatt cagtttcagt gactatgtca tgcactgggt ccgccaggct     120
ccaggcaagg ggctggagtg gtggcatct atatggtttg atggaagtaa tgaactctat     180
gcagactccg tgaagggccg attcaccatc tccagagaca attccaagaa cacgctgttt     240
ctgcaaatga acagtctgag agccgaggac acggctgtgt attactgtgc gaaaaaggga     300
gttttggtag ctacctctgc ttttcatatc tggggccaag ggacaatggt caccgtctct     360
tca                                                                    363
```

<210> SEQ ID NO 130
<211> LENGTH: 121
<212> TYPE: PRT
<213> ORGANISM: Artificial Sequence
<220> FEATURE:
<223> OTHER INFORMATION: Synthetic

<400> SEQUENCE: 130

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Asp Tyr
            20                  25                  30

Val Met His Trp Val Arg Gln Ala Pro Gly Lys Gly Leu Glu Trp Val
        35                  40                  45

Ala Ser Ile Trp Phe Asp Gly Ser Asn Glu Leu Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Lys Gly Val Leu Val Ala Thr Ser Ala Phe His Ile Trp Gly
            100                 105                 110

Gln Gly Thr Met Val Thr Val Ser Ser
        115                 120

<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131

```
ggattcagtt tcagtgacta tgtc                                              24
```

<210> SEQ ID NO 132
<211> LENGTH: 8
<212> TYPE: PRT

```
<213> ORGANISM: Artificial Sequence
<220> FEATURE:
<223> OTHER INFORMATION: Synthetic

<400> SEQUENCE: 132

Gly Phe Ser Phe Ser Asp Tyr Val
 1               5

<210> SEQ ID NO 133
<211> LENGTH: 24
<212> TYPE: DNA
<213> ORGANISM: Artificial Sequence
<220> FEATURE:
<223> OTHER INFORMATION: Synthetic

<400> SEQUENCE: 133
atatggtttg atggaagtaa tgaa                                            24

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

Ile Trp Phe Asp Gly Ser Asn Glu
 1               5

<210> SEQ ID NO 135
<211> LENGTH: 42
<212> TYPE: DNA
<213> ORGANISM: Artificial Sequence
<220> FEATURE:
<223> OTHER INFORMATION: Synthetic

<400> SEQUENCE: 135
gcgaaaaagg gagttttggt agctacctct gctttcata tc                         42

<210> SEQ ID NO 136
<211> LENGTH: 14
<212> TYPE: PRT
<213> ORGANISM: Artificial Sequence
<220> FEATURE:
<223> OTHER INFORMATION: Synthetic

<400> SEQUENCE: 136

Ala Lys Lys Gly Val Leu Val Ala Thr Ser Ala Phe His Ile
 1               5                   10

<210> SEQ ID NO 137
<211> LENGTH: 324
<212> TYPE: DNA
<213> ORGANISM: Artificial Sequence
<220> FEATURE:
<223> OTHER INFORMATION: Synthetic

<400> SEQUENCE: 137
gccatccaga tgacccagtc tccatcctcc ctgtctgcat ctgtaggaga cagagtcacc     60
atcacttgcc gggcaagtca gaacattaac aactatttaa attggtatca tcagaaacca    120
gggaaagccc ctaatctcct aatttatgct gcatccagtt tgcaaagtgg ggtcccatca    180
aggttcagtg gcagtggatc tgggacagat tacactctca ccatcagcag tctgcaacct    240
gaagattttg gaattacta ctgtcaacag agttacagca cttccatgta cacttttggc    300
``` cagggacca agctggagat caaa                                              324

<210> SEQ ID NO 138
<211> LENGTH: 108
<212> TYPE: PRT
<213> ORGANISM: Artificial Sequence
<220> FEATURE:
<223> OTHER INFORMATION: Synthetic

<400> SEQUENCE: 138

Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Asn Ile Asn Asn Tyr
            20                  25                  30

Leu Asn Trp Tyr His Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Gly Asn Tyr Tyr Cys Gln Gln Ser Tyr Ser Thr Ser Met
                85                  90                  95

Tyr Thr Phe Gly Gln Gly Thr Lys Leu Glu Ile Lys
            100                 105

<210> SEQ ID NO 139
<211> LENGTH: 18
<212> TYPE: DNA
<213> ORGANISM: Artificial Sequence
<220> FEATURE:
<223> OTHER INFORMATION: Synthetic

<400> SEQUENCE: 139
cagaacatta acaactat                                                    18

<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

Gln Asn Ile Asn Asn Tyr
 1               5

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141 gctgcatcc                                                               9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Ala Ala Ser
 1

<210> SEQ ID NO 143
<211> LENGTH: 30
<212> TYPE: DNA
<213> ORGANISM: Artificial Sequence
<220> FEATURE:
<223> OTHER INFORMATION: Synthetic

<400> SEQUENCE: 143
caacagagtt acagcacttc catgtacact                                      30

<210> SEQ ID NO 144
<211> LENGTH: 10
<212> TYPE: PRT
<213> ORGANISM: Artificial Sequence
<220> FEATURE:
<223> OTHER INFORMATION: Synthetic

<400> SEQUENCE: 144

Gln Gln Ser Tyr Ser Thr Ser Met Tyr Thr
 1               5                  10

<210> SEQ ID NO 145
<211> LENGTH: 372
<212> TYPE: DNA
<213> ORGANISM: Artificial Sequence
<220> FEATURE:
<223> OTHER INFORMATION: Synthetic

<400> SEQUENCE: 145
gaggtgcagc tggtggagtc tgggggaggc ttggtacagc ctgggggggtc cctgagactc     60 tcctgtgcag cctctggatt cacctttagc agctatgcca tgagctgggt ccgccaggct    120
ccagggaagg ggctggagtg ggtctcagtt attagtggta gtggaggtag cacatactac    180
gcagacgccg tgaagggccg gttcaccatc tccagagaca attccaagca cacgctgtat    240
ctgcaaatga acagcctgag agccgaggac acggccgtat attactgtac gaaacccctca    300 tcttatagca gttcgaactt ctattatggt atggacgtct ggggccaagg gtccacggtc    360
accgtctcct ca                                                        372

<210> SEQ ID NO 146
<211> LENGTH: 124
<212> TYPE: PRT
<213> ORGANISM: Artificial Sequence
<220> FEATURE:
<223> OTHER INFORMATION: Synthetic

<400> SEQUENCE: 146

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Ser Gly Gly Ser Thr Tyr Tyr Ala Asp Ala Val
    50                  55                  60

Lys Gly Arg Phe Thr Ile Ser Arg Asp Asn Ser Lys His Thr Leu Tyr
65                  70                  75                  80

Leu Gln Met Asn Ser Leu Arg Ala Glu Asp Thr Ala Val Tyr Tyr Cys

```
                    85                  90                  95
Thr Lys Pro Ser Ser Tyr Ser Ser Asn Phe Tyr Tyr Gly Met Asp
                100                 105                 110

Val Trp Gly Gln Gly Ser Thr Val Thr Val Ser Ser
        115                 120
```

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147
ggattcacct ttagcagcta tgcc         24

<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

Gly Phe Thr Phe Ser Ser Tyr Ala
1               5

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149
attagtggta gtggaggtag caca         24

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ile Ser Gly Ser Gly Gly Ser Thr
1               5

<210> SEQ ID NO 151
<211> LENGTH: 51
<212> TYPE: DNA
<213> ORGANISM: Artificial Sequence
<220> FEATURE:
<223> OTHER INFORMATION: Synthetic

<400> SEQUENCE: 151
acgaaaccct catcttatag cagttcgaac ttctattatg gtatggacgt c         51

<210> SEQ ID NO 152
<211> LENGTH: 17
<212> TYPE: PRT
<213> ORGANISM: Artificial Sequence
<220> FEATURE:
<223> OTHER INFORMATION: Synthetic

<400> SEQUENCE: 152

Thr Lys Pro Ser Ser Tyr Ser Ser Asn Phe Tyr Tyr Gly Met Asp
1               5                   10                  15

Val

<210> SEQ ID NO 153
<211> LENGTH: 321
<212> TYPE: DNA
<213> ORGANISM: Artificial Sequence
<220> FEATURE:
<223> OTHER INFORMATION: Synthetic

<400> SEQUENCE: 153
gacatccagt tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccagtt tgcaaagtgg ggtcccatca     180
aggttcagcg gcagtggatc tgggacagat tcactctcac ccatcagcag cctgcagcct     240
gaagattttg caacttacta ttgtcagcag actaacagtt ccccattccc tttcggccct     300
gggaccaaag tggatatcaa a                                               321

<210> SEQ ID NO 154
<211> LENGTH: 107
<212> TYPE: PRT
<213> ORGANISM: Artificial Sequence
<220> FEATURE:
<223> OTHER INFORMATION: Synthetic

<400> SEQUENCE: 154

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Ser Phe Pro Phe
                85                  90                  95

Pro Phe Gly Pro Gly Thr Lys Val Asp Ile Lys
            100                 105

<210> SEQ ID NO 155
<211> LENGTH: 18
<212> TYPE: DNA
<213> ORGANISM: Artificial Sequence
<220> FEATURE:
<223> OTHER INFORMATION: Synthetic

<400> SEQUENCE: 155
cagggtatta gcagctgg                                                    18

<210> SEQ ID NO 156
<211> LENGTH: 6
<212> TYPE: PRT
<213> ORGANISM: Artificial Sequence
<220> FEATURE:
<223> OTHER INFORMATION: Synthetic -continued

<400> SEQUENCE: 156

Gln Gly Ile Ser Ser Trp
1               5

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 gctgcatcc                                                                 9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Ala Ala Ser
1

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
cagcagacta acagtttccc attccct                                            27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Gln Gln Thr Asn Ser Phe Pro Phe Pro
1               5

<210> SEQ ID NO 161
<211> LENGTH: 372
<212> TYPE: DNA
<213> ORGANISM: Artificial Sequence
<220> FEATURE:
<223> OTHER INFORMATION: Synthetic

<400> SEQUENCE: 161
gaggtgcagc tggtggagtc tgggggaggc ttggtacagg ctggggggtc cctgagactc         60
tcctgtgtag cctctggatt cacctttagc agctatgcca tgagctgggt ccgccaggct        120
ccagggaagg ggctggagtg ggtctcagct attagtggta gtggtggtag cacatactcc        180
gcagactccg tgaagggccg gttcaccatc tccagagaca attccaagaa cacgctgtat        240
ctgcaaatga acagcctgag agccgaggac acggccgtat attactgtac gaaaccctca        300
tcttatagca gctcgaactt ctactacggt atggacgtct ggggccaagg gaccacggtc        360
accgtctcct ca                                                           372

<210> SEQ ID NO 162
<211> LENGTH: 124
<212> TYPE: PRT
<213> ORGANISM: Artificial Sequence
<220> FEATURE:
<223> OTHER INFORMATION: Synthetic

<400> SEQUENCE: 162

```
Glu Val Gln Leu Val Glu Ser Gly Gly Gly Leu Val Gln Ala Gly Gly
 1               5                  10                  15
Ser Leu Arg Leu Ser Cys Val Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Ser Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Thr Lys Pro Ser Ser Tyr Ser Ser Asn Phe Tyr Tyr Gly Met Asp
            100                 105                 110
Val Trp Gly Gln Gly Thr Thr Val Thr Val Ser Ser
        115                 120
```

<210> SEQ ID NO 163
<211> LENGTH: 24
<212> TYPE: DNA
<213> ORGANISM: Artificial Sequence
<220> FEATURE:
<223> OTHER INFORMATION: Synthetic

<400> SEQUENCE: 163
ggattcacct ttagcagcta tgcc                                        24

<210> SEQ ID NO 164
<211> LENGTH: 8
<212> TYPE: PRT
<213> ORGANISM: Artificial Sequence
<220> FEATURE:
<223> OTHER INFORMATION: Synthetic

<400> SEQUENCE: 164

```
Gly Phe Thr Phe Ser Ser Tyr Ala
 1               5
```

<210> SEQ ID NO 165
<211> LENGTH: 24
<212> TYPE: DNA
<213> ORGANISM: Artificial Sequence
<220> FEATURE:
<223> OTHER INFORMATION: Synthetic

<400> SEQUENCE: 165
attagtggta gtggtggtag caca                                        24

<210> SEQ ID NO 166
<211> LENGTH: 8
<212> TYPE: PRT
<213> ORGANISM: Artificial Sequence
<220> FEATURE:
<223> OTHER INFORMATION: Synthetic

<400> SEQUENCE: 166

Ile Ser Gly Ser Gly Gly Ser Thr
 1               5

<210> SEQ ID NO 167
<211> LENGTH: 51
<212> TYPE: DNA
<213> ORGANISM: Artificial Sequence
<220> FEATURE:
<223> OTHER INFORMATION: Synthetic

<400> SEQUENCE: 167
acgaaaccct catcttatag cagctcgaac ttctactacg gtatggacgt c                    51

<210> SEQ ID NO 168
<211> LENGTH: 17
<212> TYPE: PRT
<213> ORGANISM: Artificial Sequence
<220> FEATURE:
<223> OTHER INFORMATION: Synthetic

<400> SEQUENCE: 168

Thr Lys Pro Ser Ser Tyr Ser Ser Ser Asn Phe Tyr Tyr Gly Met Asp
 1               5                  10                  15

Val

<210> SEQ ID NO 169
<211> LENGTH: 321
<212> TYPE: DNA
<213> ORGANISM: Artificial Sequence
<220> FEATURE:
<223> OTHER INFORMATION: Synthetic

<400> SEQUENCE: 169
gacatccaga tgacccagtc tccatcttcc gtgtctgcat ctgtaggaga cagagtcacc           60
atcacttgtc gggcgagtca gggtattagc agctggttag cctggtatca gcagaaacca          120
gggaaagccc ctaagctcct gatctatact gcatccagtt tgcaaagtgg ggtcccatca          180
aggttcagcg gcagtggatc taggacagat ttcactctca ccatcagcag cctgcagcct          240
gaagattttg caacttacta ttgtcaacag actaacagtc tcccactcac tttcggccct          300
gggaccaagg tggagatcaa a                                                    321

<210> SEQ ID NO 170
<211> LENGTH: 107
<212> TYPE: PRT
<213> ORGANISM: Artificial Sequence
<220> FEATURE:
<223> OTHER INFORMATION: Synthetic

<400> SEQUENCE: 170

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Thr Ala Ser Ser Leu Gln Ser Gly Val Pro Ser Arg Phe Ser Gly
        50                  55                  60

Ser Gly Ser Arg Thr Asp Phe Thr Leu Thr Ile Ser Ser Leu Gln Pro
65                  70                  75                  80

Glu Asp Phe Ala Thr Tyr Tyr Cys Gln Gln Thr Asn Ser Leu Pro Leu
                85                  90                  95

Thr Phe Gly Pro Gly Thr Lys Val Glu Ile Lys
            100                 105

<210> SEQ ID NO 171
<211> LENGTH: 18
<212> TYPE: DNA
<213> ORGANISM: Artificial Sequence
<220> FEATURE:
<223> OTHER INFORMATION: Synthetic

<400> SEQUENCE: 171
cagggtatta gcagctgg                                                    18

<210> SEQ ID NO 172
<211> LENGTH: 6
<212> TYPE: PRT
<213> ORGANISM: Artificial Sequence
<220> FEATURE:
<223> OTHER INFORMATION: Synthetic

<400> SEQUENCE: 172

Gln Gly Ile Ser Ser Trp
 1               5

<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173 actgcatcc                                                               9

<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174

Thr Ala Ser
 1

<210> SEQ ID NO 175
<211> LENGTH: 27
<212> TYPE: DNA
<213> ORGANISM: Artificial Sequence
<220> FEATURE:
<223> OTHER INFORMATION: Synthetic

<400> SEQUENCE: 175
caacagacta acagtctccc actcact                                          27

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

Gln Gln Thr Asn Ser Leu Pro Leu Thr

<210> SEQ ID NO 177
<211> LENGTH: 372
<212> TYPE: DNA
<213> ORGANISM: Artificial Sequence
<220> FEATURE:
<223> OTHER INFORMATION: Synthetic

<400> SEQUENCE: 177

```
gaggtgcagc tggtggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagtt attagtggta gtggtggtag cacatactac     180
gcagactccg tgaagggccg gttcaccatc tccagagaca attccaagaa cacgctgtat     240
ctacaaatga acagcctgag agccgaggac acggccgttt attactgtgc gaaaccctca     300
tcttatagca gctcgaactt ctactacggt atggacgtct ggggccaagg gaccacggtc     360
accgtctcct ca                                                         372
```

<210> SEQ ID NO 178
<211> LENGTH: 124
<212> TYPE: PRT
<213> ORGANISM: Artificial Sequence
<220> FEATURE:
<223> OTHER INFORMATION: Synthetic

<400> SEQUENCE: 178

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ser Ser Tyr Ser Ser Ser Asn Phe Tyr Tyr Gly Met Asp
            100                 105                 110

Val Trp Gly Gln Gly Thr Thr Val Thr Val Ser Ser
        115                 120

<210> SEQ ID NO 179
<211> LENGTH: 24
<212> TYPE: DNA
<213> ORGANISM: Artificial Sequence
<220> FEATURE:
<223> OTHER INFORMATION: Synthetic

<400> SEQUENCE: 179

```
ggattcacct ttagcagcta tgcc                                             24
```

<210> SEQ ID NO 180
<211> LENGTH: 8
<212> TYPE: PRT
<213> ORGANISM: Artificial Sequence
<220> FEATURE:
<223> OTHER INFORMATION: Synthetic

<400> SEQUENCE: 180

Gly Phe Thr Phe Ser Ser Tyr Ala
1               5

<210> SEQ ID NO 181
<211> LENGTH: 24
<212> TYPE: DNA
<213> ORGANISM: Artificial Sequence
<220> FEATURE:
<223> OTHER INFORMATION: Synthetic

<400> SEQUENCE: 181
attagtggta gtggtggtag caca                                          24

<210> SEQ ID NO 182
<211> LENGTH: 8
<212> TYPE: PRT
<213> ORGANISM: Artificial Sequence
<220> FEATURE:
<223> OTHER INFORMATION: Synthetic

<400> SEQUENCE: 182

Ile Ser Gly Ser Gly Gly Ser Thr
1               5

<210> SEQ ID NO 183
<211> LENGTH: 51
<212> TYPE: DNA
<213> ORGANISM: Artificial Sequence
<220> FEATURE:
<223> OTHER INFORMATION: Synthetic

<400> SEQUENCE: 183
gcgaaaccct catcttatag cagctcgaac ttctactacg gtatggacgt c            51

<210> SEQ ID NO 184
<211> LENGTH: 17
<212> TYPE: PRT
<213> ORGANISM: Artificial Sequence
<220> FEATURE:
<223> OTHER INFORMATION: Synthetic

<400> SEQUENCE: 184

Ala Lys Pro Ser Ser Tyr Ser Ser Ser Asn Phe Tyr Tyr Gly Met Asp
1               5                   10                  15
Val

<210> SEQ ID NO 185
<211> LENGTH: 321
<212> TYPE: DNA
<213> ORGANISM: Artificial Sequence
<220> FEATURE:
<223> OTHER INFORMATION: Synthetic

<400> SEQUENCE: 185
gacatcgtga tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct gatctatgct gcatccagtt tgcgaagtgg ggtcccatca   180
aggttcagcg gcagtggatc tgggacagat ttcactctca ccatcaccag cctgcagcct   240
gaagattttg caacttacta ttgtcaacac actaacagtt tcccattcac tttcggccct   300
gggaccaagg tggagatcaa a                                             321

<210> SEQ ID NO 186
<211> LENGTH: 107
<212> TYPE: PRT
<213> ORGANISM: Artificial Sequence
<220> FEATURE:
<223> OTHER INFORMATION: Synthetic

<400> SEQUENCE: 186

Asp Ile Val Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Arg Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Phe Ala Thr Tyr Tyr Cys Gln His Thr Asn Ser Phe Pro Phe
                85                  90                  95

Thr Phe Gly Pro Gly Thr Lys Val Glu Ile Lys
            100                 105

<210> SEQ ID NO 187
<211> LENGTH: 18
<212> TYPE: DNA
<213> ORGANISM: Artificial Sequence
<220> FEATURE:
<223> OTHER INFORMATION: Synthetic

<400> SEQUENCE: 187
cagggtatta gcagctgg                                                 18

<210> SEQ ID NO 188
<211> LENGTH: 6
<212> TYPE: PRT
<213> ORGANISM: Artificial Sequence
<220> FEATURE:
<223> OTHER INFORMATION: Synthetic

<400> SEQUENCE: 188

Gln Gly Ile Ser Ser Trp
1               5

<210> SEQ ID NO 189
<211> LENGTH: 9
<212> TYPE: DNA
<213> ORGANISM: Artificial Sequence
<220> FEATURE:
<223> OTHER INFORMATION: Synthetic

<400> SEQUENCE: 189 gctgcatcc                                                            9

<210> SEQ ID NO 190
<211> LENGTH: 3
<212> TYPE: PRT
<213> ORGANISM: Artificial Sequence
<220> FEATURE:
<223> OTHER INFORMATION: Synthetic

<400> SEQUENCE: 190

Ala Ala Ser
 1

<210> SEQ ID NO 191
<211> LENGTH: 27
<212> TYPE: DNA
<213> ORGANISM: Artificial Sequence
<220> FEATURE:
<223> OTHER INFORMATION: Synthetic

<400> SEQUENCE: 191
caacacacta acagtttccc attcact                                         27

<210> SEQ ID NO 192
<211> LENGTH: 9
<212> TYPE: PRT
<213> ORGANISM: Artificial Sequence
<220> FEATURE:
<223> OTHER INFORMATION: Synthetic

<400> SEQUENCE: 192

Gln His Thr Asn Ser Phe Pro Phe Thr
 1               5

<210> SEQ ID NO 193
<211> LENGTH: 369
<212> TYPE: DNA
<213> ORGANISM: Artificial Sequence
<220> FEATURE:
<223> OTHER INFORMATION: Synthetic

<400> SEQUENCE: 193
gaggtgcagc tggtggagtc tgggctgag gtgaagaagt ctgggtcctc ggtgaaggtc       60
tcctgcaagg cttctggagg caccttcagc cgctatgcta tcagctgggt gcgacaggcc     120
cctggacaag ggcttgagtg gatgggaggg atcatccctc tctttggtac attaaactac    180
gcacagaagt tccagggcag agtcacgctt accacggacg aatcaacgag cacagcctac    240
atggagctga gcagcctgag atctgaggac acggccgtgt attactgtgc ggtattttac    300
tatggttcgg ggagttatcg caactggttc gaccccctggg gccagggaac cctggtcacc    360
gtctcctca                                                            369

<210> SEQ ID NO 194
<211> LENGTH: 123
<212> TYPE: PRT
<213> ORGANISM: Artificial Sequence
<220> FEATURE:
<223> OTHER INFORMATION: Synthetic

<400> SEQUENCE: 194

Glu Val Gln Leu Val Glu Ser Gly Ala Glu Val Lys Lys Ser Gly Ser
 1               5                  10                  15

Ser Val Lys Val Ser Cys Lys Ala Ser Gly Gly Thr Phe Ser Arg Tyr
                20                  25                  30

Ala Ile Ser Trp Val Arg Gln Ala Pro Gly Gln Gly Leu Glu Trp Met
            35                  40                  45

Gly Gly Ile Ile Pro Leu Phe Gly Thr Leu Asn Tyr Ala Gln Lys Phe
        50                  55                  60

Gln Gly Arg Val Thr Leu Thr Thr Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Val Phe Tyr Tyr Gly Ser Gly Ser Tyr Arg Asn Trp Phe Asp Pro
            100                 105                 110

Trp Gly Gln Gly Thr Leu Val Thr Val Ser Ser
        115                 120

<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195
ggaggcacct tcagccgcta tgct                                          24

<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

Gly Gly Thr Phe Ser Arg Tyr Ala
1               5

<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197
atcatccctc tctttggtac atta                                          24

<210> SEQ ID NO 198
<211> LENGTH: 8
<212> TYPE: PRT
<213> ORGANISM: Artificial Sequence
<220> FEATURE:
<223> OTHER INFORMATION: Synthetic

<400> SEQUENCE: 198

Ile Ile Pro Leu Phe Gly Thr Leu
1               5

<210> SEQ ID NO 199
<211> LENGTH: 48
<212> TYPE: DNA
<213> ORGANISM: Artificial Sequence
<220> FEATURE:
<223> OTHER INFORMATION: Synthetic

<400> SEQUENCE: 199
gcggtatttt actatggttc ggggagttat cgcaactggt tcgacccc                48

<210> SEQ ID NO 200
<211> LENGTH: 16
<212> TYPE: PRT
<213> ORGANISM: Artificial Sequence
<220> FEATURE:
<223> OTHER INFORMATION: Synthetic

<400> SEQUENCE: 200

Ala Val Phe Tyr Tyr Gly Ser Gly Ser Tyr Arg Asn Trp Phe Asp Pro
1               5                   10                  15

<210> SEQ ID NO 201
<211> LENGTH: 321
<212> TYPE: DNA
<213> ORGANISM: Artificial Sequence
<220> FEATURE:
<223> OTHER INFORMATION: Synthetic

<400> SEQUENCE: 201
gacatccaga tgacccagtc tccatcctcc ctgtctgcat ctgtaggaga cagagtcacc      60
atcacttgcc gggcaagtca gagcatcagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacca ctgtcaacag agttacagta tcccgatcac cttcggccaa    300
gggacacgac tggagattaa a                                              321

<210> SEQ ID NO 202
<211> LENGTH: 107
<212> TYPE: PRT
<213> ORGANISM: Artificial Sequence
<220> FEATURE:
<223> OTHER INFORMATION: Synthetic

<400> SEQUENCE: 202

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr His Cys Gln Gln Ser Tyr Ser Ile Pro Ile
                85                  90                  95

Thr Phe Gly Gln Gly Thr Arg Leu Glu Ile Lys
            100                 105

<210> SEQ ID NO 203
<211> LENGTH: 18
<212> TYPE: DNA
<213> ORGANISM: Artificial Sequence
<220> FEATURE:
<223> OTHER INFORMATION: Synthetic

<400> SEQUENCE: 203
cagagcatca gcagctat                                                   18

<210> SEQ ID NO 204
<211> LENGTH: 6
<212> TYPE: PRT
<213> ORGANISM: Artificial Sequence
<220> FEATURE:
<223> OTHER INFORMATION: Synthetic

<400> SEQUENCE: 204

Gln Ser Ile Ser Ser Tyr

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 gctgcatcc                                                                9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Ala Ala Ser
 1

<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207
caacagagtt acagtatccc gatcacc                                           27

<210> SEQ ID NO 208
<211> LENGTH: 9
<212> TYPE: PRT
<213> ORGANISM: Artificial Sequence
<220> FEATURE:
<223> OTHER INFORMATION: Synthetic

<400> SEQUENCE: 208

Gln Gln Ser Tyr Ser Ile Pro Ile Thr
 1               5

<210> SEQ ID NO 209
<211> LENGTH: 357
<212> TYPE: DNA
<213> ORGANISM: Artificial Sequence
<220> FEATURE:
<223> OTHER INFORMATION: Synthetic

<400> SEQUENCE: 209
gaggtgcagc tgttggagtc tgggggaggc ttggtacagc ctggggggtc cctgagactc        60
tcctgtgcag cctctggatt caccttagc acctatgcca tgagctgggt ccgccaggct       120
ccagggaagg ggctggaatg ggtctcagct attcgtggta atggtgttaa cacatactac       180
ggagactcca tgaagggccg tttcaccatc tccagagaca attccaagga cacgctgtat       240
ttgcaaatga acagcctgag agccgaggac acggccgtat attactgtgc gaaaaataaa       300
tgggagctgc tagtctttga atactgggc cagggaaccc tggtcaccgt ctcctca         357

<210> SEQ ID NO 210
<211> LENGTH: 119
<212> TYPE: PRT
<213> ORGANISM: Artificial Sequence
<220> FEATURE:
<223> OTHER INFORMATION: Synthetic

<400> SEQUENCE: 210

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Ala Ile Arg Gly Asn Gly Val Asn Thr Tyr Tyr Gly Asp Ser Met
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Lys Trp Glu Leu Leu Val Phe Glu Tyr Trp Gly Gln Gly
            100                 105                 110

Thr Leu Val Thr Val Ser Ser
        115

<210> SEQ ID NO 211
<211> LENGTH: 24
<212> TYPE: DNA
<213> ORGANISM: Artificial Sequence
<220> FEATURE:
<223> OTHER INFORMATION: Synthetic

<400> SEQUENCE: 211
ggattcacct ttagcaccta tgcc                                        24

<210> SEQ ID NO 212
<211> LENGTH: 8
<212> TYPE: PRT
<213> ORGANISM: Artificial Sequence
<220> FEATURE:
<223> OTHER INFORMATION: Synthetic

<400> SEQUENCE: 212

Gly Phe Thr Phe Ser Thr Tyr Ala
1               5

<210> SEQ ID NO 213
<211> LENGTH: 24
<212> TYPE: DNA
<213> ORGANISM: Artificial Sequence
<220> FEATURE:
<223> OTHER INFORMATION: Synthetic

<400> SEQUENCE: 213
attcgtggta atggtgttaa caca                                        24

<210> SEQ ID NO 214
<211> LENGTH: 8
<212> TYPE: PRT
<213> ORGANISM: Artificial Sequence
<220> FEATURE:
<223> OTHER INFORMATION: Synthetic

<400> SEQUENCE: 214

Ile Arg Gly Asn Gly Val Asn Thr
1               5

<210> SEQ ID NO 215
<211> LENGTH: 36
<212> TYPE: DNA
<213> ORGANISM: Artificial Sequence
<220> FEATURE:
<223> OTHER INFORMATION: Synthetic

<400> SEQUENCE: 215
gcgaaaaata aatgggagct gctagtcttt gaatac                                   36

<210> SEQ ID NO 216
<211> LENGTH: 12
<212> TYPE: PRT
<213> ORGANISM: Artificial Sequence
<220> FEATURE:
<223> OTHER INFORMATION: Synthetic

<400> SEQUENCE: 216

Ala Lys Asn Lys Trp Glu Leu Leu Val Phe Glu Tyr
 1               5                  10

<210> SEQ ID NO 217
<211> LENGTH: 318
<212> TYPE: DNA
<213> ORGANISM: Artificial Sequence
<220> FEATURE:
<223> OTHER INFORMATION: Synthetic

<400> SEQUENCE: 217
gacatccaga tgacccagtc tccatcctcc ctgtctgcat ctgtaggaga cagagtcacc          60
atcacttgcc gggcgagtca ggacattagc aattatttag cctggtatca gcagaaacca        120
gggaaagttc ctaagctcct gatctatgct gcatccactt tgcaatcagg ggtcccattt        180
cggttcagtg gcagtggatc tgggacagat ttcactctca ccatcagcag cctgcagcct        240
gaagatgttg caacttatta ctgtcaaaag tataacagtg cccctccttt cggccctggg        300
accaaagtgg atatcaaa                                                      318

<210> SEQ ID NO 218
<211> LENGTH: 106
<212> TYPE: PRT
<213> ORGANISM: Artificial Sequence
<220> FEATURE:
<223> OTHER INFORMATION: Synthetic

<400> SEQUENCE: 218

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
             20                  25                  30

Leu Ala Trp Tyr Gln Gln Lys Pro Gly Lys Val Pro Lys Leu Leu Ile
         35                  40                  45

Tyr Ala Ala Ser Thr Leu Gln Ser Gly Val Pro Phe Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro Pro
                 85                  90                  95

Phe Gly Pro Gly Thr Lys Val Asp Ile Lys
            100                 105

```
<210> SEQ ID NO 219
<211> LENGTH: 18
<212> TYPE: DNA
<213> ORGANISM: Artificial Sequence
<220> FEATURE:
<223> OTHER INFORMATION: Synthetic

<400> SEQUENCE: 219
caggacatta gcaattat                                                 18

<210> SEQ ID NO 220
<211> LENGTH: 6
<212> TYPE: PRT
<213> ORGANISM: Artificial Sequence
<220> FEATURE:
<223> OTHER INFORMATION: Synthetic

<400> SEQUENCE: 220

Gln Asp Ile Ser Asn Tyr
  1               5

<210> SEQ ID NO 221
<211> LENGTH: 9
<212> TYPE: DNA
<213> ORGANISM: Artificial Sequence
<220> FEATURE:
<223> OTHER INFORMATION: Synthetic

<400> SEQUENCE: 221 gctgcatcc                                                            9

<210> SEQ ID NO 222
<211> LENGTH: 3
<212> TYPE: PRT
<213> ORGANISM: Artificial Sequence
<220> FEATURE:
<223> OTHER INFORMATION: Synthetic

<400> SEQUENCE: 222

Ala Ala Ser
  1

<210> SEQ ID NO 223
<211> LENGTH: 24
<212> TYPE: DNA
<213> ORGANISM: Artificial Sequence
<220> FEATURE:
<223> OTHER INFORMATION: Synthetic

<400> SEQUENCE: 223
caaaagtata acagtgcccc tcct                                          24

<210> SEQ ID NO 224
<211> LENGTH: 8
<212> TYPE: PRT
<213> ORGANISM: Artificial Sequence
<220> FEATURE:
<223> OTHER INFORMATION: Synthetic

<400> SEQUENCE: 224

Gln Lys Tyr Asn Ser Ala Pro Pro
  1               5

<210> SEQ ID NO 225
<211> LENGTH: 363
<212> TYPE: DNA
<213> ORGANISM: Artificial Sequence
```

-continued

```
<220> FEATURE:
<223> OTHER INFORMATION: Synthetic

<400> SEQUENCE: 225
gaggtgcagc tggtggagtc tgggggaggc gtggtccagc ctgggaggtc cctgagactc    60
tcctgtgcag cgtctggatt cagtttcagt gactatgtca tgcactgggt ccgccaggct   120
ccaggcaagg ggctggagtg ggtggcatct atatggtttg atggaagtaa tgaattctat   180
gcagactccg tgaagggccg attcaccatc tccagagaca attccaagaa cacgctgttt   240
ctgcaaatga acagtctgag agccgaggac acggctgtgt attactgtgc gaaaaaggga   300
gtgttggtag ctacctctgc ttttgatatc tggggccaag ggacaatggt caccgtctct   360
tca                                                                 363

<210> SEQ ID NO 226
<211> LENGTH: 121
<212> TYPE: PRT
<213> ORGANISM: Artificial Sequence
<220> FEATURE:
<223> OTHER INFORMATION: Synthetic

<400> SEQUENCE: 226

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Ser Phe Ser Asp Tyr
            20                  25                  30

Val Met His Trp Val Arg Gln Ala Pro Gly Lys Gly Leu Glu Trp Val
        35                  40                  45

Ala Ser Ile Trp Phe Asp Gly Ser Asn Glu Phe Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Lys Gly Val Leu Val Ala Thr Ser Ala Phe Asp Ile Trp Gly
            100                 105                 110

Gln Gly Thr Met Val Thr Val Ser Ser
        115                 120

<210> SEQ ID NO 227
<211> LENGTH: 24
<212> TYPE: DNA
<213> ORGANISM: Artificial Sequence
<220> FEATURE:
<223> OTHER INFORMATION: Synthetic

<400> SEQUENCE: 227
ggattcagtt tcagtgacta tgtc                                           24

<210> SEQ ID NO 228
<211> LENGTH: 8
<212> TYPE: PRT
<213> ORGANISM: Artificial Sequence
<220> FEATURE:
<223> OTHER INFORMATION: Synthetic

<400> SEQUENCE: 228

Gly Phe Ser Phe Ser Asp Tyr Val
 1               5
```

```
<210> SEQ ID NO 229
<211> LENGTH: 24
<212> TYPE: DNA
<213> ORGANISM: Artificial Sequence
<220> FEATURE:
<223> OTHER INFORMATION: Synthetic

<400> SEQUENCE: 229
atatggtttg atggaagtaa tgaa                                            24

<210> SEQ ID NO 230
<211> LENGTH: 8
<212> TYPE: PRT
<213> ORGANISM: Artificial Sequence
<220> FEATURE:
<223> OTHER INFORMATION: Synthetic

<400> SEQUENCE: 230

Ile Trp Phe Asp Gly Ser Asn Glu
 1               5

<210> SEQ ID NO 231
<211> LENGTH: 42
<212> TYPE: DNA
<213> ORGANISM: Artificial Sequence
<220> FEATURE:
<223> OTHER INFORMATION: Synthetic

<400> SEQUENCE: 231
gcgaaaaagg gagtgttggt agctacctct gcttttgata tc                        42

<210> SEQ ID NO 232
<211> LENGTH: 14
<212> TYPE: PRT
<213> ORGANISM: Artificial Sequence
<220> FEATURE:
<223> OTHER INFORMATION: Synthetic

<400> SEQUENCE: 232

Ala Lys Lys Gly Val Leu Val Ala Thr Ser Ala Phe Asp Ile
 1               5                  10

<210> SEQ ID NO 233
<211> LENGTH: 324
<212> TYPE: DNA
<213> ORGANISM: Artificial Sequence
<220> FEATURE:
<223> OTHER INFORMATION: Synthetic

<400> SEQUENCE: 233
gacatccaga tgacccagtc tccatcctcc ctgtctgcat ctgtaggaga cagagtcacc     60
atcacttgcc gggcaagtca gagcattaac aactatttaa attggtatca tcagaaacca    120
gggaaagccc ctaagctcct aatctatgct gcatccagtt tgcaaagtgg ggtcccatca    180
aggttcagtg gcagtggatc tgggacagat tacactctca ccatcagcag tctgcaacct    240
gaagattttg gaaattacta ctgtcaacag agttacagaa cttccatgta cacttttggc    300
caggggacca aggtggaaat caaa                                           324

<210> SEQ ID NO 234
<211> LENGTH: 108
<212> TYPE: PRT
<213> ORGANISM: Artificial Sequence
<220> FEATURE:
<223> OTHER INFORMATION: Synthetic
```

-continued

<400> SEQUENCE: 234

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Tyr
            20                  25                  30

Leu Asn Trp Tyr His Gln Lys Pro Gly Lys Ala Pro Lys Leu Leu Ile
        35                  40                  45

Tyr Ala Ala Ser Leu Gln Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Gly Asn Tyr Tyr Cys Gln Gln Ser Tyr Arg Thr Ser Met
                85                  90                  95

Tyr Thr Phe Gly Gln Gly Thr Lys Val Glu Ile Lys
            100                 105

<210> SEQ ID NO 235
<211> LENGTH: 18
<212> TYPE: DNA
<213> ORGANISM: Artificial Sequence
<220> FEATURE:
<223> OTHER INFORMATION: Synthetic

<400> SEQUENCE: 235
cagagcatta acaactat                                                        18

<210> SEQ ID NO 236
<211> LENGTH: 6
<212> TYPE: PRT
<213> ORGANISM: Artificial Sequence
<220> FEATURE:
<223> OTHER INFORMATION: Synthetic

<400> SEQUENCE: 236

Gln Ser Ile Asn Asn Tyr
1               5

<210> SEQ ID NO 237
<211> LENGTH: 9
<212> TYPE: DNA
<213> ORGANISM: Artificial Sequence
<220> FEATURE:
<223> OTHER INFORMATION: Synthetic

<400> SEQUENCE: 237 gctgcatcc                                                                   9

<210> SEQ ID NO 238
<211> LENGTH: 3
<212> TYPE: PRT
<213> ORGANISM: Artificial Sequence
<220> FEATURE:
<223> OTHER INFORMATION: Synthetic

<400> SEQUENCE: 238

Ala Ala Ser
1

<210> SEQ ID NO 239
<211> LENGTH: 30
<212> TYPE: DNA
<213> ORGANISM: Artificial Sequence
<220> FEATURE:

<223> OTHER INFORMATION: Synthetic

<400> SEQUENCE: 239
caacagagtt acagaacttc catgtacact                                              30

<210> SEQ ID NO 240
<211> LENGTH: 10
<212> TYPE: PRT
<213> ORGANISM: Artificial Sequence
<220> FEATURE:
<223> OTHER INFORMATION: Synthetic

<400> SEQUENCE: 240

Gln Gln Ser Tyr Arg Thr Ser Met Tyr Thr
1               5                   10

<210> SEQ ID NO 241
<211> LENGTH: 360
<212> TYPE: DNA
<213> ORGANISM: Artificial Sequence
<220> FEATURE:
<223> OTHER INFORMATION: Synthetic

<400> SEQUENCE: 241
gaggtgcagc tggtggagtc tgggggaggc ttggtacggc ctggcaggtc cctgagactc         60
tcctgtgcag cctctggatt cacctttgat aattatgcca tgcactgggt ccggcaagtt        120
ccagggaagg gcctggagtg ggtctcaggt attacttgga atagtgttag cctaggctat        180
gcggactctg tgaagggccg attcaccatc tccagagaca cgcccagaa ctccctgtat         240 ctgcaaatga acagtctgag aactgtggac acggccttgt attactgtgc aaaagatagg        300
tggggtggaa gttactactt tgacttctgg ggccagggaa ccctggtcac cgtctcctca        360

<210> SEQ ID NO 242
<211> LENGTH: 120
<212> TYPE: PRT
<213> ORGANISM: Artificial Sequence
<220> FEATURE:
<223> OTHER INFORMATION: Synthetic

<400> SEQUENCE: 242

Glu Val Gln Leu Val Glu Ser Gly Gly Gly Leu Val Arg Pro Gly Arg
1               5                   10                  15

Ser Leu Arg Leu Ser Cys Ala Ala Ser Gly Phe Thr Phe Asp Asn Tyr
                20                  25                  30

Ala Met His Trp Val Arg Gln Val Pro Gly Lys Gly Leu Glu Trp Val
            35                  40                  45

Ser Gly Ile Thr Trp Asn Ser Val Ser Leu Gly Tyr Ala Asp Ser Val
        50                  55                  60

Lys Gly Arg Phe Thr Ile Ser Arg Asp Asn Ala Gln Asn Ser Leu Tyr
65                  70                  75                  80

Leu Gln Met Asn Ser Leu Arg Thr Val Asp Thr Ala Leu Tyr Tyr Cys
                85                  90                  95

Ala Lys Asp Arg Trp Gly Gly Ser Tyr Tyr Phe Asp Phe Trp Gly Gln
            100                 105                 110

Gly Thr Leu Val Thr Val Ser Ser
        115                 120

<210> SEQ ID NO 243
<211> LENGTH: 24
<212> TYPE: DNA

```
<213> ORGANISM: Artificial Sequence
<220> FEATURE:
<223> OTHER INFORMATION: Synthetic

<400> SEQUENCE: 243
ggattcacct ttgataatta tgcc                                              24

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

Gly Phe Thr Phe Asp Asn Tyr Ala
 1               5

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245
attacttgga atagtgttag ccta                                              24

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Ile Thr Trp Asn Ser Val Ser Leu
 1               5

<210> SEQ ID NO 247
<211> LENGTH: 39
<212> TYPE: DNA
<213> ORGANISM: Artificial Sequence
<220> FEATURE:
<223> OTHER INFORMATION: Synthetic

<400> SEQUENCE: 247
gcaaaagata ggtggggtgg aagttactac tttgacttc                              39

<210> SEQ ID NO 248
<211> LENGTH: 13
<212> TYPE: PRT
<213> ORGANISM: Artificial Sequence
<220> FEATURE:
<223> OTHER INFORMATION: Synthetic

<400> SEQUENCE: 248

Ala Lys Asp Arg Trp Gly Gly Ser Tyr Tyr Phe Asp Phe
 1               5                  10

<210> SEQ ID NO 249
<211> LENGTH: 318
<212> TYPE: DNA
<213> ORGANISM: Artificial Sequence
<220> FEATURE:
<223> OTHER INFORMATION: Synthetic
```

-continued

<400> SEQUENCE: 249

```
gacatcgtga tgacccagtc tccatcctcc ctgtctgcat ctgtaggaga cagagtcacc    60
atcacttgcc gggcgagtca gggcattagc aattatttag cctggtatca gcagaaacca   120
gggaaagttc ctaaactcct gatctattct gcatccactt tgcaatcagg ggtcccatct   180
cggttcagtg gcagtggatc tgggacagat ttcactctca ccatcagcaa cctgcagcct   240
gaagattttg caacttttttt ctgtcaaaag tataacagtg cccccacttt cggcggaggg   300
accaaggtgg agatcaaa                                                 318
```

<210> SEQ ID NO 250
<211> LENGTH: 106
<212> TYPE: PRT
<213> ORGANISM: Artificial Sequence
<220> FEATURE:
<223> OTHER INFORMATION: Synthetic

<400> SEQUENCE: 250

Asp Ile Val Met Thr Gln Ser Pro Ser Ser Leu Ser Ala Ser Val Gly
1               5                   10                  15
Asp Arg Val Thr Ile Thr Cys Arg Ala Ser Gln Gly Ile Ser Asn Tyr
            20                  25                  30
Leu Ala Trp Tyr Gln Gln Lys Pro Gly Lys Val Pro Lys Leu Leu Ile
        35                  40                  45
Tyr Ser Ala Ser Thr Leu Gln Ser Gly Val Pro Ser Arg Phe Ser Gly
    50                  55                  60
Ser Gly Ser Gly Thr Asp Phe Thr Leu Thr Ile Ser Asn Leu Gln Pro
65                  70                  75                  80
Glu Asp Phe Ala Thr Phe Phe Cys Gln Lys Tyr Asn Ser Ala Pro Thr
                85                  90                  95
Phe Gly Gly Gly Thr Lys Val Glu Ile Lys
            100                 105

<210> SEQ ID NO 251
<211> LENGTH: 18
<212> TYPE: DNA
<213> ORGANISM: Artificial Sequence
<220> FEATURE:
<223> OTHER INFORMATION: Synthetic

<400> SEQUENCE: 251
cagggcatta gcaattat                                                  18

<210> SEQ ID NO 252
<211> LENGTH: 6
<212> TYPE: PRT
<213> ORGANISM: Artificial Sequence
<220> FEATURE:
<223> OTHER INFORMATION: Synthetic

<400> SEQUENCE: 252

Gln Gly Ile Ser Asn Tyr
1               5

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 tctgcatcc                                                                9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Ser Ala Ser
 1

<210> SEQ ID NO 255
<211> LENGTH: 24
<212> TYPE: DNA
<213> ORGANISM: Artificial Sequence
<220> FEATURE:
<223> OTHER INFORMATION: Synthetic

<400> SEQUENCE: 255
caaaagtata acagtgcccc cact                                              24

<210> SEQ ID NO 256
<211> LENGTH: 8
<212> TYPE: PRT
<213> ORGANISM: Artificial Sequence
<220> FEATURE:
<223> OTHER INFORMATION: Synthetic

<400> SEQUENCE: 256

Gln Lys Tyr Asn Ser Ala Pro Thr
 1               5

<210> SEQ ID NO 257
<211> LENGTH: 363
<212> TYPE: DNA
<213> ORGANISM: Artificial Sequence
<220> FEATURE:
<223> OTHER INFORMATION: Synthetic

<400> SEQUENCE: 257
caggtgcagc tggtggagtc tgggggaggc gtggtccagc ctgggaggtc cctgagactc        60
tcctgtgcag cgtctggatt cagtttcagt gactatgtca tgcactgggt ccgccaggct       120
ccaggcaagg ggctggagtg ggtggcatct atatggtttg atggaagtaa tgaattctat       180
gcagactccg tgaagggccg attcaccatc tccagagaca attccaagaa cacgctgttt       240
ctgcaaatga acagtctgag agccgaggac acggctgtgt attactgtgc gaaaaaggga       300
gtgttggtag ctacctctgc ttttgatatc tggggccaag ggacaatggt caccgtctct       360
tca                                                                    363

<210> SEQ ID NO 258
<211> LENGTH: 121
<212> TYPE: PRT
<213> ORGANISM: Artificial Sequence
<220> FEATURE:
<223> OTHER INFORMATION: Synthetic

<400> SEQUENCE: 258

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Ser Phe Ser Asp Tyr

```
                 20                  25                  30
Val Met His Trp Val Arg Gln Ala Pro Gly Lys Gly Leu Glu Trp Val
             35                  40                  45

Ala Ser Ile Trp Phe Asp Gly Ser Asn Glu Phe Tyr Ala Asp Ser Val
         50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Lys Lys Gly Val Leu Val Ala Thr Ser Ala Phe Asp Ile Trp Gly
            100                 105                 110

Gln Gly Thr Met Val Thr Val Ser Ser
            115                 120

<210> SEQ ID NO 259
<211> LENGTH: 24
<212> TYPE: DNA
<213> ORGANISM: Artificial Sequence
<220> FEATURE:
<223> OTHER INFORMATION: Synthetic

<400> SEQUENCE: 259
ggattcagtt tcagtgacta tgtc                                         24

<210> SEQ ID NO 260
<211> LENGTH: 8
<212> TYPE: PRT
<213> ORGANISM: Artificial Sequence
<220> FEATURE:
<223> OTHER INFORMATION: Synthetic

<400> SEQUENCE: 260

Gly Phe Ser Phe Ser Asp Tyr Val
 1               5

<210> SEQ ID NO 261
<211> LENGTH: 24
<212> TYPE: DNA
<213> ORGANISM: Artificial Sequence
<220> FEATURE:
<223> OTHER INFORMATION: Synthetic

<400> SEQUENCE: 261
atatggtttg atggaagtaa tgaa                                         24

<210> SEQ ID NO 262
<211> LENGTH: 8
<212> TYPE: PRT
<213> ORGANISM: Artificial Sequence
<220> FEATURE:
<223> OTHER INFORMATION: Synthetic

<400> SEQUENCE: 262

Ile Trp Phe Asp Gly Ser Asn Glu
 1               5

<210> SEQ ID NO 263
<211> LENGTH: 42
<212> TYPE: DNA
<213> ORGANISM: Artificial Sequence
<220> FEATURE:
<223> OTHER INFORMATION: Synthetic

<400> SEQUENCE: 263
```

```
gcgaaaaagg gagtgttggt agctacctct gcttttgata tc                    42
```

<210> SEQ ID NO 264
<211> LENGTH: 14
<212> TYPE: PRT
<213> ORGANISM: Artificial Sequence
<220> FEATURE:
<223> OTHER INFORMATION: Synthetic

<400> SEQUENCE: 264

Ala Lys Lys Gly Val Leu Val Ala Thr Ser Ala Phe Asp Ile
 1               5                  10

<210> SEQ ID NO 265
<211> LENGTH: 324
<212> TYPE: DNA
<213> ORGANISM: Artificial Sequence
<220> FEATURE:
<223> OTHER INFORMATION: Synthetic

<400> SEQUENCE: 265

```
gaaattgtga tgacgcagtc tccatcctcc ctgtctgcat ctgtaggaga cagagtcacc    60
atcacttgcc gggcaagtca gagcattaac aactatttaa attggtatca tcagaaacca   120
gggaaagccc ctaagctcct aatctatgct gcatccagtt tgcaaagtgg ggtcccatca   180
aggttcagtg gcagtggatc tgggacagat tacactctca ccatcagcag tctgcaacct   240
gaagattttg gaaattacta ctgtcaacag agttacagaa cttccatgta cacttttggc   300
caggggacca aggtggagat caaa                                          324
```

<210> SEQ ID NO 266
<211> LENGTH: 108
<212> TYPE: PRT
<213> ORGANISM: Artificial Sequence
<220> FEATURE:
<223> OTHER INFORMATION: Synthetic

<400> SEQUENCE: 266

Glu Ile Val Met Thr Gln Ser Pro Ser Ser Leu Ser Ala Ser Val Gly
 1               5                  10                  15

Asp Arg Val Thr Ile Thr Cys Arg Ala Ser Gln Ser Ile Asn Asn Tyr
            20                  25                  30

Leu Asn Trp Tyr His Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Gly Asn Tyr Tyr Cys Gln Gln Ser Tyr Arg Thr Ser Met
                85                  90                  95

Tyr Thr Phe Gly Gln Gly Thr Lys Val Glu Ile Lys
            100                 105

<210> SEQ ID NO 267
<211> LENGTH: 18
<212> TYPE: DNA
<213> ORGANISM: Artificial Sequence
<220> FEATURE:
<223> OTHER INFORMATION: Synthetic

<400> SEQUENCE: 267
cagagcatta acaactat                                              18

<210> SEQ ID NO 268
<211> LENGTH: 6
<212> TYPE: PRT
<213> ORGANISM: Artificial Sequence
<220> FEATURE:
<223> OTHER INFORMATION: Synthetic

<400> SEQUENCE: 268

Gln Ser Ile Asn Asn Tyr
 1               5

<210> SEQ ID NO 269
<211> LENGTH: 9
<212> TYPE: DNA
<213> ORGANISM: Artificial Sequence
<220> FEATURE:
<223> OTHER INFORMATION: Synthetic

<400> SEQUENCE: 269 gctgcatcc                                                         9

<210> SEQ ID NO 270
<211> LENGTH: 3
<212> TYPE: PRT
<213> ORGANISM: Artificial Sequence
<220> FEATURE:
<223> OTHER INFORMATION: Synthetic

<400> SEQUENCE: 270

Ala Ala Ser
 1

<210> SEQ ID NO 271
<211> LENGTH: 30
<212> TYPE: DNA
<213> ORGANISM: Artificial Sequence
<220> FEATURE:
<223> OTHER INFORMATION: Synthetic

<400> SEQUENCE: 271
caacagagtt acagaacttc catgtacact                                 30

<210> SEQ ID NO 272
<211> LENGTH: 10
<212> TYPE: PRT
<213> ORGANISM: Artificial Sequence
<220> FEATURE:
<223> OTHER INFORMATION: Synthetic

<400> SEQUENCE: 272

Gln Gln Ser Tyr Arg Thr Ser Met Tyr Thr
 1               5                  10

<210> SEQ ID NO 273
<211> LENGTH: 366
<212> TYPE: DNA
<213> ORGANISM: Artificial Sequence
<220> FEATURE:
<223> OTHER INFORMATION: Synthetic

<400> SEQUENCE: 273
caggtgcagc tgcaggagtc gggcccagga ctggtgaagc cttcggagac cctgtccctc    60
acctgcactg tctctggtgg ctccatcagt acttactact ggagctggtt ccggcagccc   120

-continued

```
ccagggaagg gactggagtg gattgggtat atctattaca gtgggagcac caaccacaac    180
ccctccctca agagtcgagt caccatatca gtagacacgt ccaagaacca gttctccctg    240
aaactgaggt ctgtgaccgc tgcggacacg gccgtgtatt actgtgcgag agtaggtccg    300
gtgggctggg gatcatgggg gaactttgac tactggggcc agggaaccct ggtcaccgtc    360
tcctca                                                              366
```

<210> SEQ ID NO 274
<211> LENGTH: 122
<212> TYPE: PRT
<213> ORGANISM: Artificial Sequence
<220> FEATURE:
<223> OTHER INFORMATION: Synthetic

<400> SEQUENCE: 274

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Thr Tyr
             20                  25                  30

Tyr Trp Ser Trp Phe Arg Gln Pro Pro Gly Lys Gly Leu Glu Trp Ile
         35                  40                  45

Gly Tyr Ile Tyr Tyr Ser Gly Ser Thr Asn His Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Arg Ser Val Thr Ala Ala Asp Thr Ala Val Tyr Tyr Cys Ala
                 85                  90                  95

Arg Val Gly Pro Val Gly Trp Gly Ser Trp Gly Asn Phe Asp Tyr Trp
            100                 105                 110

Gly Gln Gly Thr Leu Val Thr Val Ser Ser
            115                 120
```

<210> SEQ ID NO 275
<211> LENGTH: 24
<212> TYPE: DNA
<213> ORGANISM: Artificial Sequence
<220> FEATURE:
<223> OTHER INFORMATION: Synthetic

<400> SEQUENCE: 275

```
ggtggctcca tcagtactta ctac                                           24
```

<210> SEQ ID NO 276
<211> LENGTH: 8
<212> TYPE: PRT
<213> ORGANISM: Artificial Sequence
<220> FEATURE:
<223> OTHER INFORMATION: Synthetic

<400> SEQUENCE: 276

```
Gly Gly Ser Ile Ser Thr Tyr Tyr
  1               5
```

<210> SEQ ID NO 277
<211> LENGTH: 21
<212> TYPE: DNA
<213> ORGANISM: Artificial Sequence
<220> FEATURE:
<223> OTHER INFORMATION: Synthetic

<400> SEQUENCE: 277

```
atctattaca gtgggagcac c                                              21
```

<210> SEQ ID NO 278
<211> LENGTH: 7
<212> TYPE: PRT
<213> ORGANISM: Artificial Sequence
<220> FEATURE:
<223> OTHER INFORMATION: Synthetic

<400> SEQUENCE: 278

Ile Tyr Tyr Ser Gly Ser Thr
 1               5

<210> SEQ ID NO 279
<211> LENGTH: 48
<212> TYPE: DNA
<213> ORGANISM: Artificial Sequence
<220> FEATURE:
<223> OTHER INFORMATION: Synthetic

<400> SEQUENCE: 279

```
gcgagagtag gtccggtggg ctggggatca tgggggaact ttgactac                 48
```

<210> SEQ ID NO 280
<211> LENGTH: 16
<212> TYPE: PRT
<213> ORGANISM: Artificial Sequence
<220> FEATURE:
<223> OTHER INFORMATION: Synthetic

<400> SEQUENCE: 280

Ala Arg Val Gly Pro Val Gly Trp Gly Ser Trp Gly Asn Phe Asp Tyr
 1               5                  10                  15

<210> SEQ ID NO 281
<211> LENGTH: 321
<212> TYPE: DNA
<213> ORGANISM: Artificial Sequence
<220> FEATURE:
<223> OTHER INFORMATION: Synthetic

<400> SEQUENCE: 281

```
gacatccagt tgacccagtc tccatccttc ctgtctgcat ctgtaggaga cagagtcacc    60
atcacttgct gggccagtca gggcattagc agttatttag cctggtctca gcaaaaacca   120
gggaaagccc ctaagctcct gatctatgct gcatccactt tacaaagtgg ggtcccatca   180
aggttcagcg gcagtggatc tgggacagaa ttcactctca caatcagcag cctgcagcct   240
gaagattttg caacttatta ctgtcaacag cttaatagtt acccgtggac gttcggccaa   300
gggaccaagg tggagatcaa a                                             321
```

<210> SEQ ID NO 282
<211> LENGTH: 107
<212> TYPE: PRT
<213> ORGANISM: Artificial Sequence
<220> FEATURE:
<223> OTHER INFORMATION: Synthetic

<400> SEQUENCE: 282

Asp Ile Gln Leu Thr Gln Ser Pro Ser Phe Leu Ser Ala Ser Val Gly
 1               5                  10                  15

Asp Arg Val Thr Ile Thr Cys Trp Ala Ser Gln Gly Ile Ser Ser Tyr
                20                  25                  30

Leu Ala Trp Ser Gln Gln Lys Pro Gly Lys Ala Pro Lys Leu Leu Ile 35                  40                  45
Tyr Ala Ala Ser Thr Leu Gln Ser Gly Val Pro Ser Arg Phe Ser Gly
         50                  55                  60
Ser Gly Ser Gly Thr Glu Phe Thr Leu Thr Ile Ser Ser Leu Gln Pro
 65                  70                  75                  80
Glu Asp Phe Ala Thr Tyr Tyr Cys Gln Gln Leu Asn Ser Tyr Pro Trp
                 85                  90                  95
Thr Phe Gly Gln Gly Thr Lys Val Glu Ile Lys
            100                 105

<210> SEQ ID NO 283
<211> LENGTH: 18
<212> TYPE: DNA
<213> ORGANISM: Artificial Sequence
<220> FEATURE:
<223> OTHER INFORMATION: Synthetic

<400> SEQUENCE: 283
cagggcatta gcagttat                                                   18

<210> SEQ ID NO 284
<211> LENGTH: 6
<212> TYPE: PRT
<213> ORGANISM: Artificial Sequence
<220> FEATURE:
<223> OTHER INFORMATION: Synthetic

<400> SEQUENCE: 284

Gln Gly Ile Ser Ser Tyr
 1               5

<210> SEQ ID NO 285
<211> LENGTH: 9
<212> TYPE: DNA
<213> ORGANISM: Artificial Sequence
<220> FEATURE:
<223> OTHER INFORMATION: Synthetic

<400> SEQUENCE: 285 gctgcatcc                                                              9

<210> SEQ ID NO 286
<211> LENGTH: 3
<212> TYPE: PRT
<213> ORGANISM: Artificial Sequence
<220> FEATURE:
<223> OTHER INFORMATION: Synthetic

<400> SEQUENCE: 286

Ala Ala Ser
 1

<210> SEQ ID NO 287
<211> LENGTH: 27
<212> TYPE: DNA
<213> ORGANISM: Artificial Sequence
<220> FEATURE:
<223> OTHER INFORMATION: Synthetic

<400> SEQUENCE: 287
caacagctta atagttaccc gtggacg                                         27

<210> SEQ ID NO 288
<211> LENGTH: 9

```
<212> TYPE: PRT
<213> ORGANISM: Artificial Sequence
<220> FEATURE:
<223> OTHER INFORMATION: Synthetic

<400> SEQUENCE: 288

Gln Gln Leu Asn Ser Tyr Pro Trp Thr
 1               5

<210> SEQ ID NO 289
<211> LENGTH: 360
<212> TYPE: DNA
<213> ORGANISM: Artificial Sequence
<220> FEATURE:
<223> OTHER INFORMATION: Synthetic

<400> SEQUENCE: 289
gaggtgcagc tggtgcagtc tggagctgag gtgaagaagc ctggggcctc agtgaaggtc     60
tcctgcaagg cttctggtta cacctttacc aattatggta tcacctgggt gcgacaggcc    120
cctggacaag gcttgagtg gatggggtgg atcagcgctt acaatggtaa caccggctat    180
gcacagaaat tccagggcag agtcaccatg accacagaca cttccacgag cacagcctac    240
atggagctga ggagcctgag atctgacgac acggccgtgt attactgtgc gagagaggat    300
tacgattttt ggagggcttt tgatatctgg ggccaaggga caatggtcac cgtctcttca    360

<210> SEQ ID NO 290
<211> LENGTH: 120
<212> TYPE: PRT
<213> ORGANISM: Artificial Sequence
<220> FEATURE:
<223> OTHER INFORMATION: Synthetic

<400> SEQUENCE: 290

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
             20                  25                  30

Gly Ile Thr Trp Val Arg Gln Ala Pro Gly Gln Gly Leu Glu Trp Met
         35                  40                  45

Gly Trp Ile Ser Ala Tyr Asn Gly Asn Thr Gly Tyr Ala Gln Lys Phe
     50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Glu Asp Tyr Asp Phe Trp Arg Ala Phe Asp Ile Trp Gly Gln
            100                 105                 110

Gly Thr Met Val Thr Val Ser Ser
        115                 120

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291 ggttacaccct ttaccaatta tggt                                            24
```

-continued

<210> SEQ ID NO 292
<211> LENGTH: 8
<212> TYPE: PRT
<213> ORGANISM: Artificial Sequence
<220> FEATURE:
<223> OTHER INFORMATION: Synthetic

<400> SEQUENCE: 292

Gly Tyr Thr Phe Thr Asn Tyr Gly
1               5

<210> SEQ ID NO 293
<211> LENGTH: 24
<212> TYPE: DNA
<213> ORGANISM: Artificial Sequence
<220> FEATURE:
<223> OTHER INFORMATION: Synthetic

<400> SEQUENCE: 293
atcagcgctt acaatggtaa cacc                                          24

<210> SEQ ID NO 294
<211> LENGTH: 8
<212> TYPE: PRT
<213> ORGANISM: Artificial Sequence
<220> FEATURE:
<223> OTHER INFORMATION: Synthetic

<400> SEQUENCE: 294

Ile Ser Ala Tyr Asn Gly Asn Thr
1               5

<210> SEQ ID NO 295
<211> LENGTH: 39
<212> TYPE: DNA
<213> ORGANISM: Artificial Sequence
<220> FEATURE:
<223> OTHER INFORMATION: Synthetic

<400> SEQUENCE: 295
gcgagagagg attacgattt ttggagggct tttgatatc                          39

<210> SEQ ID NO 296
<211> LENGTH: 13
<212> TYPE: PRT
<213> ORGANISM: Artificial Sequence
<220> FEATURE:
<223> OTHER INFORMATION: Synthetic

<400> SEQUENCE: 296

Ala Arg Glu Asp Tyr Asp Phe Trp Arg Ala Phe Asp Ile
1               5                   10

<210> SEQ ID NO 297
<211> LENGTH: 324
<212> TYPE: DNA
<213> ORGANISM: Artificial Sequence
<220> FEATURE:
<223> OTHER INFORMATION: Synthetic

<400> SEQUENCE: 297
gaaattgtgc tgactcagtc tccaggcacc ctgtctttgt ctccggggga aagagccacc    60
ctctcctgca gggccagtca gagtgttagc agcacctact tagcctggct ccagcagaaa   120
cctggccagg ctcccaggct cctcatctat ggtgcatcca gcagggccac ggcatccca   180 gacaggttca gtggcagtgg gtctgggaca gacttcactc tcaccatcaa cagactggag   240
cctgaagatt ttgcagtgta ttattgtcaa cagtatgctt actcaccgta cacttttggc    300
caggggacca agctggagat caaa    324

<210> SEQ ID NO 298
<211> LENGTH: 108
<212> TYPE: PRT
<213> ORGANISM: Artificial Sequence
<220> FEATURE:
<223> OTHER INFORMATION: Synthetic

<400> SEQUENCE: 298

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Leu Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Asn Arg Leu Glu
65                  70                  75                  80

Pro Glu Asp Phe Ala Val Tyr Tyr Cys Gln Gln Tyr Ala Tyr Ser Pro
                85                  90                  95

Tyr Thr Phe Gly Gln Gly Thr Lys Leu Glu Ile Lys
            100                 105

<210> SEQ ID NO 299
<211> LENGTH: 21
<212> TYPE: DNA
<213> ORGANISM: Artificial Sequence
<220> FEATURE:
<223> OTHER INFORMATION: Synthetic

<400> SEQUENCE: 299
cagagtgtta gcagcaccta c    21

<210> SEQ ID NO 300
<211> LENGTH: 7
<212> TYPE: PRT
<213> ORGANISM: Artificial Sequence
<220> FEATURE:
<223> OTHER INFORMATION: Synthetic

<400> SEQUENCE: 300

Gln Ser Val Ser Ser Thr Tyr
1               5

<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301 ggtgcatcc    9

<210> SEQ ID NO 302
<211> LENGTH: 3
<212> TYPE: PRT
<213> ORGANISM: Artificial Sequence
<220> FEATURE:

<223> OTHER INFORMATION: Synthetic

<400> SEQUENCE: 302

Gly Ala Ser
 1

<210> SEQ ID NO 303
<211> LENGTH: 27
<212> TYPE: DNA
<213> ORGANISM: Artificial Sequence
<220> FEATURE:
<223> OTHER INFORMATION: Synthetic

<400> SEQUENCE: 303
caacagtatg cttactcacc gtacact                                         27

<210> SEQ ID NO 304
<211> LENGTH: 9
<212> TYPE: PRT
<213> ORGANISM: Artificial Sequence
<220> FEATURE:
<223> OTHER INFORMATION: Synthetic

<400> SEQUENCE: 304

Gln Gln Tyr Ala Tyr Ser Pro Tyr Thr
 1               5

<210> SEQ ID NO 305
<211> LENGTH: 363
<212> TYPE: DNA
<213> ORGANISM: Artificial Sequence
<220> FEATURE:
<223> OTHER INFORMATION: Synthetic

<400> SEQUENCE: 305
caggtgcagc tggtggagtc tgggggaggc gtggtccagc ctggggaggtc cctgagactc     60 tcctgtgcag cgtctggatt cagtttcagt gactatgtca tgcactgggt ccgccaggct    120
ccaggcaagg ggctggagtg ggtggcatct atatggtttg atggaagtaa tgaattctat    180
gcagactccg tgaagggccg attcaccatc tccagagaca attccaagaa cacgctgttt    240
ctgcaaatga acagtctgag agccgaggac acggctgtgt attactgtgc gaaaaaggga    300
gtgttggtag ctacctctgc ttttgatatc tggggccaag ggacaatggt caccgtctct    360
tca                                                                 363

<210> SEQ ID NO 306
<211> LENGTH: 121
<212> TYPE: PRT
<213> ORGANISM: Artificial Sequence
<220> FEATURE:
<223> OTHER INFORMATION: Synthetic

<400> SEQUENCE: 306

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Ser Phe Ser Asp Tyr
             20                  25                  30

Val Met His Trp Val Arg Gln Ala Pro Gly Lys Gly Leu Glu Trp Val
         35                  40                  45

Ala Ser Ile Trp Phe Asp Gly Ser Asn Glu Tyr Ala Asp Ser Val
     50                  55                  60

Lys Gly Arg Phe Thr Ile Ser Arg Asp Asn Ser Lys Asn Thr Leu Phe

```
                65                  70                  75                  80
Leu Gln Met Asn Ser Leu Arg Ala Glu Asp Thr Ala Val Tyr Tyr Cys
                        85                  90                  95

Ala Lys Lys Gly Val Leu Val Ala Thr Ser Ala Phe Asp Ile Trp Gly
                100                 105                 110

Gln Gly Thr Met Val Thr Val Ser Ser
        115                 120

<210> SEQ ID NO 307
<211> LENGTH: 24
<212> TYPE: DNA
<213> ORGANISM: Artificial Sequence
<220> FEATURE:
<223> OTHER INFORMATION: Synthetic

<400> SEQUENCE: 307
ggattcagtt tcagtgacta tgtc                                              24

<210> SEQ ID NO 308
<211> LENGTH: 8
<212> TYPE: PRT
<213> ORGANISM: Artificial Sequence
<220> FEATURE:
<223> OTHER INFORMATION: Synthetic

<400> SEQUENCE: 308

Gly Phe Ser Phe Ser Asp Tyr Val
  1               5

<210> SEQ ID NO 309
<211> LENGTH: 24
<212> TYPE: DNA
<213> ORGANISM: Artificial Sequence
<220> FEATURE:
<223> OTHER INFORMATION: Synthetic

<400> SEQUENCE: 309
atatggtttg atggaagtaa tgaa                                              24

<210> SEQ ID NO 310
<211> LENGTH: 8
<212> TYPE: PRT
<213> ORGANISM: Artificial Sequence
<220> FEATURE:
<223> OTHER INFORMATION: Synthetic

<400> SEQUENCE: 310

Ile Trp Phe Asp Gly Ser Asn Glu
  1               5

<210> SEQ ID NO 311
<211> LENGTH: 42
<212> TYPE: DNA
<213> ORGANISM: Artificial Sequence
<220> FEATURE:
<223> OTHER INFORMATION: Synthetic

<400> SEQUENCE: 311
gcgaaaaagg gagtgttggt agctacctct gcttttgata tc                          42

<210> SEQ ID NO 312
<211> LENGTH: 14
<212> TYPE: PRT
<213> ORGANISM: Artificial Sequence
<220> FEATURE:
```

<223> OTHER INFORMATION: Synthetic

<400> SEQUENCE: 312

Ala Lys Lys Gly Val Leu Val Ala Thr Ser Ala Phe Asp Ile
1               5                   10

<210> SEQ ID NO 313
<211> LENGTH: 324
<212> TYPE: DNA
<213> ORGANISM: Artificial Sequence
<220> FEATURE:
<223> OTHER INFORMATION: Synthetic

<400> SEQUENCE: 313

```
gacatccagt tgacccagtc tccatcctcc ctgtctgcat ctgtaggaga cagagtcacc    60
atcacttgcc gggcaagtca gagcattaac aactatttaa attggtatca tcagaaacca   120
gggaaagccc ctaagctcct aatctatgct gcatccagtt tgcaaagtgg ggtcccatca   180
aggttcagtg gcagtggatc tgggacagat tacactctca ccatcagcag tctgcaacct   240
gaagattttg gaaattacta ctgtcaacag agttacagaa cttccatgta cacttttggc   300
caggggacca aggtggaaat caaa                                          324
```

<210> SEQ ID NO 314
<211> LENGTH: 108
<212> TYPE: PRT
<213> ORGANISM: Artificial Sequence
<220> FEATURE:
<223> OTHER INFORMATION: Synthetic

<400> SEQUENCE: 314

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Tyr
            20                  25                  30

Leu Asn Trp Tyr His Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Gly Asn Tyr Tyr Cys Gln Gln Ser Tyr Arg Thr Ser Met
                85                  90                  95

Tyr Thr Phe Gly Gln Gly Thr Lys Val Glu Ile Lys
            100                 105

<210> SEQ ID NO 315
<211> LENGTH: 18
<212> TYPE: DNA
<213> ORGANISM: Artificial Sequence
<220> FEATURE:
<223> OTHER INFORMATION: Synthetic

<400> SEQUENCE: 315
cagagcatta acaactat                                                  18

<210> SEQ ID NO 316
<211> LENGTH: 6
<212> TYPE: PRT
<213> ORGANISM: Artificial Sequence
<220> FEATURE:
<223> OTHER INFORMATION: Synthetic

<400> SEQUENCE: 316

Gln Ser Ile Asn Asn Tyr
 1               5

<210> SEQ ID NO 317
<211> LENGTH: 9
<212> TYPE: DNA
<213> ORGANISM: Artificial Sequence
<220> FEATURE:
<223> OTHER INFORMATION: Synthetic

<400> SEQUENCE: 317 gctgcatcc                                                                 9

<210> SEQ ID NO 318
<211> LENGTH: 3
<212> TYPE: PRT
<213> ORGANISM: Artificial Sequence
<220> FEATURE:
<223> OTHER INFORMATION: Synthetic

<400> SEQUENCE: 318

Ala Ala Ser
 1

<210> SEQ ID NO 319
<211> LENGTH: 30
<212> TYPE: DNA
<213> ORGANISM: Artificial Sequence
<220> FEATURE:
<223> OTHER INFORMATION: Synthetic

<400> SEQUENCE: 319
caacagagtt acagaacttc catgtacact                                          30

<210> SEQ ID NO 320
<211> LENGTH: 10
<212> TYPE: PRT
<213> ORGANISM: Artificial Sequence
<220> FEATURE:
<223> OTHER INFORMATION: Synthetic

<400> SEQUENCE: 320

Gln Gln Ser Tyr Arg Thr Ser Met Tyr Thr
 1               5                  10

<210> SEQ ID NO 321
<211> LENGTH: 360
<212> TYPE: DNA
<213> ORGANISM: Artificial Sequence
<220> FEATURE:
<223> OTHER INFORMATION: Synthetic

<400> SEQUENCE: 321
gaggtgcagc tggtggagtc tgggggaggc ttggtacagc cggggggtc cctgagactc          60 tcctgtgcag cctctggatt caccttttagc agctatgcca tgagctgggt ccgccaggtt      120
ccagggaagg gctggagtg gtctcagct attagtggta gtggtgataa acatataac          180 gcagagtccg tgaagggccg gttcaccatc tccagagaca attccaagaa tatgttgtat      240
ctgcaaatga acagcctgag agccgaggac acggccgtat attactgtgc gaaaacaaag      300
tttagcagct cgttgctctt tgactactgg ggccagggaa ccctggtcac cgtctcctca      360

```
<210> SEQ ID NO 322
<211> LENGTH: 120
<212> TYPE: PRT
<213> ORGANISM: Artificial Sequence
<220> FEATURE:
<223> OTHER INFORMATION: Synthetic

<400> SEQUENCE: 322
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Val Pro Gly Lys Gly Leu Glu Trp Val
        35                  40                  45

Ser Ala Ile Ser Gly Ser Gly Asp Asn Thr Tyr Asn Ala Glu Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Val Tyr Tyr Cys
                85                  90                  95

Ala Lys Thr Lys Phe Ser Ser Ser Leu Leu Phe Asp Tyr Trp Gly Gln
            100                 105                 110

Gly Thr Leu Val Thr Val Ser Ser
        115                 120

```
<210> SEQ ID NO 323
<211> LENGTH: 24
<212> TYPE: DNA
<213> ORGANISM: Artificial Sequence
<220> FEATURE:
<223> OTHER INFORMATION: Synthetic

<400> SEQUENCE: 323
ggattcacct ttagcagcta tgcc                                          24

<210> SEQ ID NO 324
<211> LENGTH: 8
<212> TYPE: PRT
<213> ORGANISM: Artificial Sequence
<220> FEATURE:
<223> OTHER INFORMATION: Synthetic

<400> SEQUENCE: 324
```

Gly Phe Thr Phe Ser Ser Tyr Ala
1               5

```
<210> SEQ ID NO 325
<211> LENGTH: 24
<212> TYPE: DNA
<213> ORGANISM: Artificial Sequence
<220> FEATURE:
<223> OTHER INFORMATION: Synthetic

<400> SEQUENCE: 325
attagtggta gtggtgataa taca                                          24

<210> SEQ ID NO 326
<211> LENGTH: 8
<212> TYPE: PRT
<213> ORGANISM: Artificial Sequence
<220> FEATURE:
<223> OTHER INFORMATION: Synthetic

<400> SEQUENCE: 326
```

Ile Ser Gly Ser Gly Asp Asn Thr
1               5

<210> SEQ ID NO 327
<211> LENGTH: 39
<212> TYPE: DNA
<213> ORGANISM: Artificial Sequence
<220> FEATURE:
<223> OTHER INFORMATION: Synthetic

<400> SEQUENCE: 327
gcgaaaacaa agtttagcag ctcgttgctc tttgactac                                39

<210> SEQ ID NO 328
<211> LENGTH: 13
<212> TYPE: PRT
<213> ORGANISM: Artificial Sequence
<220> FEATURE:
<223> OTHER INFORMATION: Synthetic

<400> SEQUENCE: 328

Ala Lys Thr Lys Phe Ser Ser Ser Leu Leu Phe Asp Tyr
1               5                   10

<210> SEQ ID NO 329
<211> LENGTH: 318
<212> TYPE: DNA
<213> ORGANISM: Artificial Sequence
<220> FEATURE:
<223> OTHER INFORMATION: Synthetic

<400> SEQUENCE: 329
gacatcgtga tgacccagtc tccttccacc ctgtctgcat ctgtaggaga cagagtcacc        60
atcacttgcc gggccagtca gagtattagt tggtggttgg cctggtatca gcagaaacca       120
gggaaagccc ctaagctcct gatctataag gcgtctagtt tagaaagtgg ggtcccatca       180
aggttcagcg gcagtggatc tgggacagaa ttcactctca ccatcagcag cctgcagcct       240
gatgattttg caacttatta ctgccaacag tataatagtt attccacttt cggcggaggg       300
accaagctgg agatcaaa                                                     318

<210> SEQ ID NO 330
<211> LENGTH: 106
<212> TYPE: PRT
<213> ORGANISM: Artificial Sequence
<220> FEATURE:
<223> OTHER INFORMATION: Synthetic

<400> SEQUENCE: 330

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Trp Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Thr
                85                  90                  95

Phe Gly Gly Gly Thr Lys Leu Glu Ile Lys
            100                 105

<210> SEQ ID NO 331
<211> LENGTH: 18
<212> TYPE: DNA
<213> ORGANISM: Artificial Sequence
<220> FEATURE:
<223> OTHER INFORMATION: Synthetic

<400> SEQUENCE: 331
cagagtatta gttggtgg                                              18

<210> SEQ ID NO 332
<211> LENGTH: 6
<212> TYPE: PRT
<213> ORGANISM: Artificial Sequence
<220> FEATURE:
<223> OTHER INFORMATION: Synthetic

<400> SEQUENCE: 332

Gln Ser Ile Ser Trp Trp
 1               5

<210> SEQ ID NO 333
<211> LENGTH: 9
<212> TYPE: DNA
<213> ORGANISM: Artificial Sequence
<220> FEATURE:
<223> OTHER INFORMATION: Synthetic

<400> SEQUENCE: 333 aaggcgtct                                                         9

<210> SEQ ID NO 334
<211> LENGTH: 3
<212> TYPE: PRT
<213> ORGANISM: Artificial Sequence
<220> FEATURE:
<223> OTHER INFORMATION: Synthetic

<400> SEQUENCE: 334

Lys Ala Ser
 1

<210> SEQ ID NO 335
<211> LENGTH: 24
<212> TYPE: DNA
<213> ORGANISM: Artificial Sequence
<220> FEATURE:
<223> OTHER INFORMATION: Synthetic

<400> SEQUENCE: 335
caacagtata atagttattc cact                                       24

<210> SEQ ID NO 336
<211> LENGTH: 8
<212> TYPE: PRT
<213> ORGANISM: Artificial Sequence
<220> FEATURE:
<223> OTHER INFORMATION: Synthetic

<400> SEQUENCE: 336

Gln Gln Tyr Asn Ser Tyr Ser Thr
 1               5

<210> SEQ ID NO 337
<211> LENGTH: 372
<212> TYPE: DNA
<213> ORGANISM: Artificial Sequence
<220> FEATURE:
<223> OTHER INFORMATION: Synthetic

<400> SEQUENCE: 337

```
gaggtgcagc tggtggagtc tgggggaggc ttggtacagc ctgggggtc cctgagactc      60
tcctgtgcag cctctacatt caccttagc agctatgcca tgacctgggt ccgccaggct     120
ccagggaagg gctggagtg ggtctcaagt attagtggta gtggtgatag cacatactac     180
gcagactccg tgaagggccg gttcaccatc tccagagaca attccaagaa cacgctgttt    240
ctgcaaatga acagcctgag agccgaggac acggccgtat attactgtgc gaaaaaggat    300
gggcctggga ggtattacgt gaggtacggt atggacgtct ggggccaagg gaccacggtc    360
accgtctcct ca                                                        372
```

<210> SEQ ID NO 338
<211> LENGTH: 124
<212> TYPE: PRT
<213> ORGANISM: Artificial Sequence
<220> FEATURE:
<223> OTHER INFORMATION: Synthetic

<400> SEQUENCE: 338

```
Glu Val Gln Leu Val Glu Ser Gly Gly Gly Leu Val Gln Pro Gly Gly
 1               5                  10                  15
Ser Leu Arg Leu Ser Cys Ala Ala Ser Thr Phe Thr Phe Ser Ser Tyr
            20                  25                  30
Ala Met Thr Trp Val Arg Gln Ala Pro Gly Lys Gly Leu Glu Trp Val
        35                  40                  45
Ser Ser Ile Ser Gly Ser Gly Asp Ser Thr Tyr Tyr Ala Asp Ser Val
    50                  55                  60
Lys Gly Arg Phe Thr Ile Ser Arg Asp Asn Ser Lys Asn Thr Leu Phe
65                  70                  75                  80
Leu Gln Met Asn Ser Leu Arg Ala Glu Asp Thr Ala Val Tyr Tyr Cys
                85                  90                  95
Ala Lys Lys Asp Gly Pro Gly Arg Tyr Tyr Val Arg Tyr Gly Met Asp
            100                 105                 110
Val Trp Gly Gln Gly Thr Thr Val Thr Val Ser Ser
        115                 120
```

<210> SEQ ID NO 339
<211> LENGTH: 24
<212> TYPE: DNA
<213> ORGANISM: Artificial Sequence
<220> FEATURE:
<223> OTHER INFORMATION: Synthetic

<400> SEQUENCE: 339

```
acattcacct ttagcagcta tgcc                                            24
```

<210> SEQ ID NO 340
<211> LENGTH: 8
<212> TYPE: PRT
<213> ORGANISM: Artificial Sequence
<220> FEATURE:
<223> OTHER INFORMATION: Synthetic

<400> SEQUENCE: 340

```
Thr Phe Thr Phe Ser Ser Tyr Ala
 1               5
```

<210> SEQ ID NO 341
<211> LENGTH: 24
<212> TYPE: DNA
<213> ORGANISM: Artificial Sequence
<220> FEATURE:
<223> OTHER INFORMATION: Synthetic

<400> SEQUENCE: 341
attagtggta gtggtgatag caca                                         24

<210> SEQ ID NO 342
<211> LENGTH: 8
<212> TYPE: PRT
<213> ORGANISM: Artificial Sequence
<220> FEATURE:
<223> OTHER INFORMATION: Synthetic

<400> SEQUENCE: 342

```
Ile Ser Gly Ser Gly Asp Ser Thr
 1               5
```

<210> SEQ ID NO 343
<211> LENGTH: 51
<212> TYPE: DNA
<213> ORGANISM: Artificial Sequence
<220> FEATURE:
<223> OTHER INFORMATION: Synthetic

<400> SEQUENCE: 343
gcgaaaaagg atgggcctgg gaggtattac gtgaggtacg gtatggacgt c           51

<210> SEQ ID NO 344
<211> LENGTH: 17
<212> TYPE: PRT
<213> ORGANISM: Artificial Sequence
<220> FEATURE:
<223> OTHER INFORMATION: Synthetic

<400> SEQUENCE: 344

```
Ala Lys Lys Asp Gly Pro Gly Arg Tyr Tyr Val Arg Tyr Gly Met Asp
 1               5                  10                  15
Val
```

<210> SEQ ID NO 345
<211> LENGTH: 321
<212> TYPE: DNA
<213> ORGANISM: Artificial Sequence
<220> FEATURE:
<223> OTHER INFORMATION: Synthetic

<400> SEQUENCE: 345
gacatccaga tgacccagtc tccatcttcc gtgtctgcat ctgtaggaga cagagtcacc     60
atcacttgtc gggcgagtca gggtattagc agctggttag cctggtatca gcagaaacca    120
gggaaagccc ctaagctcct gatctatact acatccagtt tgcaaagtgg ggtcccatcc    180
aggttcagcg gcagtggatc tgggacagat ttcactctca ccatcagcag cctgcagcct    240
gaagattttg caacttatta ttgtcaacag gctaacagtt tccctctcac tttcggcgga    300
gggaccaaag tggatatcaa a                                              321

<210> SEQ ID NO 346

<211> LENGTH: 107
<212> TYPE: PRT
<213> ORGANISM: Artificial Sequence
<220> FEATURE:
<223> OTHER INFORMATION: Synthetic

<400> SEQUENCE: 346

Asp Ile Gln Met Thr Gln Ser Pro Ser Ser Val Ser Ala Ser Val Gly
 1               5                  10                  15
Asp Arg Val Thr Ile Thr Cys Arg Ala Ser Gln Gly Ile Ser Ser Trp
             20                  25                  30
Leu Ala Trp Tyr Gln Gln Lys Pro Gly Lys Ala Pro Lys Leu Leu Ile
         35                  40                  45
Tyr Thr Thr Ser Ser Leu Gln Ser Gly Val Pro Ser Arg Phe Ser Gly
 50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ala Asn Ser Phe Pro Leu
             85                  90                  95
Thr Phe Gly Gly Gly Thr Lys Val Asp Ile Lys
            100                 105

<210> SEQ ID NO 347
<211> LENGTH: 18
<212> TYPE: DNA
<213> ORGANISM: Artificial Sequence
<220> FEATURE:
<223> OTHER INFORMATION: Synthetic

<400> SEQUENCE: 347
cagggtatta gcagctgg                                                         18

<210> SEQ ID NO 348
<211> LENGTH: 6
<212> TYPE: PRT
<213> ORGANISM: Artificial Sequence
<220> FEATURE:
<223> OTHER INFORMATION: Synthetic

<400> SEQUENCE: 348

Gln Gly Ile Ser Ser Trp
 1               5

<210> SEQ ID NO 349
<211> LENGTH: 9
<212> TYPE: DNA
<213> ORGANISM: Artificial Sequence
<220> FEATURE:
<223> OTHER INFORMATION: Synthetic

<400> SEQUENCE: 349 actacatcc                                                                    9

<210> SEQ ID NO 350
<211> LENGTH: 3
<212> TYPE: PRT
<213> ORGANISM: Artificial Sequence
<220> FEATURE:
<223> OTHER INFORMATION: Synthetic

<400> SEQUENCE: 350

Thr Thr Ser
 1

<210> SEQ ID NO 351
<211> LENGTH: 27
<212> TYPE: DNA
<213> ORGANISM: Artificial Sequence
<220> FEATURE:
<223> OTHER INFORMATION: Synthetic

<400> SEQUENCE: 351
caacaggcta acagtttccc tctcact                                              27

<210> SEQ ID NO 352
<211> LENGTH: 9
<212> TYPE: PRT
<213> ORGANISM: Artificial Sequence
<220> FEATURE:
<223> OTHER INFORMATION: Synthetic

<400> SEQUENCE: 352

Gln Gln Ala Asn Ser Phe Pro Leu Thr
 1               5

<210> SEQ ID NO 353
<211> LENGTH: 372
<212> TYPE: DNA
<213> ORGANISM: Artificial Sequence
<220> FEATURE:
<223> OTHER INFORMATION: Synthetic

<400> SEQUENCE: 353
gaggtgcagc tggtggagtc tgggggaggc ttggaacagc ctgggggttc cctgagactc          60
tcctgtgcag cctctggatt cacctttagc agctatgtca tgagctgggt ccgccaggtt         120
ccagggaagg ggctggagtg ggtctcagtt atcagtggta gtggtggtag cacatactac         180
gcagactccg tgaagggccg gttcaccatc tccagagaca attccaagaa cacgctgtat         240
ctgcaaatga acagcctgag agccgaggac acggccgtat attactgtgc gaaacccttca        300 tcttatagca gctcgaactt ccactacggt atggacgtct ggggccaagg gaccacggtc         360
accgtctcct ca                                                            372

<210> SEQ ID NO 354
<211> LENGTH: 124
<212> TYPE: PRT
<213> ORGANISM: Artificial Sequence
<220> FEATURE:
<223> OTHER INFORMATION: Synthetic

<400> SEQUENCE: 354

Glu Val Gln Leu Val Glu Ser Gly Gly Gly Leu Glu Gln Pro Gly Gly
 1               5                  10                  15

Ser Leu Arg Leu Ser Cys Ala Ala Ser Gly Phe Thr Phe Ser Ser Tyr
             20                  25                  30

Val Met Ser Trp Val Arg Gln Val Pro Gly Lys Gly Leu Glu Trp Val
         35                  40                  45

Ser Val Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Ser Ser Tyr Ser Ser Ser Asn Phe His Tyr Gly Met Asp
            100                 105                 110

Val Trp Gly Gln Gly Thr Thr Val Thr Val Ser Ser
        115                 120

<210> SEQ ID NO 355
<211> LENGTH: 24
<212> TYPE: DNA
<213> ORGANISM: Artificial Sequence
<220> FEATURE:
<223> OTHER INFORMATION: Synthetic

<400> SEQUENCE: 355
ggattcacct ttagcagcta tgtc                                          24

<210> SEQ ID NO 356
<211> LENGTH: 8
<212> TYPE: PRT
<213> ORGANISM: Artificial Sequence
<220> FEATURE:
<223> OTHER INFORMATION: Synthetic

<400> SEQUENCE: 356

Gly Phe Thr Phe Ser Ser Tyr Val
1               5

<210> SEQ ID NO 357
<211> LENGTH: 24
<212> TYPE: DNA
<213> ORGANISM: Artificial Sequence
<220> FEATURE:
<223> OTHER INFORMATION: Synthetic

<400> SEQUENCE: 357
atcagtggta gtggtggtag caca                                          24

<210> SEQ ID NO 358
<211> LENGTH: 8
<212> TYPE: PRT
<213> ORGANISM: Artificial Sequence
<220> FEATURE:
<223> OTHER INFORMATION: Synthetic

<400> SEQUENCE: 358

Ile Ser Gly Ser Gly Gly Ser Thr
1               5

<210> SEQ ID NO 359
<211> LENGTH: 51
<212> TYPE: DNA
<213> ORGANISM: Artificial Sequence
<220> FEATURE:
<223> OTHER INFORMATION: Synthetic

<400> SEQUENCE: 359
gcgaaaccct catcttatag cagctcgaac ttccactacg gtatggacgt c            51

<210> SEQ ID NO 360
<211> LENGTH: 17
<212> TYPE: PRT
<213> ORGANISM: Artificial Sequence
<220> FEATURE:
<223> OTHER INFORMATION: Synthetic

<400> SEQUENCE: 360

Ala Lys Pro Ser Ser Tyr Ser Ser Ser Asn Phe His Tyr Gly Met Asp
1               5                   10                  15

Val

<210> SEQ ID NO 361
<211> LENGTH: 321
<212> TYPE: DNA
<213> ORGANISM: Artificial Sequence
<220> FEATURE:
<223> OTHER INFORMATION: Synthetic

<400> SEQUENCE: 361

```
gacatccaga tgacccagtc tccatattcc gtgtctgcat ctgtaggaga cagagtcacc      60
atcacttgtc gggcgagtca gggtattagc agctggttag cctggtatca gcagaaacca     120
gggagagccc ctaagctcct gatctatgct gcatccagtt tgcaaagtgg ggtcccatca     180
aggttcagcg gcagtggatc tgggacagat ttcactctca ccatcagcag cctgcagcct     240
gaagattttg caacttacta ttgtcaaaag actaacagtt tcccattcac tttcggccct     300
gggaccaagg tggaaatcaa a                                               321
```

<210> SEQ ID NO 362
<211> LENGTH: 107
<212> TYPE: PRT
<213> ORGANISM: Artificial Sequence
<220> FEATURE:
<223> OTHER INFORMATION: Synthetic

<400> SEQUENCE: 362

```
Asp Ile Gln Met Thr Gln Ser Pro Tyr Ser Val Ser Ala Ser Val Gly
  1               5                  10                  15
Asp Arg Val Thr Ile Thr Cys Arg Ala Ser Gln Gly Ile Ser Ser Trp
             20                  25                  30
Leu Ala Trp Tyr Gln Gln Lys Pro Gly Arg Ala Pro Lys Leu Leu Ile
         35                  40                  45
Tyr Ala Ala Ser Ser Leu Gln Ser Gly Val Pro Ser Arg Phe Ser Gly
     50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Lys Thr Asn Ser Phe Pro Phe
                 85                  90                  95
Thr Phe Gly Pro Gly Thr Lys Val Glu Ile Lys
            100                 105
```

<210> SEQ ID NO 363
<211> LENGTH: 18
<212> TYPE: DNA
<213> ORGANISM: Artificial Sequence
<220> FEATURE:
<223> OTHER INFORMATION: Synthetic

<400> SEQUENCE: 363

```
cagggtatta gcagctgg                                                    18
```

<210> SEQ ID NO 364
<211> LENGTH: 6
<212> TYPE: PRT
<213> ORGANISM: Artificial Sequence
<220> FEATURE:
<223> OTHER INFORMATION: Synthetic

<400> SEQUENCE: 364

```
Gln Gly Ile Ser Ser Trp
  1               5
```

<210> SEQ ID NO 365
<211> LENGTH: 9
<212> TYPE: DNA
<213> ORGANISM: Artificial Sequence
<220> FEATURE:
<223> OTHER INFORMATION: Synthetic

<400> SEQUENCE: 365 gctgcatcc                                                                 9

<210> SEQ ID NO 366
<211> LENGTH: 3
<212> TYPE: PRT
<213> ORGANISM: Artificial Sequence
<220> FEATURE:
<223> OTHER INFORMATION: Synthetic

<400> SEQUENCE: 366

Ala Ala Ser
 1

<210> SEQ ID NO 367
<211> LENGTH: 27
<212> TYPE: DNA
<213> ORGANISM: Artificial Sequence
<220> FEATURE:
<223> OTHER INFORMATION: Synthetic

<400> SEQUENCE: 367
caaaagacta acagtttccc attcact                                            27

<210> SEQ ID NO 368
<211> LENGTH: 9
<212> TYPE: PRT
<213> ORGANISM: Artificial Sequence
<220> FEATURE:
<223> OTHER INFORMATION: Synthetic

<400> SEQUENCE: 368

Gln Lys Thr Asn Ser Phe Pro Phe Thr
 1               5

<210> SEQ ID NO 369
<211> LENGTH: 141
<212> TYPE: PRT
<213> ORGANISM: Artificial Sequence
<220> FEATURE:
<223> OTHER INFORMATION: Synthetic

<400> SEQUENCE: 369

Ala Gly Gly Pro Gly Ser Arg Ala Arg Ala Gly Ala Arg Gly Cys
 1               5                  10                  15

Arg Leu Arg Ser Gln Leu Val Pro Val Arg Ala Leu Gly Leu Gly His
                20                  25                  30

Arg Ser Asp Glu Leu Val Arg Phe Arg Phe Cys Ser Gly Ser Cys Arg
            35                  40                  45

Arg Ala Arg Ser Pro His Asp Leu Ser Leu Ala Ser Leu Leu Gly Ala
        50                  55                  60

Gly Ala Leu Arg Pro Pro Gly Ser Arg Pro Val Ser Gln Pro Cys
65                  70                  75                  80

Cys Arg Pro Thr Arg Tyr Glu Ala Val Ser Phe Met Asp Val Asn Ser
                85                  90                  95

```
Thr Trp Arg Thr Val Asp Arg Leu Ser Ala Thr Ala Cys Gly Cys Leu
            100                 105                 110

Gly Glu Gln Lys Leu Ile Ser Glu Glu Asp Leu Gly Gly Glu Gln Lys
        115                 120                 125

Leu Ile Ser Glu Glu Asp Leu His His His His His His
        130                 135                 140

<210> SEQ ID NO 370
<211> LENGTH: 371
<212> TYPE: PRT
<213> ORGANISM: Artificial Sequence
<220> FEATURE:
<223> OTHER INFORMATION: Synthetic

<400> SEQUENCE: 370

Asp Pro Leu Pro Thr Glu Ser Arg Leu Met Asn Ser Cys Leu Gln Ala
1               5                   10                  15

Arg Arg Lys Cys Gln Ala Asp Pro Thr Cys Ser Ala Ala Tyr His His
            20                  25                  30

Leu Asp Ser Cys Thr Ser Ser Ile Ser Thr Pro Leu Pro Ser Glu Glu
        35                  40                  45

Pro Ser Val Pro Ala Asp Cys Leu Glu Ala Ala Gln Gln Leu Arg Asn
    50                  55                  60

Ser Ser Leu Ile Gly Cys Met Cys His Arg Arg Met Lys Asn Gln Val
65                  70                  75                  80

Ala Cys Leu Asp Ile Tyr Trp Thr Val His Arg Ala Arg Ser Leu Gly
                85                  90                  95

Asn Tyr Glu Leu Asp Val Ser Pro Tyr Glu Asp Thr Val Thr Ser Lys
            100                 105                 110

Pro Trp Lys Met Asn Leu Ser Lys Leu Asn Met Leu Lys Pro Asp Ser
        115                 120                 125

Asp Leu Cys Leu Lys Phe Ala Met Leu Cys Thr Leu Asn Asp Lys Cys
    130                 135                 140

Asp Arg Leu Arg Lys Ala Tyr Gly Glu Ala Cys Ser Gly Pro His Cys
145                 150                 155                 160

Gln Arg His Val Cys Leu Arg Gln Leu Leu Thr Phe Phe Glu Lys Ala
                165                 170                 175

Ala Glu Pro His Ala Gln Gly Leu Leu Leu Cys Pro Cys Ala Pro Asn
            180                 185                 190

Asp Arg Gly Cys Gly Glu Arg Arg Asn Thr Ile Ala Pro Asn Cys
        195                 200                 205

Ala Leu Pro Pro Val Ala Pro Asn Cys Leu Glu Leu Arg Arg Leu Cys
    210                 215                 220

Phe Ser Asp Pro Leu Cys Arg Ser Arg Leu Val Asp Phe Gln Thr His
225                 230                 235                 240

Cys His Pro Met Asp Ile Leu Gly Thr Cys Ala Thr Glu Gln Ser Arg
                245                 250                 255

Cys Leu Arg Ala Tyr Leu Gly Leu Ile Gly Thr Ala Met Thr Pro Asn
            260                 265                 270

Phe Val Ser Asn Val Asn Thr Ser Val Ala Leu Ser Cys Thr Cys Arg
        275                 280                 285

Gly Ser Gly Asn Leu Gln Glu Glu Cys Glu Met Leu Glu Gly Phe Phe
    290                 295                 300

Ser His Asn Pro Cys Leu Thr Glu Ala Ile Ala Ala Lys Met Arg Phe
305                 310                 315                 320
```

```
His Ser Gln Leu Phe Ser Gln Asp Trp Pro His Pro Thr Phe Ala Val
            325                 330                 335

Met Ala His Gln Asn Glu Asn Glu Gln Lys Leu Ile Ser Glu Glu Asp
        340                 345                 350

Leu Gly Gly Glu Gln Lys Leu Ile Ser Glu Glu Asp Leu His His His
        355                 360                 365

His His His
    370

<210> SEQ ID NO 371
<211> LENGTH: 578
<212> TYPE: PRT
<213> ORGANISM: Artificial Sequence
<220> FEATURE:
<223> OTHER INFORMATION: Synthetic

<400> SEQUENCE: 371

Asp Pro Leu Pro Thr Glu Ser Arg Leu Met Asn Ser Cys Leu Gln Ala
1               5                   10                  15

Arg Arg Lys Cys Gln Ala Asp Pro Thr Cys Ser Ala Ala Tyr His His
            20                  25                  30

Leu Asp Ser Cys Thr Ser Ser Ile Ser Thr Pro Leu Pro Ser Glu Glu
        35                  40                  45

Pro Ser Val Pro Ala Asp Cys Leu Glu Ala Ala Gln Gln Leu Arg Asn
    50                  55                  60

Ser Ser Leu Ile Gly Cys Met Cys His Arg Arg Met Lys Asn Gln Val
65                  70                  75                  80

Ala Cys Leu Asp Ile Tyr Trp Thr Val His Arg Ala Arg Ser Leu Gly
                85                  90                  95

Asn Tyr Glu Leu Asp Val Ser Pro Tyr Glu Asp Thr Val Thr Ser Lys
            100                 105                 110

Pro Trp Lys Met Asn Leu Ser Lys Leu Asn Met Leu Lys Pro Asp Ser
        115                 120                 125

Asp Leu Cys Leu Lys Phe Ala Met Leu Cys Thr Leu Asn Asp Lys Cys
    130                 135                 140

Asp Arg Leu Arg Lys Ala Tyr Gly Glu Ala Cys Ser Gly Pro His Cys
145                 150                 155                 160

Gln Arg His Val Cys Leu Arg Gln Leu Leu Thr Phe Phe Glu Lys Ala
                165                 170                 175

Ala Glu Pro His Ala Gln Gly Leu Leu Leu Cys Pro Cys Ala Pro Asn
            180                 185                 190

Asp Arg Gly Cys Gly Glu Arg Arg Asn Thr Ile Ala Pro Asn Cys
        195                 200                 205

Ala Leu Pro Pro Val Ala Pro Asn Cys Leu Glu Leu Arg Arg Leu Cys
    210                 215                 220

Phe Ser Asp Pro Leu Cys Arg Ser Arg Leu Val Asp Phe Gln Thr His
225                 230                 235                 240

Cys His Pro Met Asp Ile Leu Gly Thr Cys Ala Thr Glu Gln Ser Arg
                245                 250                 255

Cys Leu Arg Ala Tyr Leu Gly Leu Ile Gly Thr Ala Met Thr Pro Asn
            260                 265                 270

Phe Val Ser Asn Val Asn Thr Ser Val Ala Leu Ser Cys Thr Cys Arg
        275                 280                 285

Gly Ser Gly Asn Leu Gln Glu Glu Cys Glu Met Leu Glu Gly Phe Phe
    290                 295                 300
```

```
Ser His Asn Pro Cys Leu Thr Glu Ala Ile Ala Ala Lys Met Arg Phe
305                 310                 315                 320

His Ser Gln Leu Phe Ser Gln Asp Trp Pro His Pro Thr Phe Ala Val
            325                 330                 335

Met Ala His Gln Asn Glu Asn Pro Ala Val Arg Pro Gln Pro Trp Asp
            340                 345                 350

Lys Thr His Thr Cys Pro Pro Cys Pro Ala Pro Glu Leu Leu Gly Gly
            355                 360                 365

Pro Ser Val Phe Leu Phe Pro Pro Lys Pro Lys Asp Thr Leu Met Ile
370                 375                 380

Ser Arg Thr Pro Glu Val Thr Cys Val Val Val Asp Val Ser His Glu
385                 390                 395                 400

Asp Pro Glu Val Lys Phe Asn Trp Tyr Val Asp Gly Val Glu Val His
            405                 410                 415

Asn Ala Lys Thr Lys Pro Arg Glu Glu Gln Tyr Asn Ser Thr Tyr Arg
            420                 425                 430

Val Val Ser Val Leu Thr Val Leu His Gln Asp Trp Leu Asn Gly Lys
            435                 440                 445

Glu Tyr Lys Cys Lys Val Ser Asn Lys Ala Leu Pro Ala Pro Ile Glu
450                 455                 460

Lys Thr Ile Ser Lys Ala Lys Gly Gln Pro Arg Glu Pro Gln Val Tyr
465                 470                 475                 480

Thr Leu Pro Pro Ser Arg Asp Glu Leu Thr Lys Asn Gln Val Ser Leu
            485                 490                 495

Thr Cys Leu Val Lys Gly Phe Tyr Pro Ser Asp Ile Ala Val Glu Trp
            500                 505                 510

Glu Ser Asn Gly Gln Pro Glu Asn Asn Tyr Lys Thr Thr Pro Pro Val
            515                 520                 525

Leu Asp Ser Asp Gly Ser Phe Phe Leu Tyr Ser Lys Leu Thr Val Asp
530                 535                 540

Lys Ser Arg Trp Gln Gln Gly Asn Val Phe Ser Cys Ser Val Met His
545                 550                 555                 560

Glu Ala Leu His Asn His Tyr Thr Gln Lys Ser Leu Ser Leu Ser Pro
            565                 570                 575

Gly Lys

<210> SEQ ID NO 372
<211> LENGTH: 584
<212> TYPE: PRT
<213> ORGANISM: Artificial Sequence
<220> FEATURE:
<223> OTHER INFORMATION: Synthetic

<400> SEQUENCE: 372

Asp Pro Leu Pro Thr Glu Ser Arg Leu Met Asn Ser Cys Leu Gln Ala
1               5                   10                  15

Arg Arg Lys Cys Gln Ala Asp Pro Thr Cys Ser Ala Ala Tyr His His
            20                  25                  30

Leu Asp Ser Cys Thr Ser Ile Ser Thr Pro Leu Pro Ser Glu Glu
            35                  40                  45

Pro Ser Val Pro Ala Asp Cys Leu Glu Ala Ala Gln Gln Leu Arg Asn
    50                  55                  60

Ser Ser Leu Ile Gly Cys Met Cys His Arg Met Lys Asn Gln Val
65                  70                  75                  80

Ala Cys Leu Asp Ile Tyr Trp Thr Val His Arg Ala Arg Ser Leu Gly
```

-continued

```
                85                  90                  95
Asn Tyr Glu Leu Asp Val Ser Pro Tyr Glu Asp Thr Val Thr Ser Lys
            100                 105                 110

Pro Trp Lys Met Asn Leu Ser Lys Leu Asn Met Leu Lys Pro Asp Ser
            115                 120                 125

Asp Leu Cys Leu Lys Phe Ala Met Leu Cys Thr Leu Asn Asp Lys Cys
            130                 135                 140

Asp Arg Leu Arg Lys Ala Tyr Gly Glu Ala Cys Ser Gly Pro His Cys
145                 150                 155                 160

Gln Arg His Val Cys Leu Arg Gln Leu Leu Thr Phe Phe Glu Lys Ala
                165                 170                 175

Ala Glu Pro His Ala Gln Gly Leu Leu Leu Cys Pro Cys Ala Pro Asn
            180                 185                 190

Asp Arg Gly Cys Gly Glu Arg Arg Asn Thr Ile Ala Pro Asn Cys
            195                 200                 205

Ala Leu Pro Pro Val Ala Pro Asn Cys Leu Glu Leu Arg Arg Leu Cys
            210                 215                 220

Phe Ser Asp Pro Leu Cys Arg Ser Arg Leu Val Asp Phe Gln Thr His
225                 230                 235                 240

Cys His Pro Met Asp Ile Leu Gly Thr Cys Ala Thr Glu Gln Ser Arg
                245                 250                 255

Cys Leu Arg Ala Tyr Leu Gly Leu Ile Gly Thr Ala Met Thr Pro Asn
            260                 265                 270

Phe Val Ser Asn Val Asn Thr Ser Val Ala Leu Ser Cys Thr Cys Arg
            275                 280                 285

Gly Ser Gly Asn Leu Gln Glu Glu Cys Glu Met Leu Glu Gly Phe Phe
            290                 295                 300

Ser His Asn Pro Cys Leu Thr Glu Ala Ile Ala Ala Lys Met Arg Phe
305                 310                 315                 320

His Ser Gln Leu Phe Ser Gln Asp Trp Pro His Pro Thr Phe Ala Val
                325                 330                 335

Met Ala His Gln Asn Glu Asn Pro Ala Val Arg Pro Gln Pro Trp Glu
            340                 345                 350

Pro Arg Gly Pro Thr Ile Lys Pro Cys Pro Pro Cys Lys Cys Pro Ala
            355                 360                 365

Pro Asn Leu Leu Gly Gly Pro Ser Val Phe Ile Phe Pro Pro Lys Ile
            370                 375                 380

Lys Asp Val Leu Met Ile Ser Leu Ser Pro Ile Val Thr Cys Val Val
385                 390                 395                 400

Val Asp Val Ser Glu Asp Asp Pro Asp Val Gln Ile Ser Trp Phe Val
                405                 410                 415

Asn Asn Val Glu Val His Thr Ala Gln Thr Gln Thr His Arg Glu Asp
            420                 425                 430

Tyr Asn Ser Thr Leu Arg Val Val Ser Ala Leu Pro Ile Gln His Gln
            435                 440                 445

Asp Trp Met Ser Gly Lys Glu Phe Lys Cys Lys Val Asn Asn Lys Asp
            450                 455                 460

Leu Pro Ala Pro Ile Glu Arg Thr Ile Ser Lys Pro Lys Gly Ser Val
465                 470                 475                 480

Arg Ala Pro Gln Val Tyr Val Leu Pro Pro Pro Glu Glu Glu Met Thr
                485                 490                 495

Lys Lys Gln Val Thr Leu Thr Cys Met Val Thr Asp Phe Met Pro Glu
            500                 505                 510
```

```
Asp Ile Tyr Val Glu Trp Thr Asn Asn Gly Lys Thr Glu Leu Asn Tyr
            515                 520                 525

Lys Asn Thr Glu Pro Val Leu Asp Ser Asp Gly Ser Tyr Phe Met Tyr
530                 535                 540

Ser Lys Leu Arg Val Glu Lys Lys Asn Trp Val Glu Arg Asn Ser Tyr
545                 550                 555                 560

Ser Cys Ser Val Val His Glu Gly Leu His Asn His Thr Thr Lys
            565                 570                 575

Ser Phe Ser Arg Thr Pro Gly Lys
            580

<210> SEQ ID NO 373
<211> LENGTH: 371
<212> TYPE: PRT
<213> ORGANISM: Artificial Sequence
<220> FEATURE:
<223> OTHER INFORMATION: Synthetic

<400> SEQUENCE: 373

Asp Pro Leu Pro Thr Glu Ser Arg Leu Met Asn Ser Cys Leu Gln Ala
1               5                   10                  15

Arg Arg Lys Cys Gln Ala Asp Pro Ile Cys Ser Ala Ala Tyr His His
            20                  25                  30

Leu Asp Ser Cys Thr Ser Ser Ile Ser Thr Pro Leu Pro Ser Glu Glu
            35                  40                  45

Pro Ser Val Pro Ala Asp Cys Leu Glu Ala Ala Gln Gln Leu Arg Asn
50                  55                  60

Ser Ser Leu Ile Gly Cys Met Cys His Arg Arg Met Lys Asn Gln Val
65                  70                  75                  80

Ala Cys Leu Asp Ile Tyr Trp Thr Val His Arg Ala Arg Ser Leu Gly
                85                  90                  95

Asn Tyr Glu Leu Asp Val Ser Pro Tyr Glu Asp Thr Val Thr Ser Lys
            100                 105                 110

Pro Trp Lys Met Asn Leu Ser Lys Leu Asn Met Leu Lys Pro Asp Ser
            115                 120                 125

Asp Leu Cys Leu Lys Phe Ala Met Leu Cys Thr Leu Asn Asp Lys Cys
130                 135                 140

Asp Arg Leu Arg Lys Ala Tyr Gly Glu Ala Cys Ser Gly Pro His Cys
145                 150                 155                 160

Gln Arg His Val Cys Leu Arg Gln Leu Leu Thr Phe Phe Glu Lys Ala
                165                 170                 175

Ala Glu Pro His Ala Gln Gly Leu Leu Leu Cys Pro Cys Ala Pro Asn
            180                 185                 190

Asp Arg Gly Cys Gly Glu Arg Arg Arg Asn Thr Ile Ala Pro Ser Cys
            195                 200                 205

Ala Leu Pro Pro Val Ala Pro Asn Cys Leu Glu Leu Arg Arg Leu Cys
210                 215                 220

Phe Ser Asp Pro Leu Cys Arg Ser Arg Leu Val Asp Phe Gln Thr His
225                 230                 235                 240

Cys His Pro Met Asp Ile Leu Gly Thr Cys Ala Thr Glu Gln Ser Arg
                245                 250                 255

Cys Leu Arg Ala Tyr Leu Gly Leu Ile Gly Thr Ala Met Thr Pro Asn
            260                 265                 270

Phe Val Ser Asn Val Asn Thr Ser Val Ala Leu Ser Cys Thr Cys Arg
            275                 280                 285
```

```
Gly Ser Gly Asn Leu Gln Glu Glu Cys Glu Gln Leu Glu Gly Phe Phe
    290                 295                 300

Ser His Asn Pro Cys Leu Thr Glu Ala Ile Ala Ala Lys Met Arg Phe
305                 310                 315                 320

His Ser Gln Leu Phe Tyr Gln Asp Trp Pro His Pro Thr Phe Ala Val
                325                 330                 335

Met Ala His Gln Asn Glu Asn Glu Gln Lys Leu Ile Ser Glu Glu Asp
            340                 345                 350

Leu Gly Gly Glu Gln Lys Leu Ile Ser Glu Glu Asp Leu His His His
        355                 360                 365

His His His
    370

<210> SEQ ID NO 374
<211> LENGTH: 1200
<212> TYPE: DNA
<213> ORGANISM: Homo sapiens

<400> SEQUENCE: 374
atggtgcgcc ccctgaaccc gcgaccgctg ccgcccgtag tcctgatgtt gctgctgctg      60
ctgccgccgt cgccgctgcc tctcgcagcc ggagaccccc ttcccacaga aagccgactc     120
atgaacagct gtctccaggc caggaggaag tgccaggctg atcccacctg cagtgctgcc     180
taccaccacc tggattcctg cacctctagc ataagcaccc actgccctc agaggagcct      240 tcggtccctg ctgactgcct ggaggcagca cagcaactca ggaacagctc tctgataggc     300
tgcatgtgcc accggcgcat gaagaaccag gttgcctgct ggacatcta ttggaccgtt      360 caccgtgccc gcagccttgg taactatgag ctggatgtct cccctatga agacacagtg      420 accagcaaac cctggaaaat gaatctcagc aaactgaaca tgctcaaacc agactcagac     480
ctctgcctca gtttgccat gctgtgtact ctcaatgaca gtgtgaccg gctgcgcaag       540 gcctacgggg aggcgtgctc cgggccccac tgccagcgcc acgtctgcct caggcagctg     600
ctcactttct tcgagaaggc cgccgagccc acgcgcagg gcctgctact gtgcccatgt      660 gccccccaacg accggggctg cggggagcgc cggcgcaaca ccatcgcccc caactgcgcg    720
ctgccgcctg tggcccccaa ctgcctggag ctgcggcgcc tctgcttctc cgacccgctt    780
tgcagatcac gcctggtgga tttccagacc cactgccatc ccatggacat cctaggaact    840
tgtgcaacag agcagtccag atgtctacga gcatacctgg ggctgattgg gactgccatg   900 accccccaact tgtcagcaa tgtcaacacc agtgttgcct aagctgcac ctgccgaggc     960 agtggcaacc tgcaggagga gtgtgaaatg ctggaagggt tcttctccca aacccctgc   1020 ctcacggagg ccattgcagc taagatgcgt tttcacagcc aactcttctc ccaggactgg   1080
ccacacccta cctttgctgt gatggcacac cagaatgaaa accctgctgt gaggccacag   1140
ccctgggtgc cctctctttt ctcctgcacg cttcccttga ttctgctcct gagcctatgg   1200

<210> SEQ ID NO 375
<211> LENGTH: 400
<212> TYPE: PRT
<213> ORGANISM: Homo sapiens

<400> SEQUENCE: 375

Met Val Arg Pro Leu Asn Pro Arg Pro Leu Pro Pro Val Val Leu Met
  1               5                  10                  15

Leu Leu Leu Leu Leu Pro Pro Ser Pro Leu Pro Leu Ala Ala Gly Asp
```

|   |   |   | 20  |   |   |   | 25  |   |   |   | 30  |   |   |
|---|---|---|-----|---|---|---|-----|---|---|---|-----|---|---|

Pro Leu Pro Thr Glu Ser Arg Leu Met Asn Ser Cys Leu Gln Ala Arg
            35                  40                  45

Arg Lys Cys Gln Ala Asp Pro Thr Cys Ser Ala Ala Tyr His His Leu
 50                  55                  60

Asp Ser Cys Thr Ser Ser Ile Ser Thr Pro Leu Pro Ser Glu Glu Pro
 65                  70                  75                  80

Ser Val Pro Ala Asp Cys Leu Glu Ala Ala Gln Gln Leu Arg Asn Ser
                85                  90                  95

Ser Leu Ile Gly Cys Met Cys His Arg Arg Met Lys Asn Gln Val Ala
            100                 105                 110

Cys Leu Asp Ile Tyr Trp Thr Val His Arg Ala Arg Ser Leu Gly Asn
            115                 120                 125

Tyr Glu Leu Asp Val Ser Pro Tyr Glu Asp Thr Val Thr Ser Lys Pro
            130                 135                 140

Trp Lys Met Asn Leu Ser Lys Leu Asn Met Leu Lys Pro Asp Ser Asp
145                 150                 155                 160

Leu Cys Leu Lys Phe Ala Met Leu Cys Thr Leu Asn Asp Lys Cys Asp
                165                 170                 175

Arg Leu Arg Lys Ala Tyr Gly Glu Ala Cys Ser Gly Pro His Cys Gln
            180                 185                 190

Arg His Val Cys Leu Arg Gln Leu Leu Thr Phe Phe Glu Lys Ala Ala
            195                 200                 205

Glu Pro His Ala Gln Gly Leu Leu Leu Cys Pro Cys Ala Pro Asn Asp
            210                 215                 220

Arg Gly Cys Gly Glu Arg Arg Asn Thr Ile Ala Pro Asn Cys Ala
225                 230                 235                 240

Leu Pro Pro Val Ala Pro Asn Cys Leu Glu Leu Arg Arg Leu Cys Phe
                245                 250                 255

Ser Asp Pro Leu Cys Arg Ser Arg Leu Val Asp Phe Gln Thr His Cys
            260                 265                 270

His Pro Met Asp Ile Leu Gly Thr Cys Ala Thr Glu Gln Ser Arg Cys
            275                 280                 285

Leu Arg Ala Tyr Leu Gly Leu Ile Gly Thr Ala Met Thr Pro Asn Phe
            290                 295                 300

Val Ser Asn Val Asn Thr Ser Val Ala Leu Ser Cys Thr Cys Arg Gly
305                 310                 315                 320

Ser Gly Asn Leu Gln Glu Glu Cys Glu Met Leu Glu Gly Phe Phe Ser
                325                 330                 335

His Asn Pro Cys Leu Thr Glu Ala Ile Ala Ala Lys Met Arg Phe His
            340                 345                 350

Ser Gln Leu Phe Ser Gln Asp Trp Pro His Pro Thr Phe Ala Val Met
            355                 360                 365

Ala His Gln Asn Glu Asn Pro Ala Val Arg Pro Gln Pro Trp Val Pro
            370                 375                 380

Ser Leu Phe Ser Cys Thr Leu Pro Leu Ile Leu Leu Ser Leu Trp
385                 390                 395                 400

<210> SEQ ID NO 376
<211> LENGTH: 632
<212> TYPE: PRT
<213> ORGANISM: Homo sapiens

<400> SEQUENCE: 376

-continued

```
Asp Arg Leu Asp Cys Val Lys Ala Ser Asp Gln Cys Leu Lys Glu Gln
1               5                   10                  15

Ser Cys Ser Thr Lys Tyr Arg Thr Leu Arg Gln Cys Val Ala Gly Lys
            20                  25                  30

Glu Thr Asn Phe Ser Leu Ala Ser Gly Leu Glu Ala Lys Asp Glu Cys
                35                  40                  45

Arg Ser Ala Met Glu Ala Leu Lys Gln Lys Ser Leu Tyr Asn Cys Arg
            50                  55                  60

Cys Lys Arg Gly Met Lys Lys Glu Lys Asn Cys Leu Arg Ile Tyr Trp
65                  70                  75                  80

Ser Met Tyr Gln Ser Leu Gln Gly Asn Asp Leu Leu Glu Asp Ser Pro
                85                  90                  95

Tyr Glu Pro Val Asn Ser Arg Leu Ser Asp Ile Phe Arg Val Val Pro
                100                 105                 110

Phe Ile Ser Asp Val Phe Gln Gln Val Glu His Ile Pro Lys Gly Asn
                115                 120                 125

Asn Cys Leu Asp Ala Ala Lys Ala Cys Asn Leu Asp Asp Ile Cys Lys
            130                 135                 140

Lys Tyr Arg Ser Ala Tyr Ile Thr Pro Cys Thr Thr Ser Val Ser Asn
145                 150                 155                 160

Asp Val Cys Asn Arg Arg Lys Cys His Lys Ala Leu Arg Gln Phe Phe
                165                 170                 175

Asp Lys Val Pro Ala Lys His Ser Tyr Gly Met Leu Phe Cys Ser Cys
                180                 185                 190

Arg Asp Ile Ala Cys Thr Glu Arg Arg Arg Gln Thr Ile Val Pro Val
            195                 200                 205

Cys Ser Tyr Glu Glu Arg Glu Lys Pro Asn Cys Leu Asn Leu Gln Asp
            210                 215                 220

Ser Cys Lys Thr Asn Tyr Ile Cys Arg Ser Arg Leu Ala Asp Phe Phe
225                 230                 235                 240

Thr Asn Cys Gln Pro Glu Ser Arg Ser Val Ser Ser Cys Leu Lys Glu
                245                 250                 255

Asn Tyr Ala Asp Cys Leu Leu Ala Tyr Ser Gly Leu Ile Gly Thr Val
                260                 265                 270

Met Thr Pro Asn Tyr Ile Asp Ser Ser Leu Ser Val Ala Pro Trp
                275                 280                 285

Cys Asp Cys Ser Asn Ser Gly Asn Asp Leu Glu Glu Cys Leu Lys Phe
            290                 295                 300

Leu Asn Phe Phe Lys Asp Asn Thr Cys Leu Lys Asn Ala Ile Gln Ala
305                 310                 315                 320

Phe Gly Asn Gly Ser Asp Val Thr Val Trp Gln Pro Ala Phe Pro Val
                325                 330                 335

Gln Thr Thr Thr Ala Thr Thr Thr Ala Leu Arg Val Lys Asn Lys
            340                 345                 350

Pro Leu Gly Pro Ala Gly Ser Glu Asn Glu Ile Pro Thr His Val Leu
            355                 360                 365

Pro Pro Cys Ala Asn Leu Gln Ala Gln Lys Leu Lys Ser Asn Val Ser
            370                 375                 380

Gly Asn Thr His Leu Cys Ile Ser Asn Gly Asn Tyr Glu Lys Glu Gly
385                 390                 395                 400

Leu Gly Ala Ser Ser Asp Lys Thr His Thr Cys Pro Pro Cys Pro Ala
                405                 410                 415

Pro Glu Leu Leu Gly Gly Pro Ser Val Phe Leu Phe Pro Pro Lys Pro
```

```
              420                 425                 430
Lys Asp Thr Leu Met Ile Ser Arg Thr Pro Glu Val Thr Cys Val Val
            435                 440                 445

Val Asp Val Ser His Glu Asp Pro Glu Val Lys Phe Asn Trp Tyr Val
        450                 455                 460

Asp Gly Val Glu Val His Asn Ala Lys Thr Lys Pro Arg Glu Glu Gln
465                 470                 475                 480

Tyr Asn Ser Thr Tyr Arg Val Val Ser Val Leu Thr Val Leu His Gln
                485                 490                 495

Asp Trp Leu Asn Gly Lys Glu Tyr Lys Cys Lys Val Ser Asn Lys Ala
            500                 505                 510

Leu Pro Ala Pro Ile Glu Lys Thr Ile Ser Lys Ala Lys Gly Gln Pro
        515                 520                 525

Arg Glu Pro Gln Val Tyr Thr Leu Pro Pro Ser Arg Asp Glu Leu Thr
    530                 535                 540

Lys Asn Gln Val Ser Leu Thr Cys Leu Val Lys Gly Phe Tyr Pro Ser
545                 550                 555                 560

Asp Ile Ala Val Glu Trp Glu Ser Asn Gly Gln Pro Glu Asn Asn Tyr
                565                 570                 575

Lys Thr Thr Pro Pro Val Leu Asp Ser Asp Gly Ser Phe Phe Leu Tyr
            580                 585                 590

Ser Lys Leu Thr Val Asp Lys Ser Arg Trp Gln Gln Gly Asn Val Phe
        595                 600                 605

Ser Cys Ser Val Met His Glu Ala Leu His Asn His Tyr Thr Gln Lys
    610                 615                 620

Ser Leu Ser Leu Ser Pro Gly Lys
625                 630

<210> SEQ ID NO 377
<211> LENGTH: 405
<212> TYPE: PRT
<213> ORGANISM: Artificial Sequence
<220> FEATURE:
<223> OTHER INFORMATION: Cynomolgus GFRalpha3: cerebellum cDNA

<400> SEQUENCE: 377

Met Val Arg Pro Pro Ser Pro Arg Pro Leu Pro Pro Val Val Leu Met
1               5                   10                  15

Leu Leu Leu Leu Leu Leu Leu Leu Leu Pro Pro Ser Pro Leu Pro
                20                  25                  30

Leu Ala Ala Gly Asp Pro Leu Pro Thr Glu Ser Arg Leu Met Asn Ser
            35                  40                  45

Cys Leu Gln Ala Arg Arg Lys Cys Gln Ala Asp Pro Ile Cys Ser Ala
    50                  55                  60

Ala Tyr His His Leu Asp Ser Cys Thr Ser Ser Ile Ser Thr Pro Leu
65                  70                  75                  80

Pro Ser Glu Glu Pro Ser Val Pro Ala Asp Cys Leu Glu Ala Ala Gln
                85                  90                  95

Gln Leu Arg Asn Ser Ser Leu Ile Gly Cys Met Cys His Arg Arg Met
            100                 105                 110

Lys Asn Gln Val Ala Cys Leu Asp Ile Tyr Trp Thr Val His Arg Ala
        115                 120                 125

Arg Ser Leu Gly Asn Tyr Glu Leu Asp Val Ser Pro Tyr Glu Asp Thr
    130                 135                 140

Val Thr Ser Lys Pro Trp Lys Met Asn Leu Ser Lys Leu Asn Met Leu
```

```
                145                 150                 155                 160
Lys Pro Asp Ser Asp Leu Cys Leu Lys Phe Ala Met Leu Cys Thr Leu
                165                 170                 175

Asn Asp Lys Cys Asp Arg Leu Arg Lys Ala Tyr Gly Glu Ala Cys Ser
                180                 185                 190

Gly Pro His Cys Gln Arg His Val Cys Leu Arg Gln Leu Leu Thr Phe
                195                 200                 205

Phe Glu Lys Ala Ala Glu Pro His Ala Gln Gly Leu Leu Leu Cys Pro
                210                 215                 220

Cys Ala Pro Asn Asp Arg Gly Cys Gly Glu Arg Arg Arg Asn Thr Ile
225                 230                 235                 240

Ala Pro Ser Cys Ala Leu Pro Pro Val Ala Pro Asn Cys Leu Glu Leu
                245                 250                 255

Arg Arg Leu Cys Phe Ser Asp Pro Leu Cys Arg Ser Arg Leu Val Asp
                260                 265                 270

Phe Gln Thr His Cys His Pro Met Asp Ile Leu Gly Thr Cys Ala Thr
                275                 280                 285

Glu Gln Ser Arg Cys Leu Arg Ala Tyr Leu Gly Leu Ile Gly Thr Ala
                290                 295                 300

Met Thr Pro Asn Phe Val Ser Asn Val Asn Thr Ser Val Ala Leu Ser
305                 310                 315                 320

Cys Thr Cys Arg Gly Ser Gly Asn Leu Gln Glu Glu Cys Glu Gln Leu
                325                 330                 335

Glu Gly Phe Phe Ser His Asn Pro Cys Leu Thr Glu Ala Ile Ala Ala
                340                 345                 350

Lys Met Arg Phe His Ser Gln Leu Phe Tyr Gln Asp Trp Pro His Pro
                355                 360                 365

Thr Phe Ala Val Met Ala His Gln Asn Glu Asn Arg Ala Leu Arg Ser
                370                 375                 380

Lys Pro Trp Ala Pro Ser Leu Phe Ser Cys Thr Leu Pro Leu Ile Leu
385                 390                 395                 400

Leu Leu Ser Leu Trp
                405

<210> SEQ ID NO 378
<211> LENGTH: 1086
<212> TYPE: PRT
<213> ORGANISM: Artificial Sequence
<220> FEATURE:
<223> OTHER INFORMATION: Cynomolgus RET without signal sequence

<400> SEQUENCE: 378

Leu Tyr Phe Ser Arg Asp Ala Tyr Trp Glu Lys Leu Tyr Val Asp Gln
1                   5                   10                  15

Pro Ala Gly Thr Pro Leu Leu Tyr Val His Ala Leu Arg Asp Ala Pro
                20                  25                  30

Glu Glu Val Pro Ser Phe Arg Leu Gly Gln His Leu Tyr Gly Thr Tyr
            35                  40                  45

Arg Thr Arg Leu His Glu Asn Asn Trp Ile Cys Ile Gln Glu Asp Thr
        50                  55                  60

Gly Leu Leu Tyr Leu Asn Arg Ser Leu Asp Ser Ser Trp Glu Lys
65                  70                  75                  80

Leu Ser Gly Arg Asn Arg Gly Phe Pro Leu Leu Thr Val Tyr Leu Lys
                85                  90                  95

Val Phe Leu Ser Pro Thr Ser Leu Arg Glu Gly Glu Cys Gln Trp Pro
```

```
            100                 105                 110
Gly Cys Ala Arg Val Tyr Phe Ser Phe Phe Asn Thr Ser Phe Pro Ala
            115                 120                 125
Cys Thr Ser Leu Lys Pro Arg Glu Leu Cys Phe Pro Glu Thr Arg Pro
            130                 135                 140
Ser Phe Arg Ile Arg Glu Asn Arg Pro Pro Gly Thr Phe His Gln Phe
145                 150                 155                 160
Arg Leu Leu Pro Val Gln Phe Leu Cys Pro Asn Ile Ser Val Ala Tyr
            165                 170                 175
Arg Leu Leu Glu Gly Glu Gly Leu Pro Phe Arg Cys Ala Pro Asp Ser
            180                 185                 190
Leu Glu Val Ser Thr Arg Trp Ala Leu Asp Arg Glu Gln Arg Glu Lys
            195                 200                 205
Tyr Glu Leu Val Ala Val Cys Thr Val His Ala Gly Ala Arg Glu Glu
            210                 215                 220
Val Val Met Val Pro Phe Pro Val Thr Val Tyr Asp Glu Asp Asp Ser
225                 230                 235                 240
Ala Pro Thr Phe Pro Ala Gly Val Asp Thr Ala Ser Ala Val Val Glu
            245                 250                 255
Phe Lys Arg Lys Glu Asp Thr Val Val Ala Thr Leu Arg Val Phe Asp
            260                 265                 270
Ala Asp Val Val Pro Ala Ser Gly Glu Leu Val Arg Arg Tyr Thr Ser
            275                 280                 285
Thr Leu Leu Pro Gly Asp Thr Trp Thr Gln Gln Thr Phe Arg Val Glu
            290                 295                 300
His Trp Pro Asn Glu Thr Ser Val Gln Ala Asn Gly Ser Phe Val Arg
305                 310                 315                 320
Ala Thr Val His Asp Tyr Arg Leu Val Leu Asn Arg Asn Leu Ser Ile
            325                 330                 335
Ser Glu Asn Arg Thr Met Gln Leu Ala Val Leu Val Asn Asp Ser Asp
            340                 345                 350
Phe Gln Gly Pro Gly Ala Gly Val Leu Leu Leu His Phe Asn Val Ser
            355                 360                 365
Val Leu Pro Val Ser Leu His Leu Pro Ser Ser Tyr Ser Leu Ser Val
            370                 375                 380
Ser Arg Arg Ala Arg Arg Phe Ala Gln Ile Gly Lys Val Cys Val Glu
385                 390                 395                 400
Asn Cys Gln Ala Phe Ser Gly Ile Asn Val Gln Tyr Glu Leu His Ser
            405                 410                 415
Ser Gly Ala Asn Cys Ser Thr Leu Gly Val Val Thr Ser Ala Glu Asp
            420                 425                 430
Thr Ser Gly Ile Leu Phe Val Asn Asp Thr Lys Ala Leu Arg Arg Pro
            435                 440                 445
Lys Cys Ala Glu Leu His Tyr Met Val Val Ala Thr Asn His Gln Thr
            450                 455                 460
Ser Arg Gln Ala Gln Ala Gln Leu Leu Val Thr Val Glu Gly Leu Tyr
465                 470                 475                 480
Val Ala Glu Glu Ala Gly Cys Pro Leu Ser Cys Ala Val Ser Lys Arg
            485                 490                 495
Arg Pro Glu Cys Glu Glu Cys Gly Gly Leu Gly Ser Pro Thr Gly Arg
            500                 505                 510
Cys Glu Trp Arg Gln Gly Asp Gly Lys Gly Ile Thr Arg Asn Phe Ser
            515                 520                 525
```

```
Thr Cys Ser Pro Ser Thr Lys Thr Cys Pro Asp Gly His Cys Asp Val
    530                 535                 540
Val Glu Thr Gln Asp Ile Asn Ile Cys Pro Gln Asp Cys Leu Arg Gly
545                 550                 555                 560
Ser Ile Val Gly Gly His Glu Pro Gly Glu Pro Arg Gly Ile Lys Ala
                565                 570                 575
Gly Tyr Gly Thr Cys Asn Cys Phe Pro Glu Glu Lys Cys Phe Cys
                580                 585                 590
Glu Pro Glu Asp Ile Gln Asp Pro Leu Cys Asp Glu Leu Cys Arg Thr
            595                 600                 605
Val Ile Ala Ala Val Leu Phe Ser Phe Ile Val Ser Val Leu Leu
    610                 615                 620
Ser Ala Phe Cys Ile His Arg Tyr His Lys Phe Ala His Lys Pro Pro
625                 630                 635                 640
Ile Pro Ser Ala Glu Met Thr Phe Arg Arg Pro Ala Gln Ala Phe Pro
                645                 650                 655
Val Ser Tyr Ser Ser Ser Gly Ala Arg Arg Pro Ser Leu Asp Ser Met
                660                 665                 670
Glu Asn Gln Val Ser Val Asp Ala Phe Lys Ile Pro Glu Asp Pro Lys
            675                 680                 685
Trp Glu Phe Pro Arg Lys Asn Leu Val Leu Gly Lys Thr Leu Gly Glu
    690                 695                 700
Gly Glu Phe Gly Lys Val Val Lys Ala Thr Ala Phe Arg Leu Lys Gly
705                 710                 715                 720
Arg Ala Gly Tyr Thr Thr Val Ala Val Lys Met Leu Lys Glu Asn Ala
                725                 730                 735
Ser Pro Ser Glu Leu Arg Asp Leu Leu Ser Glu Phe Asn Leu Leu Lys
                740                 745                 750
Gln Val Asn His Pro His Val Ile Lys Leu Tyr Gly Ala Cys Ser Gln
            755                 760                 765
Asp Gly Pro Leu Leu Leu Ile Val Glu Tyr Ala Lys Tyr Gly Ser Leu
    770                 775                 780
Arg Gly Phe Leu Arg Glu Ser Arg Lys Val Gly Pro Gly Tyr Leu Gly
785                 790                 795                 800
Ser Gly Gly Ser Arg Asn Ser Ser Ser Leu Asp His Pro Asp Glu Arg
                805                 810                 815
Ala Leu Thr Met Gly Asp Leu Ile Ser Phe Ala Trp Gln Ile Ser Arg
                820                 825                 830
Gly Met Gln Tyr Leu Ala Glu Met Lys Leu Val His Arg Asp Leu Ala
            835                 840                 845
Ala Arg Asn Ile Leu Val Ala Glu Gly Arg Lys Met Lys Ile Ser Asp
    850                 855                 860
Phe Gly Leu Ser Arg Asp Val Tyr Glu Glu Asp Ser Tyr Val Lys Arg
865                 870                 875                 880
Ser Lys Gly Arg Ile Pro Val Lys Trp Met Ala Ile Glu Ser Leu Phe
                885                 890                 895
Asp His Ile Tyr Thr Thr Gln Ser Asp Val Trp Ser Phe Gly Val Leu
            900                 905                 910
Leu Trp Glu Ile Val Thr Leu Gly Gly Asn Pro Tyr Pro Gly Ile Pro
    915                 920                 925
Pro Glu Arg Leu Phe Asn Leu Leu Lys Thr Gly His Arg Met Glu Arg
930                 935                 940
```

```
Pro Asp Asn Cys Ser Glu Glu Met Tyr Arg Leu Met Leu Gln Cys Trp
945                 950                 955                 960

Lys Gln Glu Pro Asp Lys Arg Pro Val Phe Ala Asp Ile Ser Lys Asp
            965                 970                 975

Leu Glu Lys Met Met Val Lys Ser Arg Asp Tyr Leu Asp Leu Ala Ala
            980                 985                 990

Ser Thr Pro Ser Asp Ser Leu Leu Tyr Asp Asp Gly Leu Ser Glu Glu
            995                 1000                1005

Glu Thr Pro Leu Val Asp Cys Asn Asn Ala Pro Leu Pro Arg Ala Leu
    1010                1015                1020

Pro Ser Thr Trp Ile Glu Asn Lys Leu Tyr Gly Met Ser Asp Pro Asn
1025                1030                1035                1040

Trp Pro Gly Glu Ser Pro Val Pro Leu Thr Arg Ala Asp Gly Thr Asn
            1045                1050                1055

Thr Gly Phe Pro Arg Tyr Ala Asn Asp Ser Val Tyr Ala Asn Trp Met
            1060                1065                1070

Leu Ser Pro Ser Ala Ala Lys Leu Met Asp Thr Phe Asp Ser
            1075                1080                1085

<210> SEQ ID NO 379
<211> LENGTH: 371
<212> TYPE: PRT
<213> ORGANISM: Artificial Sequence
<220> FEATURE:
<223> OTHER INFORMATION: Mouse GFRalpha3-MMH
      aa 1-343: N29-N371 of Ac. No. AAH66202.1
      aa 344-371: myc-GG linker-myc-hexahistidine tag

<400> SEQUENCE: 379

Asn Ser Leu Ala Thr Glu Asn Arg Phe Val Asn Ser Cys Thr Gln Ala
1               5                   10                  15

Arg Lys Lys Cys Glu Ala Asn Pro Ala Cys Lys Ala Ala Tyr Gln His
            20                  25                  30

Leu Gly Ser Cys Thr Ser Ser Leu Ser Arg Pro Leu Pro Leu Glu Glu
        35                  40                  45

Ser Ala Met Ser Ala Asp Cys Leu Glu Ala Ala Glu Gln Leu Arg Asn
50                  55                  60

Ser Ser Leu Ile Asp Cys Arg Cys His Arg Arg Met Lys His Gln Ala
65                  70                  75                  80

Thr Cys Leu Asp Ile Tyr Trp Thr Val His Pro Ala Arg Ser Leu Gly
                85                  90                  95

Asp Tyr Glu Leu Asp Val Ser Pro Tyr Glu Asp Thr Val Thr Ser Lys
            100                 105                 110

Pro Trp Lys Met Asn Leu Ser Lys Leu Asn Met Leu Lys Pro Asp Ser
        115                 120                 125

Asp Leu Cys Leu Lys Phe Ala Met Leu Cys Thr Leu His Asp Lys Cys
130                 135                 140

Asp Arg Leu Arg Lys Ala Tyr Gly Glu Ala Cys Ser Gly Ile Arg Cys
145                 150                 155                 160

Gln Arg His Leu Cys Leu Ala Gln Leu Arg Ser Phe Phe Glu Lys Ala
                165                 170                 175

Ala Glu Ser His Ala Gln Gly Leu Leu Leu Cys Pro Cys Ala Pro Glu
            180                 185                 190

Asp Ala Gly Cys Gly Glu Arg Arg Arg Asn Thr Ile Ala Pro Ser Cys
        195                 200                 205

Ala Leu Pro Ser Val Thr Pro Asn Cys Leu Asp Leu Arg Ser Phe Cys
```

Arg Ala Asp Pro Leu Cys Arg Ser Arg Leu Met Asp Phe Gln Thr His
225                 230                 235                 240

Cys His Pro Met Asp Ile Leu Gly Thr Cys Ala Thr Glu Gln Ser Arg
            245                 250                 255

Cys Leu Arg Ala Tyr Leu Gly Leu Ile Gly Thr Ala Met Thr Pro Asn
            260                 265                 270

Phe Ile Ser Lys Val Asn Thr Thr Val Ala Leu Ser Cys Ser Cys Arg
            275                 280                 285

Gly Ser Gly Asn Leu Gln Asp Glu Cys Glu Gln Leu Glu Arg Ser Phe
        290                 295                 300

Ser Gln Asn Pro Cys Leu Val Glu Ala Ile Ala Ala Lys Met Arg Phe
305                 310                 315                 320

His Arg Gln Leu Phe Ser Gln Asp Trp Ala Asp Ser Thr Phe Ser Val
                325                 330                 335

Val Gln Gln Gln Asn Ser Asn Glu Gln Lys Leu Ile Ser Glu Glu Asp
            340                 345                 350

Leu Gly Gly Glu Gln Lys Leu Ile Ser Glu Glu Asp Leu His His His
        355                 360                 365

His His His
    370

<210> SEQ ID NO 380
<211> LENGTH: 372
<212> TYPE: DNA
<213> ORGANISM: Artificial Sequence
<220> FEATURE:
<223> OTHER INFORMATION: synthetic

<400> SEQUENCE: 380
caggttcaac tggtgcagtc tggagctgag gtgaagaagc ctggggcctc agtgaaggtc      60
tcctgcaagg cttctggtta cacctttacc agctatggta tcatctgggt gcgacaggcc    120
cctggacaag gcttgagtg atgggatgg atcagcggtt acaatggtaa cacaaactat      180
acacagaatc tccagggcag agtcaccatg accacagaca cttccacgac acagcctac    240 atggagctga ggagcctgag atctgacgac acggccgtgt attactgtgc gagatggggt    300
atagcaactc gtccctacta ctactacggt atggacgtct ggggccaagg gaccacggtc    360
accgtctcct ca                                                         372

<210> SEQ ID NO 381
<211> LENGTH: 124
<212> TYPE: PRT
<213> ORGANISM: Artificial Sequence
<220> FEATURE:
<223> OTHER INFORMATION: synthetic

<400> SEQUENCE: 381

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ile Trp Val Arg Gln Ala Pro Gly Gln Gly Leu Glu Trp Met
        35                  40                  45

Gly Trp Ile Ser Gly Tyr Asn Gly Asn Thr Asn Tyr Thr Gln Asn Leu
    50                  55                  60

Gln Gly Arg Val Thr Met Thr Thr Asp Thr Ser Thr Thr Thr Ala Tyr

```
              65                  70                  75                  80
Met Glu Leu Arg Ser Leu Arg Ser Asp Asp Thr Ala Val Tyr Tyr Cys
                    85                  90                  95

Ala Arg Trp Gly Ile Ala Thr Arg Pro Tyr Tyr Tyr Gly Met Asp
            100                 105                 110

Val Trp Gly Gln Gly Thr Thr Val Thr Val Ser Ser
        115                 120
```

<210> SEQ ID NO 382
<211> LENGTH: 24
<212> TYPE: DNA
<213> ORGANISM: Artificial Sequence
<220> FEATURE:
<223> OTHER INFORMATION: synthetic

<400> SEQUENCE: 382
ggttacaccT ttaccagcta tggt                                          24

<210> SEQ ID NO 383
<211> LENGTH: 8
<212> TYPE: PRT
<213> ORGANISM: Artificial Sequence
<220> FEATURE:
<223> OTHER INFORMATION: synthetic

<400> SEQUENCE: 383

Gly Tyr Thr Phe Thr Ser Tyr Gly
 1               5

<210> SEQ ID NO 384
<211> LENGTH: 24
<212> TYPE: DNA
<213> ORGANISM: Artificial Sequence
<220> FEATURE:
<223> OTHER INFORMATION: synthetic

<400> SEQUENCE: 384
atcagcggtt acaatggtaa caca                                          24

<210> SEQ ID NO 385
<211> LENGTH: 8
<212> TYPE: PRT
<213> ORGANISM: Artificial Sequence
<220> FEATURE:
<223> OTHER INFORMATION: synthetic

<400> SEQUENCE: 385

Ile Ser Gly Tyr Asn Gly Asn Thr
 1               5

<210> SEQ ID NO 386
<211> LENGTH: 51
<212> TYPE: DNA
<213> ORGANISM: Artificial Sequence
<220> FEATURE:
<223> OTHER INFORMATION: synthetic

<400> SEQUENCE: 386
gcgagatggg gtatagcaac tcgtccctac tactactacg gtatggacgt c            51

<210> SEQ ID NO 387
<211> LENGTH: 17
<212> TYPE: PRT
<213> ORGANISM: Artificial Sequence
<220> FEATURE:

<223> OTHER INFORMATION: synthetic

<400> SEQUENCE: 387

Ala Arg Trp Gly Ile Ala Thr Arg Pro Tyr Tyr Tyr Gly Met Asp
1               5                   10                  15
Val

<210> SEQ ID NO 388
<211> LENGTH: 321
<212> TYPE: DNA
<213> ORGANISM: Artificial Sequence
<220> FEATURE:
<223> OTHER INFORMATION: synthetic

<400> SEQUENCE: 388

```
gacatccaga tgacccagtc tccatcctca ctgtctgcat ctgtaggaga cagagtcacc    60
atcacttgtc gggcgagtca ggacattacc aattatttag cctggtttca gcagaaacca   120
gggaaagccc ctaagtccct gatctatgct gcatccagtt tgcaaagtgg ggtcccatca   180
aagttcagcg gcagtggatc tgggacagat ttcactctca ccatcagcag cctgcagcct   240
gaagattttg caacttatta ctgccaacag tataatagtt accctcccac tttcggccct   300
gggaccaaag tggatatcaa a                                             321
```

<210> SEQ ID NO 389
<211> LENGTH: 107
<212> TYPE: PRT
<213> ORGANISM: Artificial Sequence
<220> FEATURE:
<223> OTHER INFORMATION: synthetic

<400> SEQUENCE: 389

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Thr Asn Tyr
            20                  25                  30
Leu Ala Trp Phe Gln Gln Lys Pro Gly Lys Ala Pro Lys Ser Leu Ile
        35                  40                  45
Tyr Ala Ala Ser Ser Leu Gln Ser Gly Val Pro Ser Lys Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Asn Ser Tyr Pro Pro
                85                  90                  95
Thr Phe Gly Pro Gly Thr Lys Val Asp Ile Lys
            100                 105

<210> SEQ ID NO 390
<211> LENGTH: 18
<212> TYPE: DNA
<213> ORGANISM: Artificial Sequence
<220> FEATURE:
<223> OTHER INFORMATION: synthetic

<400> SEQUENCE: 390
caggacatta ccaattat                                                  18

<210> SEQ ID NO 391
<211> LENGTH: 6
<212> TYPE: PRT
<213> ORGANISM: Artificial Sequence
<220> FEATURE:
<223> OTHER INFORMATION: synthetic

<400> SEQUENCE: 391

Gln Asp Ile Thr Asn Tyr
 1               5

<210> SEQ ID NO 392
<211> LENGTH: 9
<212> TYPE: DNA
<213> ORGANISM: Artificial Sequence
<220> FEATURE:
<223> OTHER INFORMATION: synthetic

<400> SEQUENCE: 392 gctgcatcc                                                                9

<210> SEQ ID NO 393
<211> LENGTH: 3
<212> TYPE: PRT
<213> ORGANISM: Artificial Sequence
<220> FEATURE:
<223> OTHER INFORMATION: synthetic

<400> SEQUENCE: 393

Ala Ala Ser
 1

<210> SEQ ID NO 394
<211> LENGTH: 27
<212> TYPE: DNA
<213> ORGANISM: Artificial Sequence
<220> FEATURE:
<223> OTHER INFORMATION: synthetic

<400> SEQUENCE: 394
caacagtata atagttaccc tcccact                                            27

<210> SEQ ID NO 395
<211> LENGTH: 9
<212> TYPE: PRT
<213> ORGANISM: Artificial Sequence
<220> FEATURE:
<223> OTHER INFORMATION: synthetic

<400> SEQUENCE: 395

Gln Gln Tyr Asn Ser Tyr Pro Pro Thr
 1               5

<210> SEQ ID NO 396
<211> LENGTH: 369
<212> TYPE: DNA
<213> ORGANISM: Artificial Sequence
<220> FEATURE:
<223> OTHER INFORMATION: synthetic

<400> SEQUENCE: 396
gaggtgcagt tattggagtc tgggggggaac ttggtacagc cggggggggtc cctgagactc       60 tcctgtgcag cctctggatt cacctttagc agttatgcca tgacctgggt ccgccaggct      120
ccagggaagg ggctggagtg ggtctcaact attagtggta gtggtaccag cacatattac      180
gcagactccg tgaagggccg gttcaccatc tccagggaca attccaggga cacggtgttt      240
ctacaaatga acagcctgag agccgaggac acggccgtat attactgttc gaaaccttct      300
gcattacgat ttttacattg gttatgtatg gacgtctggg gccaagggac cctggtcacc      360
gtctcctca                                                                                369

<210> SEQ ID NO 397
<211> LENGTH: 123
<212> TYPE: PRT
<213> ORGANISM: Artificial Sequence
<220> FEATURE:
<223> OTHER INFORMATION: synthetic

<400> SEQUENCE: 397

Glu Val Gln Leu Leu Glu Ser Gly Gly Asn Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Thr Ile Ser Gly Ser Gly Thr Ser Thr Tyr Tyr Ala Asp Ser Val
    50                  55                  60

Lys Gly Arg Phe Thr Ile Ser Arg Asp Asn Ser Arg Asp Thr Val Phe
65                  70                  75                  80

Leu Gln Met Asn Ser Leu Arg Ala Glu Asp Thr Ala Val Tyr Tyr Cys
                85                  90                  95

Ser Lys Pro Ser Ala Leu Arg Phe Leu His Trp Leu Cys Met Asp Val
            100                 105                 110

Trp Gly Gln Gly Thr Leu Val Thr Val Ser Ser
        115                 120

<210> SEQ ID NO 398
<211> LENGTH: 24
<212> TYPE: DNA
<213> ORGANISM: Artificial Sequence
<220> FEATURE:
<223> OTHER INFORMATION: synthetic

<400> SEQUENCE: 398
ggattcacct ttagcagtta tgcc                                                               24

<210> SEQ ID NO 399
<211> LENGTH: 8
<212> TYPE: PRT
<213> ORGANISM: Artificial Sequence
<220> FEATURE:
<223> OTHER INFORMATION: synthetic

<400> SEQUENCE: 399

Gly Phe Thr Phe Ser Ser Tyr Ala
 1               5

<210> SEQ ID NO 400
<211> LENGTH: 24
<212> TYPE: DNA
<213> ORGANISM: Artificial Sequence
<220> FEATURE:
<223> OTHER INFORMATION: synthetic

<400> SEQUENCE: 400
attagtggta gtggtaccag caca                                                               24

<210> SEQ ID NO 401
<211> LENGTH: 8
<212> TYPE: PRT
<213> ORGANISM: Artificial Sequence
<220> FEATURE:
<223> OTHER INFORMATION: synthetic

<400> SEQUENCE: 401

Ile Ser Gly Ser Gly Thr Ser Thr
1               5

<210> SEQ ID NO 402
<211> LENGTH: 48
<212> TYPE: DNA
<213> ORGANISM: Artificial Sequence
<220> FEATURE:
<223> OTHER INFORMATION: synthetic

<400> SEQUENCE: 402
tcgaaacctt ctgcattacg atttttacat tggttatgta tggacgtc      48

<210> SEQ ID NO 403
<211> LENGTH: 16
<212> TYPE: PRT
<213> ORGANISM: Artificial Sequence
<220> FEATURE:
<223> OTHER INFORMATION: synthetic

<400> SEQUENCE: 403

Ser Lys Pro Ser Ala Leu Arg Phe Leu His Trp Leu Cys Met Asp Val
1               5                   10                  15

<210> SEQ ID NO 404
<211> LENGTH: 321
<212> TYPE: DNA
<213> ORGANISM: Artificial Sequence
<220> FEATURE:
<223> OTHER INFORMATION: synthetic

<400> SEQUENCE: 404
gacatccaga tgacccagtc tccatcctca ctgtctgcat ttgtaggaga cagagtcacc      60
atcacttgtc gggcgagtca ggacattagg aattatttag actggtttca gcagaaacca     120
gggaaagccc ctaagtccct gatctatgct gcatccaatt tgcaaagtgg ggtcccatca     180
aggttcggcg gcagtggatc tgggacagat ttcactctca ccatcaacag cctgcagcct     240
gaagattttg taacttatta ctgccagcag tataattctt accctcccac tttcggcgga     300
gggaccaagg tggagatcaa a                                               321

<210> SEQ ID NO 405
<211> LENGTH: 107
<212> TYPE: PRT
<213> ORGANISM: Artificial Sequence
<220> FEATURE:
<223> OTHER INFORMATION: synthetic

<400> SEQUENCE: 405

Asp Ile Gln Met Thr Gln Ser Pro Ser Ser Leu Ser Ala Phe Val Gly
1               5                   10                  15

Asp Arg Val Thr Ile Thr Cys Arg Ala Ser Gln Asp Ile Arg Asn Tyr
                20                  25                  30

Leu Asp Trp Phe Gln Gln Lys Pro Gly Lys Ala Pro Lys Ser Leu Ile
            35                  40                  45

Tyr Ala Ala Ser Asn Leu Gln Ser Gly Val Pro Ser Arg Phe Gly Gly
        50                  55                  60

Ser Gly Ser Gly Thr Asp Phe Thr Leu Thr Ile Asn Ser Leu Gln Pro
65                  70                  75                  80

```
Glu Asp Phe Val Thr Tyr Tyr Cys Gln Gln Tyr Asn Ser Tyr Pro Pro
            85                  90                  95
Thr Phe Gly Gly Gly Thr Lys Val Glu Ile Lys
            100                 105
```

<210> SEQ ID NO 406
<211> LENGTH: 18
<212> TYPE: DNA
<213> ORGANISM: Artificial Sequence
<220> FEATURE:
<223> OTHER INFORMATION: synthetic

<400> SEQUENCE: 406
caggacatta ggaattat                                              18

<210> SEQ ID NO 407
<211> LENGTH: 6
<212> TYPE: PRT
<213> ORGANISM: Artificial Sequence
<220> FEATURE:
<223> OTHER INFORMATION: synthetic

<400> SEQUENCE: 407

```
Gln Asp Ile Arg Asn Tyr
 1               5
```

<210> SEQ ID NO 408
<211> LENGTH: 9
<212> TYPE: DNA
<213> ORGANISM: Artificial Sequence
<220> FEATURE:
<223> OTHER INFORMATION: synthetic

<400> SEQUENCE: 408 gctgcatcc                                                         9

<210> SEQ ID NO 409
<211> LENGTH: 3
<212> TYPE: PRT
<213> ORGANISM: Artificial Sequence
<220> FEATURE:
<223> OTHER INFORMATION: synthetic

<400> SEQUENCE: 409

```
Ala Ala Ser
 1
```

<210> SEQ ID NO 410
<211> LENGTH: 27
<212> TYPE: DNA
<213> ORGANISM: Artificial Sequence
<220> FEATURE:
<223> OTHER INFORMATION: synthetic

<400> SEQUENCE: 410
cagcagtata attcttaccc tcccact                                    27

<210> SEQ ID NO 411
<211> LENGTH: 9
<212> TYPE: PRT
<213> ORGANISM: Artificial Sequence
<220> FEATURE:
<223> OTHER INFORMATION: synthetic

```
<400> SEQUENCE: 411

Gln Gln Tyr Asn Ser Tyr Pro Pro Thr
1               5
```

HUMAN ANTIBODIES TO GFR α3 AND METHODS OF TREATING PAIN ASSOCIATED WITH OSTEOARTHRITIS OR BONE CANCER

CROSS-REFERENCE TO RELATED APPLICATIONS

This application is a divisional of U.S. patent application Ser. No. 13/971,965, filed Aug. 21, 2013, entitled "HUMAN ANTIBODIES TO GFR ALPHA3 AND METHODS OF USE THEREOF," now U.S. Pat. No. 8,968,736, issued Mar. 3, 2015, which claims the benefit under 35 U.S.C. §119(e) of U.S. Provisional Application Ser. No. 61/692,029, filed Aug. 22, 2012, the disclosures of which are herein specifically incorporated by reference in their entirety.

FIELD OF THE INVENTION

The present invention is related to human antibodies and antigen-binding fragments of human antibodies that specifically bind to human glial cell-line derived neurotrophic factor (GDNF) family receptor alpha 3 (GFRα3), and therapeutic methods of using those antibodies.

STATEMENT OF RELATED ART

The glial cell line-derived neurotrophic factor related family is composed of glial cell line-derived neurotrophic factor (GDNF), neurturin (NRTN), artemin (ARTN) and persephin (PSPN). Each member of the GDNF family binds to a glycosylphosphatidylinositol (GPI)-anchored receptor associated with the plasma membrane. This family of receptors is referred to as the GDNF-family receptor alphas (GFRαs). This receptor family is composed of four different GFRα receptors, GFRα1-4. GDNF binds preferentially to GFRα1, NRTN binds preferentially to GFRα2, ARTN binds preferentially to GFRα3, and PSPN binds preferentially to GFRα4. Each GDNF family ligand signals through the RET ("rearranged during transfection") receptor tyrosine kinase, which was first discovered as a proto-oncogene. RET is activated by GDNF family members only if the ligand is first bound to its GFRα receptor (Airaksinen, M. S., et al. Nature Reviews Neuroscience (2002), 3:383-394).

Both ARTN and GFRα3 are highly expressed during development and are involved in sympathetic nervous system development. In adult, GFRα3 expression is largely restricted to the sensory neurons of the dorsal root ganglia (DRG) (Orozco, O. E., et al., European J. Neuroscience, (2001), 13:2177-2182). In adult mouse, artemin is expressed in testis, uterus, thyroid, prostate, and epididymis, as well as in olfactory bulbs and arterioles in the intestine and mesentery (Airaksinen, M. S., et al. Nature Reviews Neuroscience (2002), 3:383-394; Airaksinen, M. S. et al., Brain, Behavior and Evolution, (2006), 68:181-190).

A possible role for GFRα3 and artemin in hyperalgesia has been shown in several studies. For example, it has been demonstrated that an injection of the artemin protein into the hindpaw of a rodent caused thermal hyperalgesia and this nociception was enhanced when artemin was co-injected with NGF (Malin, S. A., et al., J. Neuroscience, (2006), 26(33): 8588-8599). Other studies showed that artemin mRNA expression was upregulated in a murine inflammatory model (Elitt, C. M., et al., J. Neuroscience, (2006), 26(33): 8578-8587). Furthermore, other studies showed that artemin transgenic mice have elevated expression of TRPV1 and TRPA1 and have increased behavioral sensitivity to heat and cold (Elitt, C. M., et al., J. Neuroscience, (2006), 26(33): 8578-8587). In addition, a possible role for GFRα3 in visceral hypersensitivity has been shown by studies in GFRα3 knockout mice, whereby these mice showed attenuation of visceral hypersensitivity after intracolonic treatment with TNBS (2,4,6-trinitrobenzene sulfonic acid) relative to wild type C57BL/6 mice (Tanaka, T., et al., Am. J. Physiol. Gastrointest. Liver Physiol. (2011), 300:G418-G424). A possible role for artemin and its receptor GFRα3 in pain associated with pancreatitis has also been shown by a study done in patients undergoing pancreatic head resection (Ceyhan, G. O., et al., Gut, (2007), 56:534-544). Based on the foregoing, further studies are warranted to determine whether patients suffering from pain/hyperalgesia and/or hypersensitivity could benefit by treatment with an inhibitor of GFRα3 activity.

Antibodies that bind GFRα3 are described in U.S. Pat. No. 6,861,509. In addition, U.S. Pat. No. 6,677,135 discloses a full length GFRα3 sequence, whereas splice variants of the GFRα3 molecule are described in U.S. Pat. No. 7,026,138; US2007/0232535 and US2006/0216289. U.S. Pat. No. 7,138,251 discloses sequences that have 99% identity to full length GFRα3 and the preparation of humanized monoclonal antibodies to this molecule is described in this patent.

BRIEF SUMMARY OF THE INVENTION

In a first aspect, the invention provides fully human monoclonal antibodies (mAbs) and antigen-binding fragments thereof that bind to human GFRα3 and inhibit or block its activity, for example, block the binding of GFRα3 to the glial cell line-derived neurotrophic factor, artemin, and possibly blocking the subsequent activation of the RET receptor tyrosine kinase and/or blocking signaling through RET and/or blocking signaling through a mediator other than RET. The antibodies or antigen binding fragments thereof may be useful for treating hyperalgesia, allodynia and/or hypersensitivity to any sensory stimulus, including, but not limited to pressure, heat and/or cold. The antibodies may also be used to treat pain/hypersensitivity associated with a wide range of conditions and disorders in which blocking the interaction of GFRα3 with artemin is desired. The antibodies may also be used to inhibit tumor cell growth, proliferation and/or metastasis.

In one embodiment, the invention provides an isolated antibody or an antigen-binding fragment thereof that specifically binds to human GFRα3 and has one or more of the following characteristics:

(i) exhibits a $K_D$ ranging from about $10^{-8}$M to about $10^{-13}$M as measured by surface plasmon resonance;

(ii) demonstrates the ability to block about 50-100% of the binding of GFRα3 to its ligand, artemin, with an $IC_{50}$ value ranging from about 40 pM to about 15 nM;

(iii) demonstrates the ability to block about 20% to about 100% of the binding of GFRα3 to a solid support coated with a mixture of artemin and RET;

(iv) blocks or inhibits artemin-dependent activation of RET with an $IC_{50}$ ranging from about 200 pM to about 50 nM;

(v) inhibits or reduces one or more nociceptive responses in an in vivo model of bone cancer pain;

(vi) inhibits or reduces artemin-sensitized thermal hyperalgesia in vivo;

(vii) inhibits or reduces allodynia in an in vivo model of osteoarthritis;

(viii) does not cross-react with other GFR co-receptors for RET;

(ix) comprises a heavy chain variable region (HCVR) having an amino acid sequence selected from the group consisting of SEQ ID NO: 2, 18, 34, 50, 66, 82, 98, 114, 130, 146, 162, 178, 194, 210, 226, 242, 258, 274, 290, 306, 322, 338, 354, 381 and 397; or (x) comprises a light chain variable region (LCVR) having an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 389 and 405.

In one embodiment, the isolated monoclonal antibody or an antigen-binding fragment thereof is selected from the group consisting of a murine, chimeric, humanized and a human antibody.

In one embodiment, the isolated monoclonal antibody or an antigen-binding fragment thereof does not cross-react with human GFRα1 or human GFRα2.

In one embodiment, the isolated monoclonal antibody or an antigen-binding fragment thereof comprises (a) a heavy chain variable region (HCVR) having an amino acid sequence selected from the group consisting of SEQ ID NO: 2, 18, 34, 50, 66, 82, 98, 114, 130, 146, 162, 178, 194, 210, 226, 242, 258, 274, 290, 306, 322, 338, 354, 381 and 397 and (b) a light chain variable region (LCVR) having an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 389 and 405.

In one embodiment, the isolated monoclonal antibody or an antigen-binding fragment thereof demonstrates the ability to block about 50-95% of the binding of human GFRα3 to its ligand, artemin, with an $IC_{50}$ value ranging from about 40 pM to about 750 pM.

In one embodiment, the isolated monoclonal antibody or an antigen-binding fragment thereof blocks about 75-100% of the binding of human GFRα3 to its ligand, artemin, with an $IC_{50}$ value ranging from about 400 pM to about 15 nM.

In one embodiment, the isolated monoclonal antibody or an antigen-binding fragment thereof blocks or inhibits artemin-dependent activation of human RET with an $IC_{50}$ ranging from about 300 pM to about 5 nM.

In one embodiment, the isolated monoclonal antibody or an antigen-binding fragment thereof blocks or inhibits artemin-dependent activation of cynomolgus RET with an $IC_{50}$ ranging from about 0.7 nM to about 2.5 nM.

In one embodiment, the isolated monoclonal antibody or an antigen-binding fragment thereof comprises the three heavy chain CDRs (HCDR1, HCDR2 and HCDR3) contained within a HCVR amino acid sequence selected from the group consisting of SEQ ID NO: 2, 18, 34, 50, 66, 82, 98, 114, 130, 146, 162, 178, 194, 210, 226, 242, 258, 274, 290, 306, 322, 338, 354, 381 and 397; and the three light chain CDRs (LCDR1, LCDR2 and LCDR3) contained within a LCVR amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 389 and 405.

In one embodiment, the isolated monoclonal antibody or an antigen-binding fragment thereof comprises a heavy chain variable region (HCVR) having an amino acid sequence selected from the group consisting of SEQ ID NO: 2, 18, 34, 50, 66, 82, 98, 114, 130, 146, 162, 178, 194, 210, 226, 242, 258, 274, 290, 306, 322, 338, 354, 381 and 397.

In one embodiment, the isolated monoclonal antibody or an antigen-binding fragment thereof comprises a light chain variable region (LCVR) having an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 389 and 405.

In one embodiment, the isolated monoclonal antibody or an antigen-binding fragment thereof comprises a HCVR/LCVR amino acid sequence pair selected from the group consisting of SEQ ID NOs: SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 381/389 and 397/405.

In one embodiment, the isolated monoclonal antibody or an antigen-binding fragment thereof comprises a HCVR/LCVR amino acid sequence pair selected from the group consisting of SEQ ID NO: 50/58, 146/154, 210/218 and 290/298.

In one embodiment, the isolated monoclonal antibody or an antigen-binding fragment thereof comprises:

(a) a HCDR1 domain having an amino acid sequence selected from the group consisting of SEQ ID NOs: 4, 20, 36, 52, 68, 84, 100, 116, 132, 148, 164, 180, 196, 212, 228, 244, 260, 276, 292, 308, 324, 340, 356, 383 and 399;

(b) a HCDR2 domain having an amino acid sequence selected from the group consisting of SEQ ID NOs: 6, 22, 38, 54, 70, 86, 102, 118, 134, 150, 166, 182, 198, 214, 230, 246, 262, 278, 294, 310, 326, 342, 358, 385 and 401;

(c) a HCDR3 domain having an amino acid sequence selected from the group consisting of SEQ ID NOs: 8, 24, 40, 56, 72, 88, 104, 120, 136, 152, 168, 184, 200, 216, 232, 248, 264, 280, 296, 312, 328, 344, 360, 387 and 403;

(d) a LCDR1 domain having an amino acid sequence selected from the group consisting of SEQ ID NOs: 12, 28, 44, 60, 76, 92, 108, 124, 140, 156, 172, 188, 204, 220, 236, 252, 268, 284, 300, 316, 332, 348, 364, 391 and 407;

(e) a LCDR2 domain having an amino acid sequence selected from the group consisting of SEQ ID NOs: 14, 30, 46, 62, 78, 94, 110, 126, 142, 158, 174, 190, 206, 222, 238, 254, 270, 286, 302, 318, 334, 350, 366, 393 and 409; and (f) a LCDR3 domain having an amino acid sequence selected from the group consisting of SEQ ID NOs: 16, 32, 48, 64, 80, 96, 112, 128, 144, 160, 176, 192, 208, 224, 240, 256, 272, 288, 304, 320, 336, 352, 368, 395 and 411.

In one embodiment, the isolated monoclonal antibody or an antigen-binding fragment thereof competes for specific binding to human GFRα3 with an antibody or antigen-binding fragment comprising heavy and light chain sequence pairs selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346 and 354/362, 381/389 and 397/405.

In one embodiment, the isolated monoclonal antibody or an antigen-binding fragment thereof binds the same epitope on human GFRα3 that is recognized by an antibody comprising heavy and light chain sequence pairs selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346 and 354/362, 381/389 and 397/405.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, J. Immunol. 164:1925-1933).

In one embodiment, the isolated antibody or antigen-binding fragment thereof that binds specifically to human GFRα3, comprises a HCVR comprising the three heavy chain CDRs (HCDR1, HCDR2 and HCDR3) contained within the HCVR amino acid sequences selected from the group consisting of SEQ ID NO: 2, 18, 34, 50, 66, 82, 98, 114, 130, 146, 162, 178, 194, 210, 226, 242, 258, 274, 290, 306, 322, 338, 354, 381 and 397; and/or a LCVR comprising the three light chain CDRs (LCDR1, LCDR2 and LCDR3) contained within the LCVR amino acid sequences selected from the group consisting of SEQ ID NOs: 10, 26, 42, 58, 74, 90, 106, 122, 138, 154, 170, 186, 202, 218, 234, 250, 266, 282, 298, 314, 330, 346, 362, 389 and 405. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In one embodiment, the isolated antibody or antigen-binding fragment that specifically binds human GFRα3 comprises:

(a) a HCDR3 domain having an amino acid sequence selected from the group consisting of SEQ ID NOs: 8, 24, 40, 56, 72, 88, 104, 120, 136, 152, 168, 184, 200, 216, 232, 248, 264, 280, 296, 312, 328, 344, 360, 387 and 403; and (b) a LCDR3 domain having an amino acid sequence selected from the group consisting of SEQ ID NOs: 16, 32, 48, 64, 80, 96, 112, 128, 144, 160, 176, 192, 208, 224, 240, 256, 272, 288, 304, 320, 336, 352, 368, 395 and 411.

In one embodiment, the isolated antibody or antigen-binding fragment that specifically binds human GFRα3, as described in (a) and (b) above, further comprises:

(c) a HCDR1 domain having an amino acid sequence selected from the group consisting of SEQ ID NOs: 4, 20, 36, 52, 68, 84, 100, 116, 132, 148, 164, 180, 196, 212, 228, 244, 260, 276, 292, 308, 324, 340, 356, 383 and 399;

(d) a HCDR2 domain having an amino acid sequence selected from the group consisting of SEQ ID NOs: 6, 22, 38, 54, 70, 86, 102, 118, 134, 150, 166, 182, 198, 214, 230, 246, 262, 278, 294, 310, 326, 342, 358, 385 and 401;

(e) a LCDR1 domain having an amino acid sequence selected from the group consisting of SEQ ID NOs: 12, 28, 44, 60, 76, 92, 108, 124, 140, 156, 172, 188, 204, 220, 236, 252, 268, 284, 300, 316, 332, 348, 364, 391 and 407; and (f) a LCDR2 domain having an amino acid sequence selected from the group consisting of SEQ ID NOs: 14, 30, 46, 62, 78, 94, 110, 126, 142, 158, 174, 190, 206, 222, 238, 254, 270, 286, 302, 318, 334, 350, 366, 393 and 409.

In one embodiment, the invention provides a fully human monoclonal antibody or antigen-binding fragment thereof that binds specifically to human GFRα3, wherein the antibody or fragment thereof exhibits one or more of the following characteristics: (i) comprises a HCVR having an amino acid sequence selected from the group consisting of SEQ ID NOs: 2, 18, 34, 50, 66, 82, 98, 114, 130, 146, 162, 178, 194, 210, 226, 242, 258, 274, 290, 306, 322, 338, 354, 381 and 397; (ii) comprises a LCVR having an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 389 and 405; (iii) comprises a HCDR3 domain having an amino acid sequence selected from the group consisting of SEQ ID NOs: 8, 24, 40, 56, 72, 88, 104, 120, 136, 152, 168, 184, 200, 216, 232, 248, 264, 280, 296, 312, 328, 344, 360, 387 and 403, or a substantially similar sequence thereof having at least 90%, at least 95%, at least 98% or at least 99% sequence identity; and a LCDR3 domain having an amino acid sequence selected from the group consisting of SEQ ID NOs: 16, 32, 48, 64, 80, 96, 112, 128, 144, 160, 176, 192, 208, 224, 240, 256, 272, 288, 304, 320, 336, 352, 368, 395 and 411 or a substantially similar sequence thereof having at least 90%, at least 95%, at least 98% or at least 99% sequence identity; (iv) comprises a HCDR1 domain having an amino acid sequence selected from the group consisting of SEQ ID NOs: 4, 20, 36, 52, 68, 84, 100, 116, 132, 148, 164, 180, 196, 212, 228, 244, 260, 276, 292, 308, 324, 340, 356, 383 and 399 or a substantially similar sequence thereof having at least 90%, at least 95%, at least 98% or at least 99% sequence identity; a HCDR2 domain having an amino acid sequence selected from the group consisting of SEQ ID NOs: 6, 22, 38, 54, 70, 86, 102, 118, 134, 150, 166, 182, 198, 214, 230, 246, 262, 278, 294, 310, 326, 342, 358, 385 and 401 or a substantially similar sequence thereof having at least 90%, at least 95%, at least 98% or at least 99% sequence identity; a LCDR1 domain having an amino acid sequence selected from the group consisting of SEQ ID NOs: 12, 28, 44, 60, 76, 92, 108, 124, 140, 156, 172, 188, 204, 220, 236, 252, 268, 284, 300, 316, 332, 348, 364, 391 and 407 or a substantially similar sequence thereof having at least 90%, at least 95%, at least 98% or at least 99% sequence identity; and a LCDR2 domain having an amino acid sequence selected from the group consisting of SEQ ID NOs: 14, 30, 46, 62, 78, 94, 110, 126, 142, 158, 174, 190, 206, 222, 238, 254, 270, 286, 302, 318, 334, 350, 366, 393 and 409 or a substantially similar sequence thereof having at least 90%, at least 95%, at least 98% or at least 99% sequence identity; (v) exhibits a $K_D$ ranging from about $10^{-8}$M to about $10^{-13}$M as measured by surface plasmon resonance; (vi) demonstrates the ability to block about 50-100% of the binding of GFRα3 to its ligand, artemin, with an $IC_{50}$ value ranging from about 40 pM to about 15 nM; (vii) demonstrates the ability to block about 20% to about 100% of the binding of GFRα3 to a solid support coated with a mixture of artemin and RET; (viii) blocks or inhibits artemin-dependent activation of RET with an $IC_{50}$ ranging from about 200 pM to about 50 nM; (ix) inhibits or reduces one or more nociceptive responses in an in vivo model of bone cancer pain; (x) inhibits or reduces artemin-sensitized thermal hyperalgesia in vivo; (xi) inhibits or reduces allodynia in an in vivo model of osteoarthritis; (xii) does not cross-react with other GFR co-receptors for RET.

In one embodiment, the present invention provides an antibody or antigen-binding fragment of an antibody comprising a HCDR3 domain having an amino acid sequence selected from any of those shown in Table 1, or a substantially similar sequence thereof having at least 90%, at least 95%, at least 98% or at least 99% sequence identity; and a LCDR3 domain having an amino acid sequence selected from any of those shown in Table 1, or a substantially similar sequence thereof having at least 90%, at least 95%, at least 98% or at least 99% sequence identity.

In one embodiment, the invention provides an antibody or fragment thereof further comprising a HCDR1 domain having an amino acid sequence of any of those shown in Table 1, or a substantially similar sequence thereof having at least 90%, at least 95%, at least 98% or at least 99% sequence identity; a HCDR2 domain having an amino acid sequence of any of those shown on Table 1, or a substantially similar sequence thereof having at least 90%, at least 95%, at least 98% or at least 99% sequence identity; a LCDR1 domain having an amino acid sequence of any of those shown in Table 1, or a substantially similar sequence thereof having at least 90%, at least 95%, at least 98% or at least 99% sequence identity; and a LCDR2 domain having an amino acid sequence of any of those shown in Table 1, or a substantially similar sequence thereof having at least 90%, at least 95%, at least 98% or at least 99% sequence identity.

In certain embodiments, the antibody or antigen-binding portion of an antibody that specifically binds to human GFRα3 comprises a HCDR3/LCDR3 amino acid sequence pair selected from any of the HCDR3/LCDR3 amino acid sequences shown in Table 1. According to certain embodiments, the antibody or antigen-binding portion of an antibody comprises a HCDR3/LCDR3 amino acid sequence pair selected from the group consisting of SEQ ID NOs: 8/16, 24/32, 40/48, 56/64, 72/80, 88/96, 104/112, 120/128, 136/144, 152/160, 168/176, 184/192, 200/208, 216/224, 232/240, 248/256, 264/272, 280/288, 296/304, 312/320, 328/336, 344/352, 360/368, 387/395 and 403/411.

In one embodiment, the antibody or antigen binding fragment thereof comprises the HCDR1, HCDR2 and HCDR3 sequences of SEQ ID NOs: 4, 6 and 8, respectively and LCDR1, LCDR2 and LCDR3 sequences of SEQ ID NOs: 12, 14 and 16, respectively.

In one embodiment, the antibody or antigen binding fragment thereof comprises the HCDR1, HCDR2 and HCDR3 sequences of SEQ ID NOs: 20, 22 and 24, respectively and LCDR1, LCDR2 and LCDR3 sequences of SEQ ID NOs: 28, 30 and 32, respectively.

In one embodiment, the antibody or antigen binding fragment thereof comprises the HCDR1, HCDR2 and HCDR3 sequences of SEQ ID NOs: 36, 38 and 40, respectively and LCDR1, LCDR2 and LCDR3 sequences of SEQ ID NOs: 44, 46 and 48, respectively.

In one embodiment, the antibody or antigen binding fragment thereof comprises the HCDR1, HCDR2 and HCDR3 sequences of SEQ ID NOs: 52, 54 and 56, respectively and LCDR1, LCDR2 and LCDR3 sequences of SEQ ID NOs: 60, 62 and 64, respectively.

In one embodiment, the antibody or antigen binding fragment thereof comprises the HCDR1, HCDR2 and HCDR3 sequences of SEQ ID NOs: 68, 70 and 72, respectively and LCDR1, LCDR2 and LCDR3 sequences of SEQ ID NOs: 76, 78 and 80, respectively.

In one embodiment, the antibody or antigen binding fragment thereof comprises the HCDR1, HCDR2 and HCDR3 sequences of SEQ ID NOs: 84, 86 and 88, respectively and LCDR1, LCDR2 and LCDR3 sequences of SEQ ID NOs: 92, 94 and 96, respectively.

In one embodiment, the antibody or antigen binding fragment thereof comprises the HCDR1, HCDR2 and HCDR3 sequences of SEQ ID NOs: 100, 102 and 104, respectively and LCDR1, LCDR2 and LCDR3 sequences of SEQ ID NOs: 108, 110 and 112, respectively.

In one embodiment, the antibody or antigen binding fragment thereof comprises the HCDR1, HCDR2 and HCDR3 sequences of SEQ ID NOs: 116, 118 and 120, respectively and LCDR1, LCDR2 and LCDR3 sequences of SEQ ID NOs: 124, 126 and 128, respectively.

In one embodiment, the antibody or antigen binding fragment thereof comprises the HCDR1, HCDR2 and HCDR3 sequences of SEQ ID NOs: 132, 134 and 136, respectively and LCDR1, LCDR2 and LCDR3 sequences of SEQ ID NOs: 140, 142 and 144, respectively.

In one embodiment, the antibody or antigen binding fragment thereof comprises the HCDR1, HCDR2 and HCDR3 sequences of SEQ ID NOs: 148, 150 and 152, respectively and LCDR1, LCDR2 and LCDR3 sequences of SEQ ID NOs: 156, 158 and 160, respectively.

In one embodiment, the antibody or antigen binding fragment thereof comprises the HCDR1, HCDR2 and HCDR3 sequences of SEQ ID NOs: 164, 166 and 168, respectively and LCDR1, LCDR2 and LCDR3 sequences of SEQ ID NOs: 172, 174 and 176, respectively.

In one embodiment, the antibody or antigen binding fragment thereof comprises the HCDR1, HCDR2 and HCDR3 sequences of SEQ ID NOs: 180, 182 and 184, respectively and LCDR1, LCDR2 and LCDR3 sequences of SEQ ID NOs: 188, 190 and 192, respectively.

In one embodiment, the antibody or antigen binding fragment thereof comprises the HCDR1, HCDR2 and HCDR3 sequences of SEQ ID NOs: 196, 198 and 200, respectively and LCDR1, LCDR2 and LCDR3 sequences of SEQ ID NOs: 204, 206 and 208, respectively.

In one embodiment, the antibody or antigen binding fragment thereof comprises the HCDR1, HCDR2 and HCDR3 sequences of SEQ ID NOs: 212, 214 and 216, respectively and LCDR1, LCDR2 and LCDR3 sequences of SEQ ID NOs: 220, 222 and 224, respectively.

In one embodiment, the antibody or antigen binding fragment thereof comprises the HCDR1, HCDR2 and HCDR3 sequences of SEQ ID NOs: 228, 230 and 232, respectively and LCDR1, LCDR2 and LCDR3 sequences of SEQ ID NOs: 236, 238 and 240, respectively.

In one embodiment, the antibody or antigen binding fragment thereof comprises the HCDR1, HCDR2 and HCDR3 sequences of SEQ ID NOs: 244, 246 and 248, respectively and LCDR1, LCDR2 and LCDR3 sequences of SEQ ID NOs: 252, 254 and 256, respectively.

In one embodiment, the antibody or antigen binding fragment thereof comprises the HCDR1, HCDR2 and HCDR3 sequences of SEQ ID NOs: 260, 262 and 264, respectively and LCDR1, LCDR2 and LCDR3 sequences of SEQ ID NOs: 268, 270 and 272, respectively.

In one embodiment, the antibody or antigen binding fragment thereof comprises the HCDR1, HCDR2 and HCDR3 sequences of SEQ ID NOs: 276, 278 and 280, respectively and LCDR1, LCDR2 and LCDR3 sequences of SEQ ID NOs: 284, 286 and 288, respectively.

In one embodiment, the antibody or antigen binding fragment thereof comprises the HCDR1, HCDR2 and HCDR3 sequences of SEQ ID NOs: 292, 294 and 296, respectively and LCDR1, LCDR2 and LCDR3 sequences of SEQ ID NOs: 300, 302 and 304, respectively.

In one embodiment, the antibody or antigen binding fragment thereof comprises the HCDR1, HCDR2 and HCDR3 sequences of SEQ ID NOs: 308, 310 and 312, respectively and LCDR1, LCDR2 and LCDR3 sequences of SEQ ID NOs: 316, 318 and 320, respectively.

In one embodiment, the antibody or antigen binding fragment thereof comprises the HCDR1, HCDR2 and HCDR3 sequences of SEQ ID NOs: 324, 326 and 328, respectively and LCDR1, LCDR2 and LCDR3 sequences of SEQ ID NOs: 332, 334 and 336, respectively.

In one embodiment, the antibody or antigen binding fragment thereof comprises the HCDR1, HCDR2 and HCDR3 sequences of SEQ ID NOs: 340, 342 and 344, respectively and LCDR1, LCDR2 and LCDR3 sequences of SEQ ID NOs: 348, 350 and 352, respectively.

In one embodiment, the antibody or antigen binding fragment thereof comprises the HCDR1, HCDR2 and HCDR3 sequences of SEQ ID NOs: 356, 358 and 360, respectively and LCDR1, LCDR2 and LCDR3 sequences of SEQ ID NOs: 364, 366 and 368, respectively.

In one embodiment, the antibody or antigen binding fragment thereof comprises the HCDR1, HCDR2 and HCDR3 sequences of SEQ ID NOs: 383, 385 and 387, respectively and LCDR1, LCDR2 and LCDR3 sequences of SEQ ID NOs: 391, 393 and 395, respectively.

In one embodiment, the antibody or antigen binding fragment thereof comprises the HCDR1, HCDR2 and HCDR3 sequences of SEQ ID NOs: 399, 401 and 403, respectively and LCDR1, LCDR2 and LCDR3 sequences of SEQ ID NOs: 407, 409 and 411, respectively.

Certain non-limiting, exemplary antibodies and antigen-binding fragments of the invention comprise HCDR1, HCDR2, HCDR3, LCDR1, LCDR2 and LCDR3 domains, respectively, selected from any of the amino acid sequences shown in Table 1.

In a second aspect, the invention provides nucleic acid molecules encoding anti-GFRα3 antibodies or fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NOs: 1, 17, 33, 49, 65, 81, 97, 113, 129, 145, 161, 177, 193, 209, 225, 241, 257, 273, 289, 305, 321, 337, 353, 380 and 396 or a substantially identical sequence having at least 90%, at least 95%, at least 98%, or at least 99% homology thereof. In one embodiment, the HCVR is encoded by a nucleic acid sequence selected from the group consisting of SEQ ID NOs: 49, 145, 209 and 289.

In one embodiment, the antibody or fragment thereof further comprises a LCVR encoded by a nucleic acid sequence selected from the group consisting of SEQ ID NOs: 9, 25, 41, 57, 73, 89, 105, 121, 137, 153, 169, 185, 201, 217, 233, 249, 265, 281, 297, 313, 329, 345, 361, 388 and 404 or a substantially identical sequence having at least 90%, at least 95%, at least 98%, or at least 99% homology thereof. In one embodiment, the LCVR is encoded by a nucleic acid sequence selected from the group consisting of SEQ ID NOs: 57, 153, 217 and 297.

In one embodiment, the invention also provides an antibody or antigen-binding fragment of an antibody comprising a HCDR3 domain encoded by a nucleotide sequence located within the variable regions from any of the antibodies shown in Table 1, or a substantially similar sequence thereof having at least 90%, at least 95%, at least 98% or at least 99% sequence identity; and a LCDR3 domain encoded by a nucleotide sequence selected from any of those shown in Table 1, or a substantially similar sequence thereof having at least 90%, at least 95%, at least 98% or at least 99% sequence identity.

In one embodiment, the invention provides an antibody or fragment thereof further comprising a HCDR1 domain encoded by a nucleotide sequence of any of those shown in Table 1, or a substantially similar sequence thereof having at least 90%, at least 95%, at least 98% or at least 99% sequence identity; a HCDR2 domain encoded by a nucleotide sequence of any of those shown in Table 1, or a substantially similar sequence thereof having at least 90%, at least 95%, at least 98% or at least 99% sequence identity; a LCDR1 domain encoded by a nucleotide sequence of any of those shown in Table 1, or a substantially similar sequence thereof having at least 90%, at least 95%, at least 98% or at least 99% sequence identity; and a LCDR2 domain encoded by a nucleotide sequence shown in Table 1, or a substantially similar sequence thereof having at least 90%, at least 95%, at least 98% or at least 99% sequence identity.

In a third aspect, the invention features a human anti-hGFRα3 antibody or antigen-binding fragment of an antibody comprising a HCVR encoded by nucleotide sequence segments derived from $V_H$, $D_H$ and $J_H$ germline sequences, and a LCVR encoded by nucleotide sequence segments derived from $V_K$ and $J_K$ germline sequences, with combinations as shown in Table 2.

The invention encompasses anti-hGFRα3 antibodies having a modified glycosylation pattern. In some applications, modification to remove undesirable glycosylation sites may be useful, or e.g., removal of a fucose moiety to increase antibody dependent cellular cytotoxicity (ADCC) function (see Shield et al. (2002) JBC 277:26733). In other applications, modification of galactosylation can be made in order to modify complement dependent cytotoxicity (CDC).

In a fourth aspect, the invention features a pharmaceutical composition comprising a recombinant human antibody or fragment thereof, which specifically binds hGFRα3 and a pharmaceutically acceptable carrier. In one embodiment, the invention features a composition, which is a combination of an antibody or antigen-binding fragment of an antibody of the invention, and a second therapeutic agent. The second therapeutic agent may be any agent that is advantageously combined with the antibody or fragment thereof of the invention, for example, an agent capable of reducing pain, such as, but not limited to, opioids, morphine, a COX-2 inhibitor, aspirin, or other non-steroidal anti-inflammatories, acetaminophen, duloxetine, local anesthetics, NMDA modulators, cannabinoid receptor agonists, P2X family modulators, VR1 antagonists, and substance P antagonists. The second therapeutic agent may be an interleukin-1 (IL-1) inhibitor, for example, a fusion protein (U.S. Pat. No. 6,927,044); or an antiepileptic/anticonvulsant drug, such as gabapentin, pregabalin, topiramate; or a tricyclic antidepressant, such as amitriptyline; a cytokine inhibitor or antagonist, such as an antagonist to IL-6, IL-6R, IL-18 or IL-18R, or an inhibitor of a voltage-gated sodium channel, such as a $Na_v1.7$ inhibitor, or a $Na_v1.8$ inhibitor, or a $Na_v1.9$ inhibitor; an inhibitor of a potassium channel or calcium channel; or a NGF inhibitor (a small molecule inhibitor or an anti-NGF antibody), or a second inhibitor or antagonist to GFRα3, a tumor necrosis factor (TNF) or TNF receptor inhibitor, an inhibitor of TWEAK (TNF-related WEAK inducer of apoptosis), a RET inhibitor, an inhibitor of a GDNF family ligand, an inhibitor of GFRα1, GFRα2 or GFRα4, an inhibitor of an acid sensing ion channel (e.g. ASIC1 or ASIC3), or a selective serotonin reuptake inhibitor (SSRI), or a serotonin norepinephrine reuptake inhibitor (SNRI), or an inhibitor of a prekineticin receptor (e.g. PROK1 and PROK2), or a caspase inhibitor, a p38 inhibitor, an IKK1/2 inhibitor, CTLA-4Ig, or a corticosteroid. The second therapeutic agent may be a small molecule drug or a protein/ polypeptide inhibitor. The second therapeutic agent may be synthetic or naturally derived. The second therapeutic agent may be a second antibody specific for GFRα3, a polypeptide antagonist, a siRNA or an antisense molecule specific for GFRα3. It will also be appreciated that the antibodies and pharmaceutically acceptable compositions of the present invention can be employed in combination therapies, that is, the antibodies and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an antibody may be administered concurrently with another agent used to treat the same disorder), or they may achieve different effects (e.g., control of any adverse effects). As used herein, additional therapeutic agents that are normally administered to treat or prevent a particular disease, or condition, are appropriate for the disease, or condition, being treated.

In a fifth aspect, the invention features methods for inhibiting hGFRα3 activity using an anti-hGFRα3 antibody or antigen-binding portion of an antibody of the invention, wherein the methods comprise administering a therapeutically effective amount of one or more antibodies of the invention, or antigen binding fragments thereof, or a pharmaceutical composition comprising one or more antibodies of the invention or antigen-binding fragments thereof.

In a sixth aspect, the invention features a method for treating a GFRα3-related condition or disease, or the pain associated with a GFRα3-related condition or disease, the method comprising administering an anti-GFRα3 antibody or antigen-binding portion of an antibody of the invention, or a composition comprising an anti-GFRα3 antibody or a fragment thereof, to a patient in need thereof, wherein the GFRα3-related condition or disease is prevented, ameliorated, or reduced in severity or frequency of occurrence, or the pain associated with the condition or disease is prevented, ameliorated, or reduced in severity or occurrence.

In one embodiment, the GFRα3-related condition or disease is selected from the group consisting of acute pain, chronic pain, neuropathic pain, inflammatory pain, a functional pain syndrome, arthritis, pancreatitis, osteoarthritis, cluster headaches, trigeminal neuralgia, herpetic neuralgia, general neuralgias, neurodegenerative disorders, movement disorders, neuroendocrine disorders, ataxia, visceral pain, acute gout, post-herpetic neuralgia, diabetic neuropathy, sciatica, back pain, head or neck pain, severe or intractable pain, breakthrough pain, post-surgical pain, hereditary erythromelalgia, dental pain, rhinitis, cancer pain, complex regional pain syndrome (CRPS), inflammatory bowel disease (e.g. Crohn's disease or ulcerative colitis) and bladder disorders.

In one embodiment, the functional pain syndrome is selected from the group consisting of chronic low back pain, irritable bowel syndrome (IBS), fibromyalgia (FM), chronic fatigue syndrome, abdominal pain, temporomandibular joint disorder (TMJD), painful bladder syndrome (interstitial cystitis), functional gastrointestinal disorders/syndromes, functional chest pain syndrome, migraines and tension type headaches, chronic pelvic pain syndrome, painful prostate syndrome (chronic prostatitis), multiple chemical sensitivity syndrome and Gulf War syndrome.

In one embodiment, the cancer pain is associated with a cancer selected from the group consisting of endometrial cancer, prostate cancer, breast cancer, cervical cancer, liver cancer, pancreatic cancer, colon cancer, stomach cancer, uterine cancer, ovarian cancer, kidney cancer, non-small cell lung cancer, brain cancer, a leukemia, a lymphoma, bone cancer and pain associated with metastasis of a cancer.

In one embodiment, the antibody or antigen-binding fragment is administered to the patient in combination with a second therapeutic agent.

In one embodiment, the second therapeutic agent is selected from the group consisting of an opioid, a COX-2 inhibitor, a local anesthetic, an NMDA modulator, a cannabinoid receptor agonist, a P2X family modulator, a VR1 antagonist, a substance P antagonist, a second GFRα3 antagonist, a cytokine or cytokine receptor antagonist, a nerve growth factor (NGF) inhibitor (a small molecular inhibitor or an anti-NGF antibody), aspirin, a NSAID, a steroid, morphine, a selective serotonin reuptake inhibitor (SSRI), a serotonin norepinephrine reuptake inhibitor (SNRI), a tricyclic, an inhibitor of a voltage-gated sodium channel ($Na_v$), a calcium channel inhibitor, a potassium channel inhibitor, a tumor necrosis factor (TNF) or TNF receptor inhibitor, an inhibitor of TWEAK (TNF-related WEAK inducer of apoptosis), a RET inhibitor, an inhibitor of a GDNF family ligand, an inhibitor of an acid sensing ion channel (ASIC1 or ASIC3), an anti-convulsant (gabapentin or pregabalin), an inhibitor of a prekineticin receptor (PROK1 and PROK2), a caspase inhibitor, a p38 inhibitor, an IKK1/2 inhibitor, CTLA-4Ig and a corticosteroid.

In one embodiment, the second GFRα3 antagonist is a small organic molecule, a second antibody specific for GFRα3, a polypeptide antagonist, a siRNA or an antisense molecule specific for GFRα3.

In one embodiment, the cytokine or cytokine receptor antagonist is an interleukin-1 (IL-1) antagonist, an IL-6 antagonist, or an IL-18 antagonist.

The disorder treated is any disease or condition, which is improved, ameliorated, inhibited or prevented by removal, inhibition or reduction of hGFRα3 activity. Specific populations treatable by the therapeutic methods of the invention include a disease, disorder, or condition selected from acute, chronic, ischemic, neuropathic, or inflammatory pain, hypersensitivity, such as visceral, thermal, or mechanical hypersensitivity, chronic pancreatitis, arthritis, migraine, cluster headaches, trigeminal neuralgia, herpetic neuralgia, general neuralgias, epilepsy or epileptic conditions, myotonia, arrhythmia, movement disorders, neuroendocrine disorders, ataxia, inflammatory bowel disease, spleen inflammation, stomach pain, trigonitis, fibroids, peritonitis, faecal urgency, incontinence, rectal hypersensitivity, visceral pain, osteoarthritis pain, post-herpetic neuralgia, diabetic neuropathy, radicular pain, sciatica, back pain, head or neck pain, breakthrough pain, post-surgical pain, cancer pain, or chemotherapy-induced pain. Other conditions treatable by the therapeutic methods of the invention include Hirschsprung disease, hereditary erythromelalgia, bladder disorders, rhinitis, prostate cancer, breast cancer, cervical cancer, liver cancer, pancreatic cancer, colon cancer, stomach cancer, uterine cancer, ovarian cancer, kidney cancer, a hematologic (blood-borne) cancer, such as a leukemia or a lymphoma, bone cancer, or pain associated with metastasis of a cancer, for example, pain associated with metastasis of a cancer to the bone. The antibodies of the invention or antigen-binding fragments thereof may also be used to treat the following conditions: non-malignant acute, chronic, or fracture bone pain; rheumatoid arthritis, spinal stenosis; neuropathic low back pain; myofascial pain syndrome; pancreatic; chronic headache pain; tension headache; diabetic neuropathy; HIV-associated neuropathy; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome (CRPS, also known as Reflex Sympathetic Dystrophy); phantom pain; intractable pain; acute musculoskeletal pain; joint pain; acute gout pain; mechanical low back pain; neck pain; tendonitis; injury/exercise pain; abdominal pain; pyelonephritis; appendicitis; cholecystitis; intestinal obstruction; hernias; etc; chest pain, including, cardiac pain; pelvic pain, renal colic pain, acute obstetric pain, including, labor pain; cesarean section pain; burn and trauma pain; endometriosis; herpes zoster pain; sickle cell anemia; acute pancreatitis; breakthrough pain; orofacial pain including sinusitis pain, dental pain; multiple sclerosis pain; leprosy pain; Behcet's disease pain; adiposis dolorosa; phlebitic pain; Guillain-Barre pain; painful legs and moving toes; Haglund syndrome; Fabry's disease pain; bladder and urogenital disease; and hyperactivity bladder. In one embodiment the antibodies of the invention may be used to treat a functional pain syndrome, wherein the functional pain syndrome is selected from the group consisting of chronic low back pain, irritable bowel syndrome (IBS), fibromyalgia (FM), chronic fatigue syndrome, abdominal pain, temporomandibular joint disorder (TMJD), painful bladder syndrome (interstitial cystitis), functional gastrointestinal disorders/syndromes, functional chest pain syndrome, migraines and tension type headaches, chronic pelvic pain syndrome, painful prostate syndrome (chronic prostatitis), multiple chemical sensitivity syndrome and Gulf War syndrome.

The antibodies of the invention or antigen-binding fragments thereof may also be used to inhibit tumor cell growth/proliferation, or metastasis of tumor cells. In certain embodiments, the antibodies of the invention or antigen-binding fragments thereof, may be used to treat a cancer, or the "pain associated with a cancer" or "cancer-associated pain", including, for example, but not limited to, endometrial cancer, prostate cancer, breast cancer, cervical cancer, liver cancer, pancreatic cancer, colon cancer, stomach cancer, uterine cancer, ovarian cancer, kidney cancer, small cell lung cancer, non-small cell lung cancer, brain cancer, a hematologic (blood-borne) cancer, such as a leukemia or a lymphoma, bone cancer, or pain associated with metastasis of a cancer, for example, pain associated with metastasis of a cancer to the bone. "Cancer-associated pain" also includes pain more generally associated with cancerous conditions such as, e.g., renal cell carcinoma, pancreatic carcinoma, head and neck cancer, malignant gliomas, osteosarcoma, colorectal cancer, gastric cancer, malignant mesothelioma, multiple myeloma, synovial sarcoma, thyroid cancer, or melanoma. The antibodies of the present invention are also useful for treating or preventing pain caused by or associated with cancer therapy or anti-cancer medical treatments, e.g., chemotherapy-induced neuropathic pain such as pain caused by or associated with treatment with paclitaxel (TAXOL™), docetaxel (TAXOTERE®); nitrosourea, cyclophosphamide, doxorubicin, epirubicin, 5-fluorouracil, topotecan, irinotecan, carmustine, estramustine, and platinum-based chemotherapeutic compounds, such as cisplatin, carboplatin, and iproplatin.

Other embodiments will become apparent from a review of the ensuing detailed description.

BRIEF DESCRIPTION OF THE FIGURES

FIG. 9. Cross-Competition Analysis of anti-GFRα3 Antibodies for Binding to Biotin-hGFRα3-mmH.

DETAILED DESCRIPTION

Figure 1:
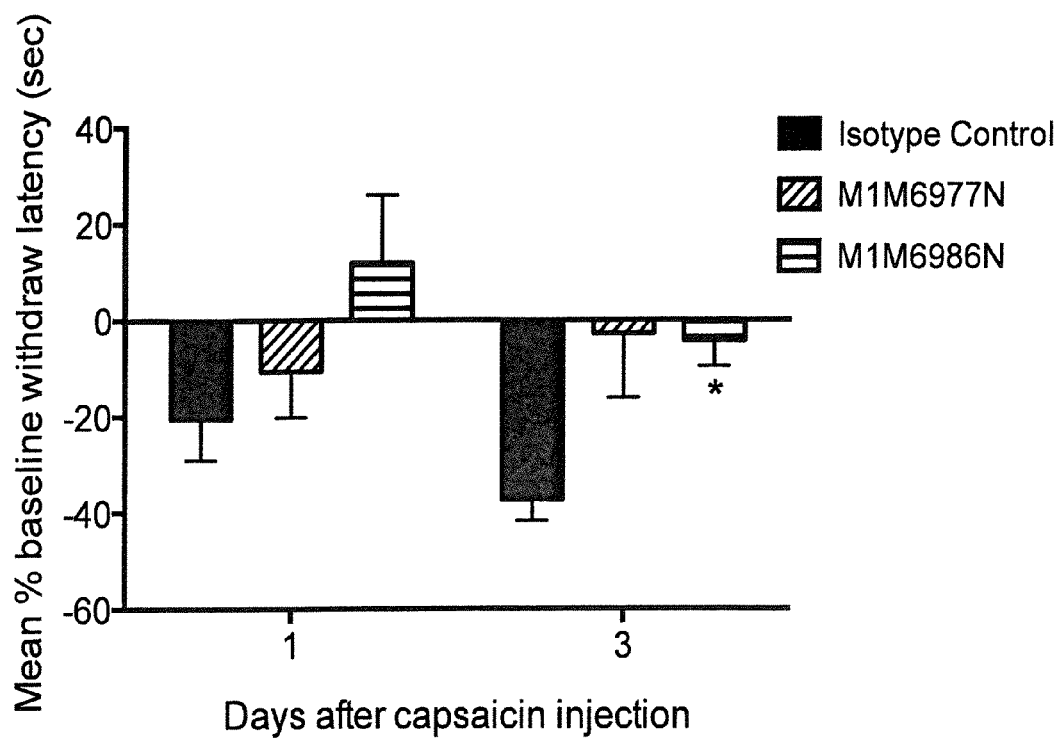
FIG. 1. Inhibition of artemin-sensitized capsaicin thermal hyperalgesia in animals injected with mouse GFRα3 antibodies (indirect blocker M1M6977N or direct blocker M1M6986N, n=8 each) or isotype (negative) control antibody (M2M180N, n=8) at 30 mg/kg s.c. 2 days before receiving capsaicin (1 day before receiving 0.5 μg artemin).

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

DEFINITIONS

"GFRα3," or "hGFRα3", as used herein, refers to the glycosylphosphatidylinositol (GPI)-anchored protein receptor for artemin, which belongs to the family of glial cell line derived neurotrophic factors (GDNF). It is one of the GDNF family receptor alpha proteins that, once bound to its ligand, artemin, mediates activation of the receptor tyrosine kinase RET ("rearranged during transfection"). Four members of the GFRα family have been recognized to date, GFRα-1-4 (Lindsay R M et al., Neuron, (1996), 17:571-574; Airaksinen, M S, et al., Mol. Cell Neurosci., (1999), 13:313-325). GFRα3 is also known in the art as GDNF family receptor alpha 3 GPI-linked receptor, or glial cell line-derived neurotrophic factor receptor alpha-3. The expression "GFRα3," or "hGFRα3", or fragments thereof, as used herein, refers to the human GFRα3 protein or fragment thereof, unless specified as being from a non-human species, e.g. "mouse GFRα3", "rat GFRα3", or "monkey GFRα3". Moreover, "GFRα3," or "hGFRα3", as used herein, refers to human GFRα3 encoded by the nucleic acid sequence shown in SEQ ID NO: 374 (Genbank accession number NM_001496) and has the amino acid sequence as shown in SEQ ID NO: 375 (Genbank accession number NP_001487.2), or a biologically active fragment thereof. The signal sequence spans amino acid residues 1-31 of SEQ ID NO: 375, the mature protein spans amino acid residues 32-382 of SEQ ID NO: 375, whereas the C-terminal Pro region spans amino acid residues 383-400 of SEQ ID NO: 375. The GPI cleavage site is found at amino acid residue 374 of SEQ ID NO: 375 (asparagine). The amino acid sequence of human artemin is found in Genbank as accession number Q5T4W7 and the amino acid sequence of human artemin (from amino acids A108-G220 of accession number Q5T4W7) with a myc-myc-hexahistidine tag is shown as SEQ ID NO: 369 (with amino acid residues 114-141 of SEQ ID NO: 369 being the myc-myc hexahistidine tag).

Although GFRα3 is structurally and functionally similar to the other members of the GFRα family, GFRα3 is the most distantly related of the four family members. GFRα1 and GFRα2 share about 50% identity (Sanicola, M. et al., PNAS, USA, (1997), 94:6238-43; Klein, R D, et al., (1997), Nature, 387:717-21; Buj-Bello, A. et al., Nature (1997), 387:721-4; Baloh, R H, et al., Neuron, (1997), 18:793-802), while GFRα3 has only 32 and 37% identity, respectively, with these proteins (Masure, S. et al., Eur. J. Biochem., (1998), 251:622-30; Nomoto, S. et al., BBRC, (1998), 244:849-53). The amino acid sequence of mouse GFRα3 has the following Genbank Accession Number: NP_034410.3. The amino acid sequence of human GFRα1 has the following Genbank Accession Number: NP_005255.1 and is also found as SEQ ID NO: 376. The amino acid sequence of cynomolgus GFRα3 is shown in SEQ ID NO: 377 and the amino acid sequence of cynomolgus RET is shown in SEQ ID NO: 378.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR" or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the anti-GFRα3 antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully-human anti-hGFRα3 antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are back-mutated to the corresponding germline residue(s) or to a conservative amino acid substitution (natural or non-natural) of the corresponding germline residue(s) (such sequence changes are referred to herein as "germline back-mutations"). A person of ordinary skill in the art, starting with the heavy and light chain variable region sequences disclosed herein, can easily produce numerous antibodies and antigen-binding fragments which comprise one or more individual germline back-mutations or combinations thereof. In certain embodiments, all of the framework and/or CDR residues within the $V_H$ and/or $V_L$ domains are mutated back to the germline sequence. In other embodiments, only certain residues are mutated back to the germline sequence, e.g., only the mutated residues found within the first 8 amino acids of FR1 or within the last 8 amino acids of FR4, or to germline back-mutations within all framework regions FR1, FR2, FR3, FR4, or only the mutated residues found within CDR1, CDR2 or CDR3. Furthermore, the antibodies of the present invention may contain any combination of two or more germline back-mutations within the framework and/or CDR regions, i.e., wherein certain individual residues are mutated back to the germline sequence while certain other residues that differ from the germline sequence are maintained. Once obtained, antibodies and antigen-binding fragments that contain one or more germline back-mutations can be easily tested for one or more desired properties such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The anti-human GFRα3 antibodies of the invention may be designated as "anti-hGFRα3" or "anti-GFRα3".

The term "specifically binds," or the like, means that an antibody or antigen-binding fragment thereof forms a complex with an antigen that is relatively stable under physiologic conditions. Specific binding can be characterized by an equilibrium dissociation constant of at least about $1 \times 10^{-6}$ M or less (e.g., a smaller $K_D$ denotes a tighter binding). Methods for determining whether two molecules specifically bind are well known in the art and include, for example, equilibrium dialysis, surface plasmon resonance, and the like. An isolated antibody that specifically binds hGFRα3 may, however, exhibit cross-reactivity to other antigens such as GFRα3 molecules from other species. Moreover, multi-specific antibodies that bind to hGFRα3 and one or more additional antigens or a bi-specific that binds to two different regions of hGFRα3 are nonetheless considered antibodies that "specifically bind" hGFRα3, as used herein.

As used herein, the term "does not bind" to a specified target molecule (e.g. a particular GFRα3 peptide) means that the antibody, when tested for binding to the target molecule at 25° C. in a Plasmon resonance assay, exhibits a $K_D$ of greater than 500 nM, or if tested for binding to the target molecule at 25° C. in an enzyme linked immunosorbent assay (ELISA) exhibits an $EC_{50}$ of greater than 50 nM, or fails to exhibit any binding in either type of assay or equivalent thereof.

The term "high affinity" antibody refers to those mAbs having a binding affinity to hGFRα3 of at least $10^{-9}$ M; preferably $10^{-10}$M; more preferably $10^{-11}$M, even more preferably $10^{-12}$ M, as measured by surface plasmon resonance, e.g., BIACORE™ or solution-affinity ELISA.

By the term "slow off rate", "Koff" or "kd" is meant an antibody that dissociates from hGFRα3 with a rate constant of $1 \times 10^{-3}$ s$^{-1}$ or less, preferably $1 \times 10^{-4}$ s$^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding portion" of an antibody, or "antibody fragment", as used herein, refers to one or more fragments of an antibody that retain the ability to specifically bind to hGFRα3.

The specific embodiments, antibody or antibody fragments of the invention may be conjugated to a therapeutic moiety ("immunoconjugate"), such as an opioid, a COX-2 inhibitor, a local anesthetic, a cytokine antagonist, such as an IL-1 or IL-6 inhibitor, a second GFRα3 inhibitor, an NMDA modulator, a cannabinoid receptor agonist, a P2X family modulator, a VR1 antagonist, a substance P antagonist, a chemotherapeutic agent, or a radioisotope.

An "isolated antibody", as used herein, is intended to refer to an antibody that is substantially free of other antibodies (Abs) having different antigenic specificities (e.g., an isolated antibody that specifically binds hGFRα3, or a fragment thereof, is substantially free of Abs that specifically bind antigens other than hGFRα3).

A "neutralizing antibody", as used herein (or an "antibody that neutralizes GFRα3 activity"), is intended to refer to an antibody whose binding to hGFRα3 results in inhibition of at least one biological activity of GFRα3. This inhibition of the biological activity of GFRα3 can be assessed by measuring one or more indicators of GFRα3 biological activity by one or more of several standard in vitro or in vivo assays known in the art (see examples below).

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403 410 and (1997) Nucleic Acids Res. 25:3389 402, each of which is herein incorporated by reference.

In specific embodiments, the antibody or antibody fragment for use in the method of the invention may be mono-specific, bi-specific, or multi-specific. Multi-specific antibodies may be specific for different epitopes of one target polypeptide or may contain antigen-binding domains specific for epitopes of more than one target polypeptide. An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise an Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 mAbs; N44S, K52N, and V82I (IMGT; N384S, K392N, and V422I by EU) in the case of IgG2 mAbs; and Q15R, N44S, K52N, V57M, R69K, E79Q, and V82I (by IMGT; Q355R, N384S, K392N, V397M, R409K, E419Q, and V422I by EU) in the case of IgG4 mAbs. Variations on the bi-specific antibody format described above are contemplated within the scope of the present invention.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

The term "functional pain syndrome(s)", refers to chronic symptom-based syndromes that affect up to 15% of the population worldwide. They are characterized by chronic pain and discomfort referred to in different regions of the body. No generally agreed-upon structural, inflammatory, or biochemical abnormalities have been identified that could fully explain the symptoms. Patients show a greatly reduced quality of life, yet treatment options are limited, and the development of novel therapeutic approaches has been disappointing. Some of the common disorders, which fall into this category, include chronic low back pain, irritable bowel syndrome (IBS), fibromyalgia (FM), chronic fatigue syndrome, functional abdominal pain syndrome, temporomandibular joint disorder (TMJD), painful bladder syndrome (interstitial cystitis), functional gastrointestinal disorders/syndromes, functional rectal pain syndrome, functional chest pain syndrome, migraines and tension type headaches, chronic pelvic pain syndrome, painful prostate syndrome (chronic prostatitis), multiple chemical sensitivity syndrome, and Gulf War syndrome.

General Description

The glial cell line-derived neurotrophic factor related family includes glial cell line-derived neurotrophic factor (GDNF), neurturin (NRTN), persephin (PSPN), and artemin (ARTN). GDNF family proteins are differentially involved in the development and maintenance of sensory, enteric, sympathetic and parasympathetic neurons and a variety of non-neural tissues (Henderson, C. E., et al., (1994), Science 266:1062-1064; Kotzbauer, P. T. et al., (1996), Nature 384: 467-470; Springer, J. E., et al. (1994), Exp. Neurol. 127: 167-170; Schaar. D. G., et al., (1993), Exp. Neurol. 124: 368-371). GDNF is an especially potent survival factor for dopaminergic, noradrenergic and spinal motor neurons (Yan, Q. et al. (1995), Nature, 373:341-344; Henderson, C. E., et al., (1994), Science, 266:1062-1064; Buj-Bello, A. et al., (1995), Neuron, 15:821-828). Other GDNF family growth members have functions outside the nervous system (Trupp, M. et al., (1995), J. Cell Biol. 130:137-148; Kotzbauer, P. T. et al., (1996), Nature 384:467-470; Springer, J. E., et al. (1994), Exp. Neurol. 127:167-170; Schaar. D. G., et al., (1993), Exp. Neurol. 124:368-371). For example, NRTN, ARTN, and PSPN are also expressed in the developing kidney. GDNF also has critical roles outside the nervous system in the regulation of kidney morphogenesis and spermatogenesis (Airaksinen, M. S. et al., (2002), Nature Reviews 3:383-392).

Each member of the GDNF family binds preferentially to (ie, is a ligand for) a glycosylphosphatidylinositol (GPI)-anchored protein receptor dynamically associated with the plasma membrane. The GDNF-family receptor alpha family is composed of four different receptors: GFRalpha1 (GFRα1, GDNFR-alpha); GFRalpha2 (GFRα2/TrnR2/GD-NFR-beta/NTNR-alpha/RETL2); GFRalpha3 (GFRα3); and GFRalpha4 (GFRα4). GDNF binds preferentially to GFRα1, NRTN binds preferentially to GFRα2, ARTN binds preferentially to GFRα3 and PSPN binds preferentially to GFRα4 (Airaksinen, M. S., et al. Nature Reviews Neuroscience (2002), 3:383-394).

GFRα2 is highly expressed in cortex, basal forebrain, and specific layers of the olfactory bulb, and poorly expressed in substantia nigra, cerebellum, and motor nuclei. GFRα3 is expressed in fetal and adult mouse nerves, sympathetic and sensory ganglia, intestine, heart, brain, lung and kidney. GFRα4 is expressed at low levels in different brain areas in the adult as well as in some peripheral tissues including testis and heart. While the GDNF family member binding preferences are shown above to be GDNF to GFRα1; neurturin to GFRα2; artemin to GFRα3; and persephin to GFRα4, the ligand receptor pairing is not stringent (Airaksinen, M. S., et al. Nature Reviews Neuroscience (2002), 3:383-394). For example, GDNF binds to GFRα2 and GFRα3 with lower efficiencies than it binds to GFRα1.

The GDNF family ligands, typically but not exclusively, transmit their signals through multi-component complexes composed of a ligand, its GFR alpha receptor and the receptor tyrosine kinase, c-Ret. Ret is a common element of these ligand signaling complexes. Ret is a proto-oncogene that strongly activates anti-apoptotic signals through the activation of the phosphoinositol-3 kinases (PI3-K)/PDK/AKT(PKB) and the Ras/Raf/MEK/ERK pathways. Ret is also able to activate phospholipase C gamma (PLCgamma) which elevates intracellular calcium and facilitates activation of members of the conventional and novel protein kinase C (PKC) family. GDNF family ligand receptor complexes are not restricted to signaling through Ret. GDNF:GFRalpha1 can bind to NCAM in cells lacking RET and activate Fyn and FAK. Under some conditions GDNF:GFRalpha complexes directly activate src kinase.

In certain embodiments of the present invention, any one or more of the three globular cysteine-rich domains (1, 2, or 3) of GFRα3, or a fragment thereof, may be used to prepare antibodies that bind GFRα3 and inhibit its function, or inhibit its ability to bind its ligand, such as, artemin. In certain embodiments, an antibody of the invention specific for GFRα3 may bind to a ligand-binding domain on GFRα3, and as such, may block the binding of the ligand (artemin)-GFRα3 complex to RET. The full-length amino acid sequence of human GFRα3 is shown as SEQ ID NO: 375. The nucleic acid encoding human GFRα3 is shown in SEQ ID NO: 374. Domain 1 spans residues 44-124 of SEQ ID NO: 375; domain 2 spans residues 162-239 of SEQ ID NO: 375; domain 3 spans residues 248-340 of SEQ ID NO: 375. (See either SEQ ID NO. 375 or Genbank NP_001487.2).

Any of these domains, 1, 2, or 3, or fragments derived therefrom, may be used to prepare antibodies that bind specifically to GFRα3 and inhibit its activity, or at least one function associated with GFRα3. In certain embodiments, the antibodies of the invention bind specifically to GFRα3 and may prevent signaling mediated by GFRα3. In certain embodiments, the antibodies that bind specifically to GFRα3 may prevent binding of GFRα3 to its ligand, such as artemin (Wang, X. et al. Structure, (2006), 14:1083-1092). In certain embodiments, the antibodies that bind specifically to GFRα3 may prevent activation of the RET receptor tyrosine kinase. In certain embodiments, the antibodies of the invention may bind specifically to GFRα3 without preventing activation of the RET receptor tyrosine kinase. In certain embodiments, the antibodies of the invention may bind specifically to GFRα3 and prevent signaling through RET, or through a mediator other than RET. In certain embodiments, the antibodies of the invention may be used to inhibit tumor cell growth/proliferation and as such, may be useful for treating certain cancers/malignancies, or the pain associated with such cancers/malignancies, or the pain associated with metastasis of such cancers/malignancies (See Tang, J-Z, et al. Mol Cancer Ther (2010), 9(6): 1697-1708; Kang, J. et al. Oncogene, (2009), 28:2034-2045; Ceyhan, G. O. et al. Annals of Surgery, (2006), 244(2):274-281; Banerjee, A., et al. Breast Cancer Res (2011), 13:R112; Pandey, V. et al., Endocrinology, (2010), 151(3):909-920; Kang, J. et al., Oncogene, (2010), 29:3228-3240; Li, S. et al. J Biomed Sci (2011), 18:24). In certain embodiments, antibodies that bind specifically to GFRα3 may be prepared using fragments of the above-noted regions, or peptides that extend beyond the designated regions by about 10 to about 50 amino acid residues from either, or both, the N or C terminal ends of the regions described herein. In certain embodiments, any combination of the above-noted regions or fragments thereof may be used in the preparation of GFRα3 specific antibodies. As noted above, the length, or the number of amino acid residues encompassing the three domains of hGFRα3 may vary by about ten to fifty amino acid residues extending from either, or both, the N terminal or C terminal end of the full length domain, or a fragment thereof, for preparation of anti-hGFRα3 specific antibodies.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding portion" of an antibody, or "antibody fragment", as used herein, refers to one or more fragments of an antibody that retain the ability to specifically bind to hGFRα3. An antibody fragment may include a Fab fragment, a F(ab')$_2$ fragment, a Fv fragment, a dAb fragment, a fragment containing a CDR, or an isolated CDR. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR)). Other engineered molecules, such as diabodies, triabodies, tetrabodies and minibodies, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

Preparation of Human Antibodies

Methods for generating human antibodies in transgenic mice are known in the art. Any such known methods can be used in the context of the present invention to make human antibodies that specifically bind to human GFRα3.

Using VELOCIMMUNE™ technology or any other known method for generating monoclonal antibodies, high affinity chimeric antibodies to GFRα3 are initially isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies of the instant invention possess very high affinities, typically possessing $K_D$ of from about $10^{-13}$ through about $10^{-8}$ M, or from about $10^{-12}$ through about $10^{-9}$ M when measured by binding to antigen either immobilized on solid phase or in solution phase. The mouse constant regions are replaced with desired human constant regions to generate the fully human antibodies of the invention. While the constant region selected may vary according to specific use, high affinity antigen-binding and target specificity characteristics reside in the variable region.

Bioequivalents

The anti-GFRα3 antibodies and antibody fragments of the present invention encompass proteins having amino acid sequences that vary from those of the described antibodies, but that retain the ability to bind human GFRα3. Such variant antibodies and antibody fragments comprise one or more additions, deletions, or substitutions of amino acids when compared to parent sequence, but exhibit biological activity that is essentially equivalent to that of the described antibodies. Likewise, the anti-GFRα3 antibody-encoding DNA sequences of the present invention encompass sequences that comprise one or more additions, deletions, or substitutions of nucleotides when compared to the disclosed sequence, but that encode an anti-GFRα3 antibody or antibody fragment that is essentially bioequivalent to an anti-GFRα3 antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either as a single dose or as multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-GFRα3 antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-GFRα3 antibody variants comprising amino acid changes, which modify the glycosylation characteristics of the antibodies, e.g., mutations which eliminate or remove glycosylation.

Anti-GFRα3 Antibodies Comprising Fc Variants

According to certain embodiments of the present invention, anti-GFRα3 antibodies are provided comprising an Fc domain comprising one or more mutations, which enhance or diminish antibody binding to the FcRn receptor, e.g., at acidic pH as compared to neutral pH. For example, the present invention includes anti-GFRα3 antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes anti-GFRα3 antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

Biological Characteristics of the Antibodies

In general, the antibodies of the present invention may function by binding to any one or more of the three globular cysteine-rich domains (1, 2, or 3) of hGFRα3. In certain embodiments, the antibodies of the present invention may bind to an epitope located on at least one of the cysteine-rich domains of hGFRα3. In certain embodiments, an antibody of the invention may bind to amino acid residues of domain 1 of GFRα3, ranging from about residue 44 to about residue 124 of SEQ ID NO: 375. In certain embodiments, an antibody of the invention may bind to amino acid residues of domain 2 of GFRα3, ranging from about residue 162 to about residue 239 of SEQ ID NO: 375. In certain embodiments, an antibody of the invention may bind to amino acid residues of domain 3 of GFRα3, ranging from about residue 248 to about residue 340 of SEQ ID NO: 375. In certain embodiments, the antibodies of the present invention may function by blocking or inhibiting GFRα3 activity by binding to a region in any one of the domains that acts as the ligand binding domain, thus preventing binding of the ligand, such as, artemin, to that site. In certain embodiments, an antibody of the invention may bind to the ligand binding site on one of the domains of GFRα3 and prevent subsequent binding of the artemin-GFRα3 complex to RET. In one embodiment, an antibody of the invention may bind to any one or more of the epitopes in the artemin-GFRα3 complex that may determine or play a role in the specificity between ligand and GFRα3, such as in the region ranging from residues 167-184 of SEQ ID NO: 375. In certain embodiments, an antibody of the invention may bind to one or more of the residues of domain 2 that are responsible for the specificity between artemin and GFRα3, for example, the amino acid residues at positions 167 (met), 176 (asp) and/or position 184 (glu), of SEQ ID NO: 375 and in so binding, may prevent ligand binding to its receptor, and subsequently may prevent signaling through the RET receptor tyrosine kinase, or through a signaling mediator or modulator other than RET. In certain embodiments, the antibodies of the invention may bind to the membrane bound form of GFRα3 or to the soluble form of GFRα3. In certain embodiments, the antibodies of the invention may bind GFRα3, but do not cross react with GFRα1, GFRα2, or GFRα4. In certain embodiments, the antibodies of the present invention may be bi-specific antibodies. The bi-specific antibodies of the invention may bind one epitope in one cysteine rich region of one domain and may also bind one cysteine-rich region in a second domain of hGFRα3. In certain embodiments, the bi-specific antibodies of the invention may bind to two different regions within the same domain. In certain embodiments, one arm of a bi-specific antibody of the invention may bind to one cysteine rich region of one domain of hGFRα3 and the other arm may bind to RET, or to a modulator other than RET. In certain embodiments, the bispecific antibodies may bind one domain in GFRα3 and one domain in GFRα1 or GFRα2.

More specifically, the anti-GFRα3 antibodies of the invention may exhibit one or more of the following characteristics:

(i) exhibits a $K_D$ ranging from about $10^{-8}$M to about $10^{-13}$M as measured by surface plasmon resonance;

(ii) demonstrates the ability to block about 50-100% of the binding of GFRα3 to its ligand, artemin, with an IC$_{50}$ value ranging from about 40 pM to about 15 nM;

(iii) demonstrates the ability to block about 20% to about 100% of the binding of GFRα3 to a solid support coated with a mixture of artemin and RET;

(iv) blocks or inhibits artemin-dependent activation of RET with an IC$_{50}$ ranging from about 200 pM to about 50 nM;

(v) inhibits or reduces one or more nociceptive responses in an in vivo model of bone cancer pain;

(vi) inhibits or reduces artemin-sensitized thermal hyperalgesia in vivo;

(vii) inhibits or reduces allodynia in an in vivo model of osteoarthritis;

(viii) does not cross-react with other GFR co-receptors for RET;

(ix) comprises a heavy chain variable region (HCVR) having an amino acid sequence selected from the group consisting of SEQ ID NO: 2, 18, 34, 50, 66, 82, 98, 114, 130, 146, 162, 178, 194, 210, 226, 242, 258, 274, 290, 306, 322, 338, 354, 381 and 397; or (x) comprises a light chain variable region (LCVR) having an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 389 and 405.

Certain anti-GFRα3 antibodies of the present invention are able to inhibit or attenuate GFRα3 activity in an in vitro assay. The ability of the antibodies of the invention to bind to and inhibit the binding of GFRα3 to its ligand artemin alone or in the presence of RET may be measured using any standard method known to those skilled in the art, including binding assays, or assays to determine if the antibodies block the activation of RET by inhibiting the binding of GFRα3 to its receptor artemin, such as those described herein. Non-limiting, exemplary in vitro assays for measuring GFRα3 activity are illustrated in Examples 4 and 5, below.

The present invention includes anti-GFRα3 antibodies and antigen binding fragments thereof which bind to one or more of the cysteine rich globular domains of GFRα3, as shown in SEQ ID NO: 375, or to a fragment thereof. The antibodies specific for GFRα3 may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

In one embodiment, the invention provides a fully human monoclonal antibody or antigen-binding fragment thereof that specifically binds hGFRα3 and neutralizes hGFRα3 activity, wherein the antibody or fragment thereof exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 194, 210, 226, 242, 258, 274, 290, 306, 322, 338, 354, 381 and 397; (ii) comprises a LCVR having an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 389 and 405; (iii) comprises any one or more of the heavy or light chain CDR1, CDR2, and CDR3 sequences depicted in Table 1 and combinations thereof; (iv) is specific for binding to and/or blocking GFRα3 activity without binding to and/or blocking other GFR alpha receptors, including GFRα1, GFRα2 and GFRα4; (v) demonstrates binding specificity for any one or more of the cysteine-rich globular domains of GFRα3; (vi) blocks activation of and signaling through the RET receptor tyrosine kinase; (vii) inhibits or reduces artemin-sensitized thermal hyperalgesia in vivo; (viii) inhibits or reduces allodynia in an in vivo model of osteoarthritis; or inhibits or reduces one or more nociceptive responses in an in vivo model of bone cancer pain.

Epitope Mapping and Related Technologies

Various techniques known to persons of ordinary skill in the art can be used to determine whether an antibody "interacts with one or more amino acids" within a polypeptide or protein. Exemplary techniques include, for example, a routine cross-blocking assay such as that described *Antibodies*, Harlow and Lane (Cold Spring Harbor Press, Cold Spring Harb., N.Y.) can be performed. Other methods include alanine scanning mutational analysis, peptide blot analysis (Reineke (2004) Methods Mol Biol 248:443-63), peptide cleavage analysis crystallographic studies and NMR analysis. In addition, methods such as epitope excision, epitope extraction and chemical modification of antigens can be employed (Tomer (2000) Protein Science 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues that correspond to the specific amino acids with which the antibody interacts. See, e.g., Ehring (1999) *Analytical Biochemistry* 267(2):252-259; Engen and Smith (2001) *Anal. Chem.* 73:256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the invention into groups of antibodies binding different epitopes.

In certain embodiments, the anti-GFRα3 antibody or antigen-binding fragment of an antibody binds an epitope within at least one of the GFRα3 cysteine rich domains 1, 2, or 3, or a fragment thereof, wherein domain 1 ranges from about residue number 44 to about residue number 124 of SEQ ID NO: 375; domain 2 ranges from about residue number 162 to about residue number 239 of SEQ ID NO: 375; domain 3 ranges from about residue number 248 to about residue number 340 of SEQ ID NO: 375.

In certain embodiments, the anti-GFRα3 antibody or antigen-binding fragment of an antibody binds an epitope within domain 1, or a fragment thereof, of human GFRα3.

In certain embodiments, the anti-GFRα3 antibody or antigen-binding fragment of an antibody binds an epitope within domain 2, or a fragment thereof, of human GFRα3.

In certain embodiments, the anti-GFRα3 antibody or antigen-binding fragment of an antibody binds an epitope within domain 3, or a fragment thereof, of human GFRα3.

In certain embodiments, the antibody or antibody fragment binds an epitope, which includes more than one of the enumerated epitopes of GFRα3 within domain 1, 2, or 3, and/or within two different domains (for example, epitopes within the 1 and 2 domains, or within the 2 and 3 domains, or within the 1 and 3 domains).

In certain embodiments, the antibody is a bi-specific antibody that binds one epitope within one domain of GFRα3 and another epitope within a different domain of GFRα3. In one embodiment, the antibody is a bi-specific antibody that binds one epitope in domain 1 of GFRα3 and another epitope in domain 2 of GFRα3. In one embodiment, the antibody is a bi-specific antibody that binds one epitope in domain 1 of GFRα3 and another epitope within domain 3 of GFRα3. In one embodiment, the antibody is a bi-specific antibody that binds one epitope in domain 2 of GFRα3 and another epitope within domain 3 of GFRα3.

The present invention includes anti-GFRα3 antibodies that bind to the same epitope as any of the specific exemplary antibodies described herein (e.g., H4H2207N, H4H2212N, H4H2236N3, H4H2243N2, H4H2210N, H4H2234N, H4H2291S, H4H2292S, H4H2293P, H4H2294S, H4H2295S, H4H2296S, H4H2341S, H4H2342P, H4H2344S, H4H2345S, H4H2346S, H4H2350P, H4H2352S, H4H2354S, H4H2355S, H4H2357S, H4H2364S, H1M2243N and H1M2236N). Likewise, the present invention also includes anti-GFRα3 antibodies that compete for binding to GFRα3 or a GFRα3 fragment with any of the specific exemplary antibodies described herein.

One can easily determine whether an antibody binds to the same epitope as, or competes for binding with, a reference anti-GFRα3 antibody by using routine methods known in the art. For example, to determine if a test antibody binds to the same epitope as a reference anti-GFRα3 antibody of the invention, the reference antibody is allowed to bind to a GFRα3 protein or peptide under saturating conditions. Next, the ability of a test antibody to bind to the GFRα3 molecule is assessed. If the test antibody is able to bind to GFRα3 following saturation binding with the reference anti-GFRα3 antibody, it can be concluded that the test antibody binds to a different epitope than the reference anti-GFRα3 antibody. On the other hand, if the test antibody is not able to bind to the GFRα3 molecule following saturation binding with the reference anti-GFRα3 antibody, then the test antibody may bind to the same epitope as the epitope bound by the reference anti-GFRα3 antibody of the invention.

To determine if an antibody competes for binding with a reference anti-GFRα3 antibody, the above-described binding methodology is performed in two orientations: In a first orientation, the reference antibody is allowed to bind to a GFRα3 molecule under saturating conditions followed by assessment of binding of the test antibody to the GFRα3 molecule. In a second orientation, the test antibody is allowed to bind to a GFRα3 molecule under saturating conditions followed by assessment of binding of the reference antibody to the GFRα3 molecule. If, in both orientations, only the first (saturating) antibody is capable of binding to the GFRα3 molecule, then it is concluded that the test antibody and the reference antibody compete for binding to GFRα3. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Species Selectivity and Species Cross-Reactivity

According to certain embodiments of the invention, the anti-GFRα3 antibodies bind to human GFRα3 but not to GFRα3 from other species. Alternatively, the anti-GFRα3 antibodies of the invention, in certain embodiments, bind to human GFRα3 and to GFRα3 from one or more non-human species. For example, the anti-GFRα3 antibodies of the invention may bind to human GFRα3 and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee GFRα3.

Immunoconjugates

The invention encompasses a human anti-GFRα3 monoclonal antibody conjugated to a therapeutic moiety ("immunoconjugate"), such as an agent that is capable of reducing pain and/or inflammation, a chemotherapeutic drug, or a radioisotope. The type of therapeutic moiety that may be conjugated to the anti-GFRα3 antibody will take into account the condition to be treated and the desired therapeutic effect to be achieved. For example, for treating acute or chronic pain, an agent such as an NSAID, an opioid, or a Cox-2 inhibitor, or a local anesthetic agent, or a second GFRα3 inhibitor may be conjugated to the GFRα3 antibody. Alternatively, if the desired therapeutic effect is to treat the inflammation associated with a painful condition, it may be advantageous to conjugate an anti-inflammatory agent to the anti-GFRα3 antibody, such as, but not limited to, celecoxib, or a cytokine antagonist, such as an IL-1 or an IL-6 inhibitor. If the condition to be treated is a cancerous condition, it may be beneficial to conjugate a chemotherapeutic drug, or a radioisotope to the GFRα3 antibody. Examples of suitable agents for forming immunoconjugates are known in the art, see for example, WO 05/103081.

Multi-Specific Antibodies

The antibodies of the present invention may be monospecific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-GFRα3 antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multi-specific antibody with a second binding specificity. For example, the present invention includes bi-specific antibodies wherein one arm of an immunoglobulin is specific for human GFRα3 or a fragment thereof, and the other arm of the immunoglobulin is specific for a second therapeutic target or is conjugated to a therapeutic moiety. In certain embodiments of the invention, one arm of an immunoglobulin is specific for an epitope on one domain of hGFRα3 or a fragment thereof, and the other arm of the immunoglobulin is specific for an epitope on a second domain of hGFRα3. In certain embodiments, one arm of an immunoglobulin is specific for one epitope on one domain of hGFRα3 and the other arm is specific for a second epitope on the same domain of hGFRα3.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Therapeutic Administration and Formulations

The invention provides therapeutic compositions comprising the anti-GFRα3 antibodies or antigen-binding fragments thereof of the present invention. The administration of therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When the antibody of the present invention is used for treating pain associated with GFRα3 activity in various conditions and diseases, wherein the condition or disease results in acute or chronic pain, inflammatory pain, neuropathic pain, and the like, in an adult patient, it is advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see, for example, Langer (1990) Science 249:1527-1533).

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousands Oaks, Calif.), the PENLET™ (Haselmeier, Stuttgart, Germany), the EPIPEN (Dey, L.P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The antibodies of the invention are useful for the treatment, prevention and/or amelioration of any disease, disorder, or condition associated with GFRα3 activity, or for amelioration of at least one symptom associated with the disease, disorder, or condition, or for alleviating the pain associated with such disease, disorder, or condition. Exemplary conditions, diseases and/or disorders, and/or the pain associated with such conditions, diseases, or disorders, that can be treated with the anti-GFRα3 antibodies of the present invention include acute, chronic, neuropathic, or inflammatory pain, arthritis, interstitial cystitis, pancreatitis, migraine, cluster headaches, trigeminal neuralgia, herpetic neuralgia, general neuralgias, epilepsy or epileptic conditions, myotonia, arrhythmia, movement disorders, neuroendocrine disorders, ataxia, irritable bowel syndrome, inflammatory bowel syndrome, fecal urgency, incontinence, rectal hypersensitivity, visceral pain, osteoarthritis pain, gout, post-herpetic neuralgia, diabetic neuropathy, radicular pain, sciatica, back pain, head or neck pain, breakthrough pain, post-surgical pain, cancer pain, including pain associated with bone cancer or pancreatic cancer.

Other conditions treatable by the therapeutic methods of the invention included hereditary erythromelalgia, rhinitis, prostate cancer, breast cancer, bone cancer, cervical cancer, or bladder disorders. The antibodies of the invention or antigen-binding fragments thereof may also be used to treat the following conditions: non-malignant acute, chronic, or fracture bone pain; rheumatoid arthritis, spinal stenosis; neuropathic low back pain; myofascial pain syndrome; fibromyalgia; temporomandibular joint pain; visceral pain, including, abdominal; pancreatic; chronic headache pain; tension headache, including, cluster headaches; diabetic neuropathy; HIV-associated neuropathy; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome (CRPS); phantom pain; intractable pain; musculoskeletal pain; joint pain; acute gout pain; mechanical low back pain; neck pain; tendonitis; injury/exercise pain; abdominal pain; pyelonephritis; appendicitis; cholecystitis; intestinal obstruction; hernias; etc; chest pain, including, cardiac pain; pelvic pain, renal colic pain, acute obstetric pain, including, labor pain; cesarean section pain; burn and trauma pain; endometriosis; herpes zoster pain; sickle cell anemia; acute pancreatitis; breakthrough pain; orofacial pain including sinusitis pain, dental pain; multiple sclerosis pain; leprosy pain; Behcet's disease pain; adiposis dolorosa; phlebitic pain; Guillain-Barre pain; painful legs and moving toes; Haglund syndrome; Fabry's disease pain; bladder and urogenital disease; hyperactivity bladder.

In one embodiment the antibodies of the invention may be used to treat a functional pain syndrome, wherein the functional pain syndrome is selected from the group consisting of chronic low back pain, irritable bowel syndrome (IBS), fibromyalgia (FM), chronic fatigue syndrome (CFS), abdominal pain, temporomandibular joint disorder (TMJD), painful bladder syndrome (interstitial cystitis), functional gastrointestinal disorders/syndromes, functional chest pain syndrome, migraines and tension type headaches, chronic pelvic pain syndrome, painful prostate syndrome (chronic prostatitis), multiple chemical sensitivity syndrome and Gulf War syndrome.

The antibodies of the invention or antigen-binding fragments thereof may also be used to inhibit tumor cell growth/ proliferation or metastasis of tumor cells. Accordingly, in certain embodiments, the antibodies of the invention or antigen-binding fragments thereof, may be used to treat a cancer, including, but not limited to, endometrial cancer, prostate cancer, breast cancer, cervical cancer, liver cancer, pancreatic cancer, colon cancer, stomach cancer, uterine cancer, ovarian cancer, kidney cancer, non-small cell lung cancer, brain cancer, a leukemia, a lymphoma, bone cancer, or pain associated with metastasis of a cancer, for example, metastasis of a cancer to the bone. (See Tang, J-Z, et al. Mol Cancer Ther (2010), 9(6): 1697-1708; Kang, J. et al. Oncogene, (2009), 28:2034-2045; Ceyhan, G. O. et al. Annals of Surgery, (2006), 244(2):274-281; Banerjee, A., et al. Breast Cancer Res (2011), 13:R112; Pandey, V. et al., Endocrinology, (2010), 151(3):909-920; Kang, J. et al., Oncogene, (2010), 29:3228-3240; Li, S. et al. J Biomed Sci (2011), 18:24).

The antibodies of the present invention are also useful for treating or preventing cancer-associated pain. "Cancer-associated pain" includes, e.g., bone cancer pain, including pain from cancer that has metastasized to bone (e.g., breast cancer, prostate cancer, lung cancer, sarcoma, kidney cancer, multiple myeloma, etc.). "Cancer-associated pain" also includes pain more generally associated with cancerous conditions such as, e.g., renal cell carcinoma, pancreatic carcinoma, breast cancer, head and neck cancer, prostate cancer, malignant gliomas, osteosarcoma, colorectal cancer, gastric cancer, malignant mesothelioma, multiple myeloma, ovarian cancer, small cell lung cancer, non-small cell lung cancer, synovial sarcoma, thyroid cancer, or melanoma. The antibodies of the present invention are also useful for treating or preventing pain caused by or associated with cancer therapy or anti-cancer medical treatments, e.g., chemotherapy-induced neuropathic pain such as pain caused by or associated with treatment with paclitaxel (TAXOL™), docetaxel (TAXOTERE®); nitrosourea, cyclophosphamide, doxorubicin, epirubicin, 5-fluorouracil, topotecan, irinotecan, carmustine, estramustine, and platinum-based chemotherapeutic compounds, such as cisplatin, carboplatin, and iproplatin.

Combination Therapies

Combination therapies may include an anti-hGFRα3 antibody of the invention and, for example, another GFRα3 antagonist (e.g., anti-GFRα3 antibody or small molecule inhibitor of GFRα3); a COX-2 inhibitor; a local anesthetic; an NMDA modulator; a cannabinoid receptor agonist; a P2X family modulator; a VR1 antagonist; a substance P antagonist; an inhibitor of a voltage-gated sodium channel ($Na_v$), for example, a $Na_v1.7$ antagonist, or a $Na_v1.8$ antagonist (e.g., anti-$Na_v1.7$ or anti-$Na_v1.8$ antibody or small molecule inhibitor), a $Na_v1.9$ antagonist (e.g., anti-$Na_v1.9$ antibody or small molecule inhibitor of $Na_v1.9$); a calcium channel inhibitor; a potassium channel inhibitor; a cytokine inhibitor or cytokine receptor antagonist (e.g., an interleukin-1 (IL-1) inhibitor (such as rilonacept ("IL-1 trap"; Regeneron) or anakinra (KINERET®, Amgen), a small molecule IL-1 antagonist, or an anti-IL-1 antibody); an IL-18 inhibitor (such as a small molecule IL-18 antagonist or an anti-IL-18 antibody); an IL-6 or IL-6R inhibitor (such as a small molecule IL-6 antagonist, an anti-IL-6 antibody or an anti-IL-6 receptor antibody); an antiepileptic/anti-convulsant drug (e.g., gabapentin, pregabalin); a nerve growth factor (NGF) inhibitor (e.g., a small molecule NGF antagonist or an anti-NGF antibody); an inhibitor of BDNF, TrkA, TrkB or p75; an opioid; morphine; low dose cochicine; aspirin or another NSAID; steroids (e.g., prednisone, methotrexate, etc.); low dose cyclosporine A; a selective serotonin reuptake inhibitor (SSRI); a serotonin norepinephrine reuptake inhibitor (SNRI); a tricyclic; a tumor necrosis factor (TNF) or TNF receptor inhibitor (e.g., a small molecule TNF or TNFR antagonist or an anti-TNF or TNFR antibody); an inhibitor of TWEAK (TNF-related WEAK inducer of apoptosis); a RET inhibitor; an inhibitor of a GDNF family ligand; an inhibitor of GFRα1, GFRα2 or GFRα4; an inhibitor of an acid sensing ion channel (e.g. ASIC1 or ASIC3; uric acid synthesis inhibitors (e.g., allopurinol); uric acid excretion promoters (e.g., probenecid, sulfinpyrazone, benzbromarone, etc.); an inhibitor of a prekineticin receptor (PROK1 and PROK2); other inflammatory inhibitors (e.g., inhibitors of caspase-1, p38, IKK1/2, CTLA-4Ig, etc.); and/or corticosteroids.

Administration Regimens

According to certain embodiments of the present invention, multiple doses of an anti-GFRα3 antibody may be administered to a subject over a defined time course. The methods according to this aspect of the invention comprise sequentially administering to a subject multiple doses of an anti-GFRα3 antibody. As used herein, "sequentially administering" means that each dose of anti-GFRα3 antibody is administered to the subject at a different point in time, e.g., on different days separated by a predetermined interval (e.g., hours, days, weeks or months). The present invention includes methods which comprise sequentially administering to the patient a single initial dose of an anti-GFRα3 antibody, followed by one or more secondary doses of the anti-GFRα3 antibody, and optionally followed by one or more tertiary doses of the anti-GFRα3 antibody.

The terms "initial dose," "secondary doses," and "tertiary doses," refer to the temporal sequence of administration of the anti-GFRα3 antibody. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-GFRα3 antibody, but generally may differ from one another in terms of frequency of administration. In certain embodiments, however, the amount of anti-GFRα3 antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-GFRα3 antibody, which is administered to a patient prior to the administration of the very next dose in the sequence with no intervening doses.

The methods according to this aspect of the invention may comprise administering to a patient any number of secondary and/or tertiary doses of an anti-GFRα3 antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient.

Diagnostic Uses of the Antibodies

The anti-GFRα3 antibodies of the present invention may also be used to detect and/or measure GFRα3 in a sample, e.g., for diagnostic purposes. For example, an anti-GFRα3 antibody, or fragment thereof, may be used to diagnose a condition or disease characterized by aberrant expression (e.g., over-expression, under-expression, lack of expression, etc.) of GFRα3. Exemplary diagnostic assays for GFRα3 may comprise, e.g., contacting a sample, obtained from a patient, with an anti-GFRα3 antibody of the invention, wherein the anti-GFRα3 antibody is labeled with a detectable label or reporter molecule. Alternatively, an unlabeled anti-GFRα3 antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure GFRα3 in a sample include enzyme-linked immunosorbent assay (ELISA), radioimmunoassay (RIA), and fluorescence-activated cell sorting (FACS).

Samples that can be used in GFRα3 diagnostic assays according to the present invention include any tissue or fluid sample obtainable from a patient, which contains detectable quantities of GFRα3 protein, or fragments thereof, under normal or pathological conditions. Generally, levels of GFRα3 in a particular sample obtained from a healthy patient (e.g., a patient not afflicted with a disease or condition associated with abnormal GFRα3 levels or activity) will be measured to initially establish a baseline, or standard, level of GFRα3. This baseline level of GFRα3 can then be compared against the levels of GFRα3 measured in samples obtained from individuals suspected of having a GFRα3 related disease or condition, or pain associated with such disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Generation of Human Antibodies to Human GFRα3

An immunogen comprising any one of the GFRα3 peptides having amino acid sequences shown as SEQ ID NOS: 370, 371, 372 and 373, or fragments thereof, may be utilized to generate antibodies to human GFRα3. These peptides are conjugated to a carrier, for example, KLH, then administered with an adjuvant to stimulate the immune response, to a VELOCIMMUNE® mouse comprising DNA encoding human Immunoglobulin heavy and kappa light chain variable regions. The antibody immune response is monitored by a GFRα3-specific immunoassay. When a desired immune response is achieved, splenocytes are harvested and fused with mouse myeloma cells to preserve their viability and form hybridoma cell lines. The hybridoma cell lines are screened and selected to identify cell lines that produce GFRα3-specific antibodies. Using this technique several anti-GFRα3 chimeric antibodies (i.e., antibodies possessing human variable domains and mouse constant domains) were obtained. The anti-GFRα3 antibodies generated using this method were designated H1M2207N, H1M2212N, H1M2236N, H1M2236N3, H1M2243N, H1M2243N2, H1M2210N and H1M2234N.

Anti-GFRα3 antibodies were also isolated directly from antigen-positive B cells without fusion to myeloma cells, as described in U.S. 2007/0280945A1, herein specifically incorporated by reference in its entirety. Using this method, several fully human anti-GFRα3 antibodies (i.e., antibodies possessing human variable domains and human constant domains) were obtained; exemplary antibodies generated in this manner were designated as follows: H4H2207N, H4H2212N, H4H2236N, H4H2243N, H4H2210N, H4H2234N, H4H2291S, H4H2292S, H4H2293P, H4H2294S, H4H2295S, H4H2296S, H4H2341S, H4H2342P, H4H2344S, H4H2345S, H4H2346S, H4H2350P, H4H2352S, H4H2354S, H4H2355S, H4H2357S and H4H2364S.

The biological properties of the exemplary anti-GFRα3 antibodies generated in accordance with the methods of this Example are described in detail in the Examples set forth below.

Example 2

Heavy and Light Chain Variable Region Amino Acid Sequences

Table 1 sets forth the heavy and light chain variable region amino acid sequence pairs of selected anti-GFRα3 antibodies and their corresponding antibody identifiers. Antibodies are typically referred to herein according to the following nomenclature: Fc prefix (e.g. "H4H", "H1M", "H2M"), followed by a numerical identifier (e.g. "2207" as shown in Table 1), followed by a "P", "S", or "N" suffix. Thus, according to this nomenclature, an antibody may be referred to as, e.g. "H4H2207N". The H4H, H1M, and H2M prefixes on the antibody designations used herein indicate the particular Fc region of the antibody. For example, an "H2M" antibody has a mouse IgG2 Fc, whereas an "H4H" antibody has a human IgG4 Fc. As will be appreciated by a person of ordinary skill in the art, an H1M or H2M antibody can be converted to an H4H antibody, and vice versa, but in any event, the variable domains (including the CDRs), which are indicated by the numerical identifiers shown in Table 1, will remain the same. Antibodies having the same numerical antibody designation, but differing by a letter suffix of N, B, S or P refer to antibodies having heavy and light chains with identical CDR sequences but with sequence variations in regions that fall outside of the CDR sequences (i.e., in the framework regions). Thus, N, B, S and P variants of a particular antibody have identical CDR sequences within their heavy and light chain variable regions but differ from one another within their framework regions.

TABLE 1

| Antibody Designation | AMINO ACID SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4H2207N | 2 | 4 | 6 | 8 | 10 | 12 | 14 | 16 |
| H4H2212N | 18 | 20 | 22 | 24 | 26 | 28 | 30 | 32 |
| H4H2236N3 | 34 | 36 | 38 | 40 | 42 | 44 | 46 | 48 |
| H4H2243N2 | 50 | 52 | 54 | 56 | 58 | 60 | 62 | 64 |
| H4H2210N | 66 | 68 | 70 | 72 | 74 | 76 | 78 | 80 |
| H4H2234N | 82 | 84 | 86 | 88 | 90 | 92 | 94 | 96 |
| H4H2291S | 98 | 100 | 102 | 104 | 106 | 108 | 110 | 112 |
| H4H2292S | 114 | 116 | 118 | 120 | 122 | 124 | 126 | 128 |
| H4H2293P | 130 | 132 | 134 | 136 | 138 | 140 | 142 | 144 |
| H4H2294S | 146 | 148 | 150 | 152 | 154 | 156 | 158 | 160 |
| H4H2295S | 162 | 164 | 166 | 168 | 170 | 172 | 174 | 176 |
| H4H2296S | 178 | 180 | 182 | 184 | 186 | 188 | 190 | 192 |
| H4H2341S | 194 | 196 | 198 | 200 | 202 | 204 | 206 | 208 |
| H4H2342P | 210 | 212 | 214 | 216 | 218 | 220 | 222 | 224 |
| H4H2344S | 226 | 228 | 230 | 232 | 234 | 236 | 238 | 240 |
| H4H2345S | 242 | 244 | 246 | 248 | 250 | 252 | 254 | 256 |
| H4H2346S | 258 | 260 | 262 | 264 | 266 | 268 | 270 | 272 |
| H4H2350P | 274 | 276 | 278 | 280 | 282 | 284 | 286 | 288 |
| H4H2352S | 290 | 292 | 294 | 296 | 298 | 300 | 302 | 304 |
| H4H2354S | 306 | 308 | 310 | 312 | 314 | 316 | 318 | 320 |
| H4H2355S | 322 | 324 | 326 | 328 | 330 | 332 | 334 | 336 |
| H4H2357S | 338 | 340 | 342 | 344 | 346 | 348 | 350 | 352 |
| H4H2364S | 354 | 356 | 358 | 360 | 362 | 364 | 366 | 368 |
| H1M2243N | 381 | 383 | 385 | 387 | 389 | 391 | 393 | 395 |
| H1M2236N | 397 | 399 | 401 | 403 | 405 | 407 | 409 | 411 |

Example 2

Variable Gene Utilization Analysis

To analyze the structure of antibodies produced, the nucleic acids encoding antibody variable regions were cloned and sequenced. From the nucleic acid sequence and predicted amino acid sequence of the antibodies, gene usage was identified for each Heavy Chain Variable Region (HCVR) and Light Chain Variable Region (LCVR). Table 2 sets forth the gene usage for selected antibodies in accordance with the invention.

TABLE 2

| AbPID | HCVR | | | LCVR | |
|---|---|---|---|---|---|
| | $V_H$ | $D_H$ | $J_H$ | $V_K$ | $J_K$ |
| H1M2207N | 3-9 | 6-6 | 4 | 1-5 | 2 |
| H1M2212N | 3-23 | 1-26 | 4 | 4-1 | 1 |
| H1M2236N | 3-23 | 3-3 | 6 | 1-16 | 4 |
| H4H2236N | 3-23 | 3-3 | 6 | 1-16 | 4 |
| H1M2243N | 1-18 | 6-6 | 6 | 1-16 | 3 |
| H4H2243N | 1-18 | 6-6 | 6 | 1-16 | 3 |
| H2M2210N | 3-23 | 1-20 | 3 | 3-20 | 4 |
| H2M2234N | 3-23 | 5-18 | 4 | 4-1 | 1 |
| H4H2291S | 3-23 | 6-6 | 6 | 1D-12 | 4 |
| H4H2292S | 3-33 | 1-7 | 3 | 1-39 | 3 |
| H4H2293P | 3-33 | 2-15 | 3 | 1-39 | 2 |
| H4H2294S | 3-23 | 6-6 | 6 | 1D-12 | 3 |
| H4H2295S | 3-23 | 6-6 | 6 | 1D-12 | 3 |
| H4H2296S | 3-23 | 6-6 | 6 | 1D-12 | 3 |
| H4H2341S | 1-69 | 3-10 | 5 | 1-39 | 5 |
| H4H2342P | 3-23 | 1-26 | 4 | 1-27 | 3 |
| H4H2344S | 3-33 | 2-15 | 3 | 1-39 | 2 |
| H4H2345S | 3-9 | 1-26 | 4 | 1-27 | 4 |
| H4H2346S | 3-33 | 2-15 | 3 | 1-39 | 2 |
| H4H2350P | 4-59 | 2-21 | 4 | 1-9 | 1 |
| H4H2352S | 1-18 | 3-3 | 3 | 3-20 | 2 |
| H4H2354S | 3-33 | 2-15 | 3 | 1-39 | 2 |
| H4H2355S | 3-23 | 6-6 | 4 | 1-5 | 4 |
| H4H2357S | 3-23 | 3-10 | 6 | 1-12 | 4 |
| H4H2364S | 3-23 | 6-6 | 6 | 1D-12 | 3 |

Example 3

Binding Affinities of GFRα3 Antibodies

Binding associative and dissociative rate constants ($k_a$ and $k_d$, respectively) and calculated equilibrium dissociation constants and dissociative half-lives ($K_D$ and $t_{1/2}$, respectively) for antigen binding to anti-GFRα3 antibodies were determined using a real-time surface plasmon resonance biosensor (Biacore T200) assay at 25° C. and 37° C. Antibodies were tested for binding to human GFRα3 expressed with either a C-terminal myc-myc-hexahistidine tag (hGFRα3-mmh; SEQ ID: 370, a C-terminal hFc tag (hGFRα3-hFc; SEQ ID:371), or a C-terminal mFc tag (hGFRα3-mFc; SEQ ID:372), as well as monkey GFRα3 expressed with a C-terminal myc-myc-hexahistidine tag (MfGFRα3-mmh; SEQ ID:373). Anti-GFRα3 antibodies were captured on either a goat anti-mouse IgG polyclonal antibody (GE Healthcare, # BR-1008-38) or a mouse anti-human IgG monoclonal antibody (GE Healthcare, #BR-1008-39) surface created through direct amine coupling to a Biacore CM5 sensor chip. Kinetic experiments were carried out using HBS-EP (10 mM HEPES, 150 mM NaCl, 3 mM EDTA, 0.05% Surfactant P20, at pH 7.4) or PBS buffer containing 0.05% v/v surfactant P20 as both the running buffer and the sample buffer. Binding to human GFRα3-mmh or monkey GFRα3-mmh was evaluated by injecting several concentrations ranging from 200 to 7.4 nM (3-fold dilutions) across the captured antibody surface. Binding to human GFRα3-mFc or human GFRα3-hFc was evaluated by injecting several concentrations ranging from 100 to 3.7 nM (3-fold dilutions) across the captured antibody surface. Antibody-antigen association was monitored for up to 4 minutes, while dissociation in buffer was monitored for up to 20 minutes. Kinetic association ($k_a$) and dissociation ($k_d$) rate constants were determined by processing and fitting the data to a 1:1 binding model using Scrubber 2.0c curve fitting software. Binding dissociation equilibrium constants ($K_D$) and dissociative half-lives ($t_{1/2}$) were calculated from the kinetic rate constants as: $K_D$ (M)=$k_d/k_a$ and $t_{1/2}$ (min)=[ln 2/(60*$k_d$)].

As shown in Table 3, at 25° C., all 25 anti-GFRα3 antibodies bound to hGFRα3-mmh with $K_D$ values ranging from 82.0 pM to 29.7 nM. At 37° C., all 25 anti-GFRα3 antibodies bound to hGFRα3-mmh with $K_D$ values ranging from 118 pM to 47.3 nM. As shown in Table 4, at 25° C., all 23 anti-GFRα3 antibodies bound to MfGFRα3-mmh with $K_D$ values ranging from 2.90 pM to 97.2 nM. At 37° C., all 23 anti-GFRα3 antibodies bound to MfGFRα3-mmh with $K_D$ values ranging from 11.7 pM to 145 nM. As shown in Table 5, at 25° C. and 37° C., 6 of the 23 anti-GFRα3 antibodies were tested for binding to hGFRα3-hFc, while the other 17 antibodies were tested for binding to hGFRα3-mFc. At 25° C., the 6 anti-GFRα3 antibodies tested for binding to hGFRα3-hFc bound with $K_D$ values ranging from 7.50 pM to 220 pM. At 37° C., the 6 anti-GFRα3 antibodies tested for binding to hGFRα3-hFc bound with $K_D$ values ranging from 41.3 pM to 531 pM. At 25° C., the 17 anti-GFRα3 antibodies tested for binding to hGFRα3-mFc bound with $K_D$ values ranging from 0.467 pM to 58.4 pM. At 37° C., the 17 anti-GFRα3 antibodies tested for binding to hGFRα3-mFc bound with $K_D$ values ranging from 13.2 pM to 106 pM.

TABLE 3

Kinetics of hGFRα3-mmH binding to different anti-GFRα3 antibodies at 25° C. and at 37° C.

| | 25° C. | | | | 37° C. | | | |
| --- | --- | --- | --- | --- | --- | --- | --- | --- |
| AbPID | $k_a$ (1/Ms) | $k_d$ (1/s) | $K_D$ (M) | t½ (min) | $k_a$ (1/Ms) | $k_d$ (1/s) | $K_D$ (M) | t½ (min) |
| H4H2291S | 4.18E+05 | 1.64E−04 | 3.93E−10 | 70 | 5.58E+05 | 3.23E−04 | 5.80E−10 | 36 |
| H4H2292S | 1.08E+05 | 5.19E−05 | 4.83E−10 | 223 | 1.28E+05 | 2.49E−04 | 1.94E−09 | 46 |
| H4H2293P | 5.81E+05 | 1.27E−04 | 2.19E−10 | 91 | 7.81E+05 | 2.44E−04 | 3.13E−10 | 47 |
| H4H2294S | 5.63E+05 | 7.99E−05 | 1.42E−10 | 145 | 7.73E+05 | 2.61E−04 | 3.38E−10 | 44 |
| H4H2295S | 4.75E+05 | 2.56E−04 | 5.40E−10 | 45 | 6.69E+05 | 1.19E−03 | 1.77E−09 | 10 |
| H4H2296S | 5.63E+05 | 1.87E−04 | 3.32E−10 | 62 | 7.65E+05 | 6.14E−04 | 8.02E−10 | 19 |
| H4H2341S | 1.59E+05 | 2.67E−04 | 1.68E−09 | 43 | 2.48E+05 | 7.37E−04 | 2.98E−09 | 16 |
| H4H2342P | 1.86E+05 | 2.04E−04 | 1.10E−09 | 57 | 3.30E+05 | 6.71E−04 | 2.03E−09 | 17 |
| H4H2344S | 1.83E+05 | 2.40E−04 | 1.31E−09 | 48 | 2.80E+05 | 7.24E−04 | 2.58E−09 | 16 |
| H4H2345S | 1.09E+05 | 3.23E−03 | 2.97E−08 | 4 | 1.84E+05 | 8.70E−03 | 4.73E−08 | 1 |
| H4H2346S | 1.86E+05 | 7.99E−05 | 4.30E−10 | 145 | 4.19E+05 | 5.89E−04 | 1.41E−09 | 20 |
| H4H2350P | 1.03E+05 | 2.07E−04 | 2.01E−09 | 56 | 1.34E+05 | 1.28E−03 | 9.61E−09 | 9 |
| H4H2352S | 7.09E+05 | 5.81E−05 | 8.20E−11 | 199 | 1.18E+06 | 1.39E−04 | 1.18E−10 | 83 |
| H4H2354S | 2.00E+05 | 1.10E−04 | 5.48E−10 | 105 | 2.81E+05 | 6.49E−04 | 2.31E−09 | 18 |
| H4H2355S | 1.86E+05 | 1.52E−04 | 8.21E−10 | 76 | 2.81E+05 | 1.23E−03 | 4.37E−09 | 9 |
| H4H2357S | 2.30E+05 | 5.57E−04 | 2.42E−09 | 21 | 2.95E+05 | 2.10E−03 | 7.12E−09 | 6 |
| H4H2364S | 3.53E+05 | 3.67E−05 | 1.04E−10 | 315 | 3.38E+05 | 2.73E−04 | 8.09E−10 | 42 |
| H1M2207N | 5.61E+04 | 9.00E−04 | 1.60E−08 | 13 | 1.33E+05 | 1.44E−03 | 1.08E−08 | 8 |
| H2aM2210N | 6.73E+04 | 8.63E−04 | 1.28E−08 | 13 | 2.12E+05 | 3.35E−03 | 1.58E−08 | 3 |
| H1M2212N | 8.00E+05 | 1.58E−04 | 1.97E−10 | 73 | 1.02E+06 | 3.03E−04 | 2.97E−10 | 38 |
| H2aM2234N | 6.57E+04 | 7.11E−04 | 1.08E−09 | 16 | 7.93E+05 | 2.72E−03 | 3.43E−09 | 4 |
| H1M2236N | 7.60E+05 | 2.08E−04 | 2.75E−10 | 56 | 1.03E+06 | 5.50E−04 | 5.32E−10 | 21 |
| H4H2236N3 | 9.22E+05 | 2.33E−04 | 2.53E−10 | 50 | 1.96E+06 | 7.48E−04 | 3.82E−10 | 15 |
| H4H2243N2 | 2.67E+05 | 7.80E−04 | 2.92E−09 | 15 | 4.69E+05 | 2.44E−03 | 5.20E−09 | 5 |
| H1M2243N | 1.28E+05 | 2.61E−04 | 2.04E−09 | 44 | 1.37E+05 | 5.95E−04 | 4.35E−09 | 19 |

TABLE 4

Kinetics of MfGFRα3-mmH binding to different anti-GFRα3 antibodies at 25° C. and at 37° C.

| | 25° C. | | | | 37° C. | | | |
|---|---|---|---|---|---|---|---|---|
| AbPID | $k_a$ (1/Ms) | $k_d$ (1/s) | $K_D$ (M) | t½ (min) | $k_a$ (1/Ms) | $k_d$ (1/s) | $K_D$ (M) | t½ (min) |
| H4H2291S | 1.51E+05 | 2.79E−04 | 1.85E−09 | 41 | 3.57E+05 | 6.93E−04 | 1.94E−09 | 17 |
| H4H2292S | 7.76E+04 | 1.22E−04 | 1.57E−09 | 95 | 8.95E+04 | 1.95E−04 | 2.18E−09 | 59 |
| H4H2293P | 2.90E+05 | 4.17E−05 | 1.44E−10 | 277 | 4.41E+05 | 1.58E−04 | 3.58E−10 | 73 |
| H4H2294S | 3.25E+05 | 2.04E−04 | 6.27E−10 | 57 | 4.33E+05 | 9.74E−04 | 2.25E−09 | 12 |
| H4H2295S | 1.83E+05 | 9.73E−04 | 5.32E−09 | 12 | 2.76E+05 | 5.61E−03 | 2.04E−08 | 2 |
| H4H2296S | 1.93E+05 | 6.51E−04 | 3.37E−09 | 18 | 2.77E+05 | 2.85E−03 | 1.03E−08 | 4 |
| H4H2341S | 9.38E+04 | 1.30E−04 | 1.39E−09 | 89 | 1.44E+05 | 5.08E−04 | 3.53E−09 | 23 |
| H4H2342P | 9.37E+04 | 5.50E−04 | 5.87E−09 | 21 | 1.50E+05 | 1.66E−03 | 1.11E−08 | 7 |
| H4H2344S | 1.04E+05 | 1.15E−04 | 1.10E−09 | 101 | 1.61E+05 | 5.75E−04 | 3.57E−09 | 20 |
| H4H2345S | 9.75E+04 | 2.79E−03 | 2.87E−08 | 4 | 1.34E+05 | 3.53E−03 | 2.63E−08 | 3 |
| H4H2346S | 1.08E+05 | 5.98E−05 | 5.56E−10 | 193 | 1.53E+05 | 5.11E−04 | 3.34E−09 | 23 |
| H4H2350P | 6.47E+04 | 1.11E−04 | 1.71E−09 | 104 | 7.48E+04 | 8.96E−04 | 1.20E−08 | 13 |
| H4H2352S | 3.45E+05 | 1.00E−06 | 2.90E−12 | 11550 | 5.57E+05 | 6.53E−05 | 1.17E−10 | 177 |
| H4H2354S | 1.09E+05 | 6.23E−05 | 5.74E−10 | 185 | 1.57E+05 | 4.35E−04 | 2.78E−09 | 27 |
| H4H2355S | 1.05E+05 | 6.78E−05 | 6.49E−10 | 170 | 1.73E+05 | 9.13E−04 | 5.29E−09 | 13 |
| H4H2357S | 1.40E+05 | 3.15E−04 | 2.26E−09 | 37 | 1.72E+05 | 1.35E−03 | 7.86E−09 | 9 |
| H4H2364S | 1.22E+05 | 1.30E−04 | 1.06E−09 | 89 | 1.68E+05 | 8.61E−04 | 5.14E−09 | 13 |
| H1M2207N | 3.99E+04 | 3.88E−03 | 9.72E−08 | 3 | 4.58E+04 | 6.63E−03 | 1.45E−07 | 2 |
| H2aM2210N | 4.16E+04 | 1.20E−03 | 2.89E−08 | 10 | 8.09E+04 | 6.18E−03 | 7.64E−08 | 2 |
| H1M2212N | 3.84E+05 | 1.12E−04 | 2.93E−10 | 103 | 8.84E+05 | 2.60E−04 | 2.94E−10 | 44 |
| H2aM2234N | 4.27E+05 | 5.71E−04 | 1.34E−09 | 20 | 4.29E+05 | 2.11E−03 | 4.91E−09 | 5 |
| H1M2236N | 2.96E+05 | 2.86E−04 | 9.70E−10 | 40 | 4.34E+05 | 1.12E−03 | 2.58E−09 | 10 |
| H1M2243N | 6.46E+04 | 6.58E−04 | 1.02E−08 | 18 | 5.02E+04 | 2.75E−03 | 5.47E−08 | 4 |

TABLE 5

Kinetics of hGFRα3-hFc or hGFRα3-mFc binding to different anti-GFRα3 antibodies at 25° C. and at 37° C.

| | 25° C. | | | | 37° C. | | | |
|---|---|---|---|---|---|---|---|---|
| AbPID | $k_a$ (1/Ms) | $k_d$ (1/s) | $K_D$ (M) | t½ (min) | $k_a$ (1/Ms) | $k_d$ (1/s) | $K_D$ (M) | t½ (min) |
| H4H2291S | 1.03E+06 | 4.78E−06 | 4.63E−12 | 2417 | 1.33E+06 | 3.84E−05 | 2.89E−11 | 301 |
| H4H2292S | 5.34E+05 | 1.00E−06 | 1.87E−12 | 11550 | 5.96E+05 | 2.57E−05 | 4.32E−11 | 449 |
| H4H2293P | 1.22E+06 | 1.93E−06 | 1.59E−12 | 5988 | 1.71E+06 | 5.13E−05 | 2.99E−11 | 225 |
| H4H2294S | 1.22E+06 | 5.63E−06 | 4.63E−12 | 2052 | 1.66E+06 | 3.46E−05 | 2.09E−11 | 334 |
| H4H2295S | 1.08E+06 | 1.69E−06 | 1.57E−12 | 6822 | 1.62E+06 | 4.88E−05 | 3.01E−11 | 237 |
| H4H2296S | 1.24E+06 | 4.17E−06 | 3.37E−12 | 2770 | 1.61E+06 | 4.74E−05 | 2.94E−11 | 244 |
| H4H2341S | 5.96E+05 | 1.00E−06 | 1.68E−12 | 11550 | 9.61E+05 | 7.58E−05 | 7.89E−11 | 152 |
| H4H2342P | 6.61E+05 | 1.00E−06 | 1.51E−12 | 11550 | 1.21E+06 | 4.28E−05 | 3.54E−11 | 270 |
| H4H2344S | 5.79E+05 | 1.56E−06 | 2.69E−12 | 7409 | 1.41E+06 | 8.96E−05 | 8.91E−11 | 129 |
| H4H2345S | 5.16E+05 | 3.01E−05 | 5.84E−11 | 384 | 7.00E+05 | 7.44E−05 | 1.06E−10 | 155 |
| H4H2346S | 6.47E+05 | 1.44E−05 | 2.22E−11 | 803 | 1.75E+06 | 1.37E−04 | 7.81E−11 | 84 |
| H4H2350P | 5.09E+05 | 2.12E−05 | 4.16E−11 | 545 | 2.56E+06 | 1.26E−04 | 4.92E−11 | 92 |
| H4H2352S | 2.14E+06 | 1.00E−06 | 4.67E−13 | 11550 | 2.28E+06 | 3.00E−05 | 1.32E−11 | 385 |
| H4H2354S | 5.80E+05 | 1.09E−05 | 1.89E−11 | 1056 | 1.02E+06 | 9.11E−05 | 8.95E−11 | 127 |
| H4H2355S | 6.11E+05 | 1.00E−06 | 1.64E−12 | 11550 | 1.10E+06 | 3.39E−05 | 3.10E−11 | 341 |
| H4H2357S | 7.79E+05 | 2.52E−05 | 3.24E−11 | 458 | 1.19E+06 | 9.40E−05 | 7.93E−11 | 123 |
| H4H2364S | 7.71E+05 | 1.00E−06 | 1.30E−12 | 11550 | 1.26E+06 | 4.14E−05 | 3.28E−11 | 279 |
| H1M2207N* | 1.59E+05 | 2.60E−05 | 1.63E−10 | 444 | 2.03E+05 | 1.08E−04 | 5.31E−10 | 107 |
| H2aM2210N* | 1.68E+05 | 3.69E−05 | 2.20E−10 | 313 | 3.16E+05 | 7.66E−05 | 2.42E−10 | 151 |
| H1M2212N* | 1.12E+06 | 1.44E−05 | 1.28E−11 | 800 | 1.49E+06 | 6.17E−05 | 4.13E−11 | 187 |
| H2aM2234N* | 9.50E+05 | 9.60E−05 | 1.01E−10 | 120 | 1.26E+06 | 1.46E−04 | 1.16E−10 | 79 |
| H1M2236N* | 1.28E+06 | 1.76E−05 | 1.37E−11 | 658 | 1.58E+06 | 9.65E−05 | 6.10E−11 | 120 |
| H1M2243N* | 1.34E+05 | 1.00E−06 | 7.50E−12 | 11550 | 1.86E+05 | 2.18E−05 | 1.17E−10 | 529 |

*Tested for binding to hGFRα3-hFc, all other antibodies tested for binding to hGFRα3-mFc Example 4

Blocking of Human GFRα3 Binding to Human ARTEMIN by Anti-GFRα3 Antibodies

The ability of anti-GFRα3 antibodies to block human GFRα3 binding to human ARTEMIN in the presence or absence of co-receptor human RET was determined using two different blocking ELISA formats.

In the first format, recombinant human ARTEMIN protein with a C-terminal myc-myc-hexahistidine tag (hARTEMIN-mmH; SEQ ID:369) was coated at 2 ug/ml in 96-well microtiter plates in PBS buffer overnight at 4° C. and then blocked with a solution of 0.5% (w/v) BSA. A constant amount of human GFRα3 fused with a C-terminal human Fc tag (hGFRα3-hFc; SEQ ID:371) at 120 pM was pre-mixed with varying amounts of antibodies, ranging from 0 to ~10 nM in serial dilutions, followed by an 1 hour incubation at room temperature (RT) to allow antibody-hGFRα3-hFc binding to reach equilibrium. The equilibrated sample solutions were then transferred to the hARTEMIN-mmH-coated plate. After 1 hour of binding, the plate was washed, then the bound hGFRα3-hFc was detected using HRP-conjugated anti-human IgG Fc specific antibody (Jackson Immunochemical, #109-035-098), and colorimetric signals were developed using a TMB HRP substrate (BD Biosciences, #51-2606KC and #51-2607KC). Absorbance was recorded at 450 nm on a Victor X5 plate reader (Perkin Elmer) to determine the amount of free hGFRα3-hFc in the pre-equilibrated hGFRα3-hFc-antibody solutions that was able to bind to the plate coated with hARTEMIN-mmH. $IC_{50}$ values, defined as the concentration of antibody required to reduce the signal from a constant concentration of hGFRα3-hFc by 50%, were calculated from the data using Prism software from GraphPad. The absorbance measured at the constant amount of 120 pM hGFRα3-hFc in the absence of anti-GFRα3 antibody is defined as 0% blocking and the absorbance with no added hGFRα3-hFc is defined as 100% blocking. The observed absorbance in the wells containing the highest antibody concentration was used to calculate the maximum blocking percent shown in the table. The results are summarized in Table 6.

In the second ELISA format, the plates, samples and data were processed similarly as for the first format except both hARTEMIN-mmH and human RET with a C-terminal 10 histidine tag (hRET-10His; R&D Systems, #1168-CR/CF) were coated for the blocking ELISA experiment. The 96-well microtiter plates were coated with a mixture of 1.2 ug/ml hARTEMIN-mmH and 6.9 ug/ml hRET-10His proteins in PBS overnight at 4° C. and then blocked with a solution of 0.5% (w/v) BSA. A constant amount of biotinylated human GFRα3 with a C-terminal myc-myc-hexahistidine tag (biotin-hGFRα3-mmH; SEQ ID:370) at 1 nM was pre-mixed with varied amounts of anti-GFRα3 antibodies, ranging from 0 to ~100 nM in serial dilutions, followed by a 1 hour incubation at RT to allow antibody-biotin-hGFRα3-mmH binding to reach equilibrium. The equilibrated samples were then transferred to the coated plate. After 1 hour of binding, the plate was washed, then the bound biotin-hGFRα3-mmH was detected using HRP conjugated streptavidin (Pierce, #N200), and colorimetric signals were developed using TMB HRP substrates. $IC_{50}$ values and the maximal blocking by each antibody are shown in the Table 6.

As shown in Table 6, 9 of the 23 anti-GFRα3 antibodies blocked 51-94% of the hGFRα3-hFc binding to coated hARTEMIN-mmH with $IC_{50}$ values ranging from 43.8 pM to 723 pM in the first ELISA format. Eight of the 23 anti-GFRα3 antibodies caused the hGFRα3-hFc binding signal to increase ("enhancer" in Table 6) at many of the higher tested antibody concentrations in the first ELISA format. Six of the 23 antibodies tested in the first ELISA format did not block or enhance the hGFRα3-hFc binding signal to coated hARTEMIN-mmH. As shown in Table 6, for the second ELISA format, 17 of the 23 anti-GFRα3 antibodies blocked 75-100% of the biotin-hGFRα3-mmH binding to dual-coated hARTEMIN-mmH and hRET-10His with $IC_{50}$ values ranging from 403 pM to 14.6 nM. Also in the second ELISA format, five of the 23 anti-GFRα3 antibodies caused the biotin-hGFRα3-mmH binding signal to increase at lower antibody concentrations but blocked 28-95% of the biotin-hGFRα3-mmH binding to hARTEMIN-mmH and hRET-10His at antibody concentrations 1 nM and above ("enhancer" in Table 6). One anti-GFRα3 antibody caused the biotin-hGFRα3-mmH binding signal to increase ("enhancer" in Table 6) at the higher tested antibody concentrations, with no blocking at any concentration, in the second ELISA format.

TABLE 6

ELISA Blocking of human GFRα3 to human ARTEMIN alone or human ARTEMIN and human RET

| | ELISA format 1: Ab blocking 120 pM hGFRα3-hFc binding to coated hARTEMIN-mmH | | ELISA format 2: Ab blocking 1 nM biotin-hGFRα3-mmH binding to coated hARTEMIN-mmH and hRET-10His | |
|---|---|---|---|---|
| AbPID | $IC_{50}$ (M) | % max blocking | $IC_{50}$ (M) | % max blocking |
| H4H2207N | enhancer | NB | 7.30E−09 | 85 |
| H4H2210N | enhancer | NB | enhancer | NB |
| H4H2212N | 4.38E−11 | 81 | 4.03E−10 | 99 |
| H4H2234N | 8.29E−11 | 70 | 3.42E−09 | 97 |
| H4H2236N3 | enhancer | NB | enhancer | 68 |
| H4H2243N2 | enhancer | NB | 1.12E−09 | 95 |
| H4H2291S | NB | NB | enhancer | 28 |
| H4H2292S | 7.23E−10 | 89 | 1.76E−09 | 100 |
| H4H2293P | 2.60E−10 | 93 | 7.38E−09 | 95 |
| H4H2294S | NB | NB | 9.52E−10 | 95 |
| H4H2295S | enhancer | NB | enhancer | 44 |
| H4H2296S | NB | NB | enhancer | 91 |
| H4H2341S | enhancer | NB | 1.62E−09 | 98 |
| H4H2342P | enhancer | NB | 1.08E−09 | 97 |
| H4H2344S | 1.33E−10 | 94 | 4.59E−10 | 100 |
| H4H2345S | enhancer | NB | 1.46E−08 | 75 |
| H4H2346S | 9.78E−11 | 92 | 7.971E−10 | 99 |
| H4H2350P | 4.96E−10 | 93 | 1.29E−09 | 91 |
| H4H2352S | 6.58E−11 | 51 | 7.61E−10 | 100 |
| H4H2354S | 1.16E−10 | 92 | 1.32E−09 | 97 |
| H4H2355S | NB | NB | enhancer | 95 |
| H4H2357S | NB | NB | 3.28E−09 | 86 |
| H4H2364S | NB | NB | 1.45E−09 | 100 |

NB = non-blocker

Example 5

Measuring the Ability of Anti-GFRα3 Antibodies to Block Activation of GFRα3 and RET by the Ligand ARTEMIN In Vitro The ability of anti-GFRα3 antibodies to block activation of GFRα3 and RET by its ligand ARTEMIN in vitro was determined using a cell-based assay. HEK293 cells modified to stably express both human GFRα3 (amino acids 1-400 of accession number NP_001487.2) and human RET (amino acids 1-1072 of accession number NP_065681) were generated and then transduced with a SRE responsive luciferase reporter (SRE-luc; Sabiosciences, CCS-010L) (HEK293/hGFRα3/hRET cells).

Twenty thousand HEK293/hGFRα3/hRET/SRE-luc cells were seeded into Poly D-Lysine coated 96 well plates (Greiner, #35-4620) in Optimem (GIBCO, #31985) containing 0.5% FBS and then grown overnight in 5% $CO_2$ at 37° C. The cells were then incubated for 1 hour at room temperature with serial dilutions of anti-GFRα3 antibodies ranging from 5 pM to 300 nM. A constant dose (100 pM) of human ARTEMIN expressed with a C-terminal myc myc hexahistidine tag (SEQ ID:369) was then added to the cells and incubated for an additional 6 hours. Luciferase activity was measured as relative light units (RLU) on a Victor luminometer (Perkin Elmer) after the addition of OneGlo reagent (Promega, #E6051). $EC_{50}$ and $IC_{50}$ values were calculated from a four-parameter logistic equation over a 12-point response curve using Graph Pad Prism data analysis software.

Twenty-three anti-GFRα3 antibodies were tested for their ability to inhibit ARTEMIN-dependent activation of the HEK293/hGFRα3/hRET/SRE-luc cells. As shown in Table 7, all 23 antibodies tested blocked luciferase activity with $IC_{50}$ values ranging from 0.2 nM to 48.3 nM, and 19 of 23 antibodies blocked to the baseline at a concentration of 300 nM. Four of the 23 antibodies (H4H2344S, H4H2345S, H4H2346S, and H4H2354S-1) did not block to baseline at any of the antibody concentrations tested.

TABLE 7

Inhibition of ARTEMIN-dependent stimulation of HEK293/hGFRα3/hRET/SRE-luc cells by anti-GFRα3 antibodies

| AbPID | $IC_{50}$ (nM) |
|---|---|
| H4H2294S | 0.27 |
| H4H2342P | 1.0 |
| H4H2212N | 0.80 |
| H4H2292S | 4.6 |
| H4H2243N2 | 0.30 |
| H4H2352S | 0.92 |
| H4H2207N | 2.4 |
| H4H2210N | 2.9 |
| H4H2234N | 2.3 |
| H4H2236N3 | 1.5 |
| H4H2291S | 1.3 |
| H4H2293P | 20 |
| H4H2294S | 1.7 |
| H4H2295S | 1.5 |
| H4H2296S | 1.4 |
| H4H2341S | 7.1 |
| H4H2344S | 48 |
| H4H2345S | 26 |
| H4H2346S | 26 |
| H4H2354S | 22 |
| H4H2355S | 2.3 |
| H4H2357S | 4.9 |
| H4H2364S | 2.3 |

Example 6

Inhibition of ARTEMIN-Sensitized Capsaicin Thermal Hyperalgesia

To induce ARTEMIN-sensitized thermal hyperalgesia in mice, each mouse was pre-treated with an intra-plantar injection of 0.5 micrograms mouse recombinant ARTEMIN (R&D Systems, #1085-AR) 24 hours before administering an intra-plantar injection of 0.5 micrograms capsaicin (a sub-optimal dose) from a 100 mM solution in DMSO (Sigma-Aldrich, #M-2028). Thermal hyperalgesia was evaluated using the Hargreaves' Test, in which a beam of light is directed at the injected paw until the animal withdraws its paw. The latency to withdraw is recorded as a behavioral measure of nociception. Thermal hyperalgesia is consistently ARTEMIN-sensitized at 3 days after capsaicin administration based on significantly decreased paw withdrawal latencies. For these studies, a baseline value for withdrawal latency was measured before dosing with either ARTEMIN or capsaicin followed by a second measurement three days after capsaicin treatment. The experimenter conducting these assays was blind to the treatment group of the animals.

For all experiments evaluating the efficacy of human anti-GFRα3 antibodies in ARTEMIN-sensitized hyperalgesia, adult mice homozygous for the expression of human GFRα3 in place of mouse GFRα3 ("humanized GFRα3") were used. Both male and female mice were used in each assay, with sex balanced across treatment groups (a total of 8 mice per treatment or control group). Humanized GFRα3 mice were previously determined to have ARTEMIN-induced capsaicin thermal hyperalgesia latency responses similar to those observed in wild-type mice.

Six anti-GFRα3 antibodies (H4H2212N, H4H2243N2, H4H2292S, H4H2294S, H4H2342P, and H4H2352S-1) were tested in the model. All antibodies were diluted in phosphate-buffered saline (PBS) and were administered subcutaneously at 25 mg/kg in a 1 ml/100 g body weight volume 24 hours prior to ARTEMIN injection into the hindpaw. In each experiment, one group of animals received an isotype control antibody.

Pain sensitivity for each treatment or control group was defined as percentage of baseline withdrawal latency (% BWL), calculated as the fractional change for each animal's time-based withdrawal latency (WL) three days after capsaicin treatment compared to their baseline withdrawal latency without capsaicin treatment:

$$\% \text{ BWL} = [(WL_{(capsaicin)} - WL_{(no\ capsaicin)}) / WL_{(no\ capsaicin)}] \times 100$$

Using % BWL, larger negative values indicate greater thermal hyperalgesia.

Table 8 shows the summary of group means (in boldface type) and standard error of the means (in italics) for percentage of baseline withdrawal latency (% BWL) in the ARTEMIN-sensitized capsaicin thermal hyperalgesia model assessed at three days after capsaicin injection.

As shown in Table 8, mice treated with anti-hGFRα3 antibodies exhibited increases in % BWL (smaller negative or positive values) compared to mice treated with the isotype control antibody. Four antibodies, H4H2352S, H4H2243N2, H4H2294S, and H4H2342P promoted the greatest resistance to thermal hyperalgesia across all experiments performed.

TABLE 8

Data Summary in the ARTEMIN-sensitized capsaicin thermal hyperalgesia model assessed at three days after capsaicin injection.

| | % BWL | | | |
|---|---|---|---|---|
| AbPID | Exp. 323 | Exp. 361 | Exp. 367 | Exp. 380 |
| Isotype control | −17 ± 7.6 | −32 ± 6.8 | −40 ± 4.8 | −35 ± 3.5 |
| H4H2292S | 0.72 ± 19 | nd | nd | −26 ± 5.9 |
| H4H2352S | 27 ± 15 | nd | −5.6 ± 9.4** | nd |
| H4H2243N2 | 20 ± 18 | nd | nd | 21 ± 6.4*** |
| H4H2294S | nd | −9.0 ± 12 | 2.3 ± 12** | nd |
| H4H2342P | nd | −12 ± 9.3 | 18 ± 8.3*** | nd |
| H4H2212N | nd | −22 ± 6.9 | nd | nd | significantly different than isotype control, p < .01; *p < .001
(nd = not tested in this experiment)

Example 7

Testing of Anti-GFRα3 Antibodies for Cross-Reactivity with GFRα1 and GFRα2

The ability of anti-GFRα3 antibodies to bind to GDNF-family receptors was assessed using an Octet Red biosensor (Fortebio, Inc.). Antibodies were tested for binding to either human GFRα1 expressed with a C-terminal human Fc tag and a hexahistidine tag (hGFRα1-hFc-6His, R&D Systems #714-GR), human GFRα1 expressed with only a C-terminal human Fc tag (hGFRα1-hFc; SEQ ID: 376), human GFRα2 expressed with a C-terminal human Fc tag and a hexahistidine tag (hGFRα2-hFc-6His, R&D Systems #613-FR), human GFRα3 expressed with a C-terminal human Fc tag (hGFRα3-hFc, SEQ ID:371), or an irrelevant human Fc tagged protein. Antigens were captured onto anti-human Fc sensor tips from 10 ug/mL solutions for 5 minutes. The coated sensor tips were then blocked with a 100 ug/mL solution of irrelevant human Fc antibodies for 5 minutes. Blocked sensor tips were then submerged into wells containing 667 uM of each anti-GFRα3 antibody or buffer alone for 10 minutes. The experiment was performed at 25° C. with a flow rate of 1000 rpm using HBST+BSA buffer (10 mM HEPES, 150 mM NaCl, 3 mM EDTA, 0.05% w/v Surfactant P20, 0.1 mg/mL BSA, pH 7.4). The binding response (measured in units of nm) at each step of the experiment was monitored and recorded.

All six of the tested anti-GFRα3 antibodies showed binding above 1.0 nm to the hGFRα3-hFc protein, but did not demonstrate any measurable binding to the other GDNF-family receptors or to the irrelevant human Fc tagged protein, as shown in Table 9.

with serial dilutions of anti-GFRα3 antibodies ranging from 5 pM to 300 nM. A constant dose (500 pM) of human ARTEMIN expressed with a C-terminal myc-myc-hexahistidine tag (Human ARTEMIN-MMH; SEQ ID: 369) was then added to the cells and incubated for an additional 6 hours. To determine the $EC_{50}$ value of human ARTEMIN-MMH from dose response curves, serial dilutions of human ARTEMIN-MMH ranging from 0.5 pM to 10 nM was added to the cells without antibodies and incubated for 6 hours at 37° C. Luciferase activity was measured as relative light units (RLU) on a Victor luminometer (Perkin Elmer) after the addition of OneGlo reagent (Promega, #E6051). $EC_{50}$ and $IC_{50}$ values were calculated from a four-parameter logistic equation over a 12-point response curve using GraphPad Prism data analysis software.

Six anti-GFRα3 antibodies were tested for their ability to inhibit ARTEMIN-dependent activation of the HEK293/MfGFRα3/MfRET/SRE-luc cells. As shown in Table 10, all six antibodies tested completely blocked luciferase activity with $IC_{50}$ values ranging from 0.7 nM to 2.5 nM. Human ARTEMIN-MMH stimulated SRE-dependent luciferase activity in the HEK293/mfGFRα3/mfRet/SRE-LUC cell line with an $EC_{50}$ value of 70 pM.

TABLE 9

Reactivity of Anti-GFRα3 Antibodies with GFRα1, GFRα2 and GFRα3

| Antigen | Capture Level (nm) +/− Std dev | 100 ug/mL H4H2294S Bound (nm) | 100 ug/mL H4H2342P Bound (nm) | 100 ug/mL H4H2243N2 Bound (nm) | 100 ug/mL H4H2212N Bound (nm) | 100 ug/mL H4H2352S Bound (nm) | 100 ug/mL H4H2292S Bound (nm) | Buffer |
|---|---|---|---|---|---|---|---|---|
| hGFRα1-hFc | 1.89 ± 0.14 | 0.04 | 0.06 | 0.03 | 0.00 | 0.02 | 0.05 | −0.07 |
| hGFRα1-hFc-6his | 1.66 ± 0.10 | 0.03 | 0.08 | 0.03 | −0.01 | 0.03 | 0.03 | −0.07 |
| hGFRα2-hFc-6his | 1.49 ± 0.09 | 0.06 | 0.12 | 0.06 | 0.02 | 0.04 | 0.05 | −0.06 |
| hGFRα3-hFc | 1.68 ± 0.10 | 1.17 | 1.59 | 1.11 | 1.18 | 1.25 | 1.04 | −0.09 |
| Irrelevant hFc tagged protein | 1.00 ± 0.06 | 0.03 | 0.07 | 0.03 | 0.00 | 0.03 | 0.02 | −0.08 |

Example 8

Measuring the Ability of Anti-GFRα3 Antibodies to Block ARTEMIN Stimulation in a HEK293/MfGFRα3/MfRet/SRE-Luc Bioassay The ability of anti-GFRα3 antibodies to block activation of cynomolgus GFRα3 and cynomolgus RET by its ligand ARTEMIN in vitro was determined using a cell-based assay. HEK293 cells modified to stably express both cynomolgus GFRα3 (MfGFRα3; SEQ ID: 377) and cynomolgus RET (MfRET; SEQ ID: 378) were generated and then transduced with a Cignal Lenti SRE Reporter (SA Biosciences, #CLS-010L) expressing the firefly luciferase gene under the control of a minimal CMV promoter and tandem repeats of the serum response element to generate the HEK293/MfGFRα3/MfRet/SRE-Luc cell line.

For the bioassay, 20,000 HEK293/MfGFRα3/MfRet/SRE-Luc cells were seeded onto Poly D-Lysine coated 96 well plates (Greiner, #35-4620) in Optimem (GIBCO, #31985) containing 0.5% FBS and then grown overnight at 5% $CO_2$ at 37° C. The cells were then incubated for 1 hour

TABLE 10

Inhibition of ARTEMIN-dependent stimulation of HEK293/MfGFRα3/MfRET/SRE-luc cells by anti-GFRα3 antibodies

| Antibody | $IC_{50}$ (nM) |
|---|---|
| H4H2294S | 0.7 |
| H4H2342P | 2.5 |
| H4H2212N | 1.8 |
| H4H2292S | 1.5 |
| H4H2243N2 | 0.8 |
| H4H2352S | 1.3 |

Example 9

Generation of a Bi-Specific Anti-GFRα3 Antibody

Various bi-specific antibodies are generated for use in practicing the methods of the invention. For example, GFRα3-specific antibodies are generated in a bi-specific format (a "bi-specific") in which variable regions binding to distinct epitopes on GFRα3 are linked together to confer dual-epitope specificity within a single binding molecule. Appropriately designed bi-specifics may enhance overall GFRα3 blocking efficacy through increasing both GFRα3 specificity and binding avidity. Variable regions with specificity for individual different epitopes within any of the three cysteine repeats or that can bind to different regions within one epitope of any of the three cysteine repeats are paired on a structural scaffold that allows each variable region to bind simultaneously to the separate epitopes, or to different regions within one epitope. In one example for a bi-specific, heavy chain variable regions ($V_H$) from a binder with specificity for one epitope within one cysteine repeat are recombined with light chain variable regions ($V_L$) from a series of binders having specificity for a second epitope within any of the other two cysteine repeats to identify non-cognate $V_L$ partners that can be paired with an original $V_H$ without disrupting the original specificity for that $V_H$. In this way, a single $V_L$ segment (e.g., $V_L1$) can be combined with two different $V_H$ domains (e.g., $V_H1$ and $V_H2$) to generate a bi-specific comprised of two binding "arms" ($V_H1$-$V_L1$ and $V_H2$-$V_L1$). Use of a single $V_L$ segment reduces the complexity of the system and thereby simplifies and increases efficiency in cloning, expression, and purification processes used to generate the bi-specific (See, for example, U.S. Ser. No. 13/022,759 and US2010/0331527).

Alternatively, antibodies that bind both GFRα3 and a second target, such as, but not limited to, for example, RET may be prepared in a bi-specific format using techniques described herein, or other techniques known to those skilled in the art. Antibody variable regions binding to distinct GFRα3 regions that are extracellularly exposed are linked together with variable regions that bind to relevant sites on, for example, the ligand, artemin, other GFRα receptors, or to RET, to confer dual-antigen specificity within a single binding molecule. Variable regions with specificity for individual epitopes of GFRα3, are combined with a variable region with specificity for, for example, artemin and are paired on a structural scaffold that allows each variable region to bind to the separate antigens.

The bi-specific binders are tested for binding and functional blocking of the target antigens, for example, GFRα3 and/or artemin, other GFRα receptors, or RET, in any of the assays described above for antibodies. For example, standard methods to measure soluble protein binding are used to assess the bispecific interaction with its antigen(s), such as Biacore, ELISA, size exclusion chromatography, multi-angle laser light scattering, direct scanning calorimetry, and other methods. Binding of bi-specific antibodies to cells expressing GFRα3 is determined through flow cytometry using a fluorescently labeled secondary antibody recognizing the target antigen on the cells. Binding experiments with peptides can also be conducted using surface plasmon resonance experiments, in which real-time binding interaction of peptide to antibody is measured by flowing a peptide or bi-specific across a sensor surface on which bi-specific or peptide, respectively, is captured. Functional in vitro blocking of the GFRα3 receptor by a bi-specific is determined using any bioassay such as that described herein, or by in vivo determination of reaction to pain in appropriate animal models, such as those described herein. Functional in vitro blocking of GFRα3 or its ligand, artemin, by a bi-specific is determined using any bioassay such as that described in WO2010/077854, or in US2010/0166768, or by in vivo determination of hypersensitivity to thermal stimuli in appropriate animal models, such as those described herein.

Example 10

Surface Plasmon Resonance Derived Binding Affinities and Kinetic Constants of Monoclonal Anti-Mouse GFRα3 Antibodies Binding associative and dissociative rate constants ($k_a$ and $k_d$, respectively) and calculated equilibrium dissociation constants and dissociative half-lives ($K_D$ and $t_{1/2}$, respectively) for antigen binding to anti-mouse GFRα3 antibodies were determined using a real-time surface plasmon resonance biosensor (Biacore 3000) assay at 25° C. Antibodies were tested for binding to mouse GFRα3 expressed with myc-myc-hexahistidine tag (mGFRα3-MMH; SEQ ID: 379,). Anti-mouse GFRα3 antibodies were captured on a goat anti-mouse IgG polyclonal antibody (GE Healthcare, # BR-1008-38) surface created through direct amine coupling to a Biacore CM5 sensor chip. Kinetic experiments were carried out using HBS-EP (10 mM HEPES, 150 mM NaCl, 3 mM EDTA, 0.05% Surfactant P20, at pH 7.4) as both the running buffer and the sample buffer. Binding to mouse GFRα3-MMH was evaluated by injecting several concentrations ranging from 100 nM to 6.25 nM (2-fold dilutions) across the captured antibody surface. Antibody-antigen association was monitored for up to 5 minutes, while dissociation in buffer was monitored for up to 10 minutes. Kinetic association ($k_a$) and dissociation ($k_d$) rate constants were determined by processing and fitting the data to a 1:1 binding model using Scrubber 2.0c curve fitting software. Binding dissociation equilibrium constants ($K_D$) and dissociative half-lives ($t_{1/2}$) were calculated from the kinetic rate constants as: $K_D$ (M)=$k_d/k_a$ and $t_{1/2}$ (min)=[ln 2/(60*$k_d$)].

As shown in Table 11, the two anti-mouse GFRα3 antibodies tested, M1M6986N and M1M6977N, bound to mGFRα3-MMH at 25° C. with $K_D$ values of 23.1 pM and 107 pM, respectively.

TABLE 11

Kinetics of mGFRα3-MMH binding to different anti-mouse GFRα3 antibodies at 25° C.

| AbPID | $k_a$ (1/Ms) | $k_d$ (1/s) | $K_D$ (M) | t½ (min) |
|---|---|---|---|---|
| M1M6986N | 1.02E+06 | 2.35E−05 | 2.31E−11 | 491 |
| M1M6977N | 3.84E+05 | 4.1E−05 | 1.07E−10 | 282 |

Example 11

Mouse GFRα3 Blocking ELISA

The ability of anti-mouse GFRα3 antibodies to block mouse GFRα3 binding to mouse ARTEMIN in the presence or absence of co-receptor mouse RET was determined using two different blocking ELISA formats. In the first format, recombinant mouse ARTEMIN (R&D cat#1085-AR/CF) protein was coated at 2 ug/mL (166 nM) in 96-well microtiter plates in PBS buffer overnight at 4° C. and then blocked with a solution of 0.5% (w/v) BSA. A constant amount (3.5 nM) of biotinylated mouse GFRα3 with a C-terminal myc-myc-hexahistidine tag (Biotin-mGFR 3-MMH, SEQ ID:379) was pre-mixed with varying amounts of antibodies, ranging from 100 nM to 1.6 pM in serial dilutions, followed by 1 hour incubation at room temperature (RT) to allow antibody-biotin-mGFRα3-MMH binding to reach equilibrium. The equilibrated sample solutions were then transferred to the mARTEMIN-coated plate. After 1 hour of binding, the plate was washed, then the bound biotin-mGFRα3-MMH was detected using Streptavidin-HRP (Pierce, #N200) and colorimetric signals were developed using a TMB HRP substrate (BD Biosciences, #51-2606KC and #51-2607KC). Absorbance was recorded at 450 nm on a Victor X5 plate reader (Perkin Elmer) to determine the amount of free biotin-mGFRα3-MMH in the pre-equilibrated biotin-mGFRα3-MMH-antibody solutions that was able to bind to the plate-coated mARTEMIN. $IC_{50}$ values, defined as the concentration of antibody required to reduce the signal from a constant concentration of biotin-mGFRα3-MMH by 50%, were calculated from the data using Prism software from GraphPad. The absorbance measured at the constant amount of biotin-mGFRα3-MMH in the absence of anti-mouse GFRα3 antibody is defined as 0% blocking and the absorbance with no added biotin-mGFRα3-MMH is defined as 100% blocking. The observed absorbance in the wells containing the highest antibody concentration was used to calculate the maximum blocking percent shown in the table. The results are summarized in Table 12.

In the second ELISA format, the plates, samples and data were processed similarly as for the first format except both mouse RET expressed with C-terminal hFc and hexahistidine tags (mRET-hFc-6His; R&D cat#482-RT/CF) and mARTEMIN (R&D cat#1085-AR/CF) were coated for the blocking ELISA experiment. The 96-well microtiter plates were coated with a mixture of 1.2 ug/mL (100 nM) mARTEMIN and 9.5 ug/mL (100 nM) mRET-hFc-6His proteins in PBS overnight at 4° C. and then blocked with a solution of 0.5% (w/v) BSA. A constant amount (350 pM) of biotin-mGFRα3-MMH was pre-mixed with varied amounts of anti-mouse GFRα3 antibodies, ranging from 100 nM to 1.6 pM in serial dilutions, followed by a 1 hour incubation at RT to allow antibody-biotin-mGFRα3-MMH binding to reach equilibrium. The equilibrated samples were then transferred to the coated plate. After 1 hour of binding, the plate was washed, then the bound biotin-mGFRα3-MMH was detected using HRP conjugated streptavidin and colorimetric signals were developed using TMB HRP substrates. $IC_{50}$ values and the maximal blocking by each antibody are shown in the Table 12.

As shown in Table 12, only one anti-mouse GFRα3 antibody tested, M1M6986N, demonstrated the ability to block biotin-mGFRα3-MMH from binding to the coated mARTEMIN plate with an $IC_{50}$ value of 69.1 pM. The other anti-mouse GFRα3 antibody tested, M1M6977N, did not demonstrate any measurable blockade in this ELISA format. Both anti-mouse GFRα3 antibodies tested, M1M6986N and M1M6977N, demonstrated the ability to completely block biotin-mGFRα3-MMH from binding to the plates coated with both mARTEMIN and mRET-hFc-6His, with $IC_{50}$ values of 47.2 pM and 366 pM, respectively.

TABLE 12

ELISA Blocking of mouse GFRα3 to mouse ARTEMIN alone or mouse ARTEMIN and mouse RET

| AbPID | ELISA format 1: Antibody blocking 3.5 nM biotin-mGFRα3-MMH binding to coated mARTEMIN | | ELISA format 2: Antibody blocking 350 pM biotin-mGFRα3-MMH binding to coated mARTEMIN and mRET-hFc-6His | |
|---|---|---|---|---|
| | $IC_{50}$ (M) | % max blocking | $IC_{50}$ (M) | % max blocking |
| M1M6986N | 6.91E−11 | 100% | 4.72E−11 | 100% |
| M1M6977N | NB | | 3.66E−10 | 100% |

NB = non-blocker

Example 12

Cell Based Luciferase Bioassay

The ability of anti-mouse GFRα3 antibodies to block activation of mouse GFRα3 and mouse RET by its ligand mouse ARTEMIN in vitro was determined using a cell-based assay. HEK293 cells modified to stably express both mouse GFRα3 (amino acids 1-397 of accession number AAH66202.1) and mouse RET (amino acids 1-1115 of accession number NP_033076.2) were generated and then transduced with a SRE responsive luciferase reporter (SRE-luc; Sabiosciences, CCS-010L) (293/mGFRα3/mRET/SRE-luc cells).

Twenty thousand 293/mGFRα3/mRET/SRE-luc cells were seeded into Poly D-Lysine coated 96 well plates (Greiner, #35-4620) in Optimem (GIBCO, #31985) containing 0.5% FBS and then grown overnight in 5% $CO_2$ at 37° C. The cells were then incubated for 1 hour at room temperature with serial dilutions of anti-mouse GFRα3 antibodies ranging from 3 nM to 44 nM. A constant dose (100 pM) of mouse ARTEMIN (R&D, #1085-AR/CF) was then added to the cells and incubated for an additional 6 hours. Luciferase activity was measured as relative light units (RLU) on a Victor luminometer (Perkin Elmer) after the addition of OneGlo reagent (Promega, #E6051). $EC_{50}$ and $IC_{50}$ values were calculated from a four-parameter logistic equation over a 12-point response curve using GraphPad Prism data analysis software.

As shown in Table 13, both anti-mouse GFRα3 antibodies tested, M1M6986N and M1M6977N demonstrated the ability to inhibit mouse ARTEMIN-dependent stimulation of 293/mGFRα3/mRET/SRE-luc cells with $IC_{50}$ values of approximately 44 nM and 3 nM, respectively.

TABLE 13

Inhibition of ARTEMIN-dependent stimulation of 293/mGFRα3/mRET/SRE-luc cells by anti-mouse GFRα3 antibodies

| Antibody | $IC_{50}$ (nM) |
|---|---|
| M1M6986N | 44 ± 3 (n = 2) |
| M1M6977N | 3 ± 1 (n = 3) |

Examples 13, 14 and 15

The Effect of Anti-Mouse GFRα3 Antibodies in Animal Models of Bone Cancer Pain and Osteoarthritic Pain The antibodies described herein are high affinity human antibodies to the GPI-linked alpha receptor for artemin, GFRα3. Since these antibodies to human GFRα3 do not cross-react with mouse GFRα3, in vivo assays with these antibodies can only be conducted in mice genetically altered to replace the mouse GFRα3 sequence with that of human GFRα3. Initial in vivo experiments in these GFRα3$^{hu/hu}$ mice using pharmacological inhibition of artemin-sensitized capsaicin revealed efficacy of four human antibodies in this in vivo assay. In order to expedite the generation of efficacy data, mouse GFRα3 antibodies were generated to serve as surrogates to the human antibodies. Mice of a mixed C57BL6/129Sv strain that were homozygous for deletion of the endogenous GFRα3 gene were immunized with recombinant mouse GFRα3 extracellular domain expressed in Chinese hamster ovary cells. A specific immune response to GFRα3 was confirmed by immunoassays of serum from the immunized mice. Spleens were collected from mice exhibiting a high specific immune response, and antibody-producing hybridoma cells were generated by fusion of the isolated splenocytes with mouse myeloma cells following standard hybridoma procedures. Hybridoma supernatants were further screened in immunoassays for binding to GFRα3 and for their ability to block binding of GFRα3 to either artemin or artemin/Ret coated on a solid surface in an immunoassay format. Supernatants were also screened for their ability to block artemin stimulation of the GFRα3/Ret co-receptor pathway in a cell-based bioassay. Variable-region antibody sequences were obtained by PCR amplification of selected hybridoma clones whose antibody proteins exhibited potent blocking in the cell-based assay, and these sequences were used to produce full-length recombinant anti-mouse GFRα3 antibodies with a mouse IgG1 isotype. Two antibodies were selected for in vivo testing that potently inhibited artemin signaling in the cell-based assay. In the in vitro binding immunoassay, antibody M1M6986N blocked binding of GFRα3 to both artemin or artemin/Ret coated on a solid surface and is referred to here as a direct blocker. Antibody M1M6977N blocked binding of GFRα3 to coated artemin/Ret but not to artemin alone in the in vitro immunoassay and is referred to here as an indirect blocker. These two mouse antibodies, M1M6986N and M1M6977N, were selected for testing in the artemin-sensitized capsaicin thermal analgesia model (described in Example 6), since these two antibodies demonstrated similar binding and blocking profiles to the efficacious human antibodies. These two antibodies were screened for their ability to block artemin-induced sensitization of hyperalgesia in vivo in wild type mice. Like their human antibody counterparts, both antibodies significantly inhibited artemin's sensitizing effect on capsaicin thermal hyperalgesia three days after capsaicin injection (FIG. 1).

Example 13

Fibrosarcoma Model of Bone Cancer Pain

Figure 2:
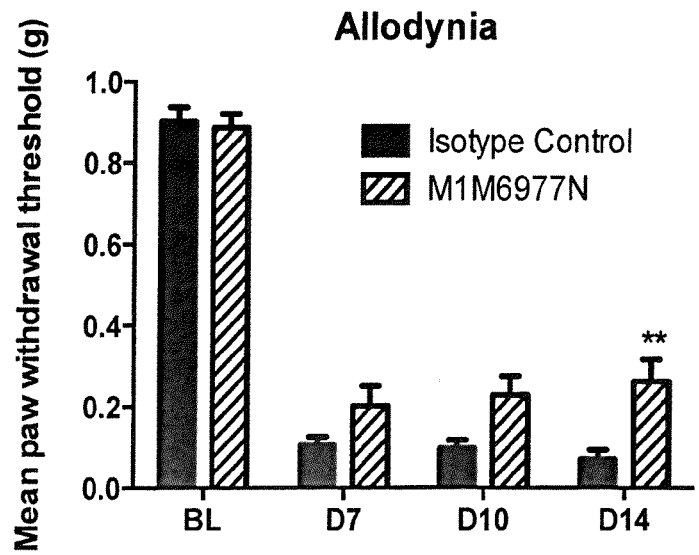
FIGS. 2A and 2B. Tactile allodynia measured by von Frey Hairs in animals from two experiments (A & B) injected with fibrosarcoma and treated with isotype (negative) control antibody (M2M180N) or M1M6977N or M1M6986N anti-mouse GFRα3 antibodies (n=8-11 per group). *$p<0.05$, $p<0.01$, or *$p<0.001$ compared to isotype control at the same time point.
Figure 2:
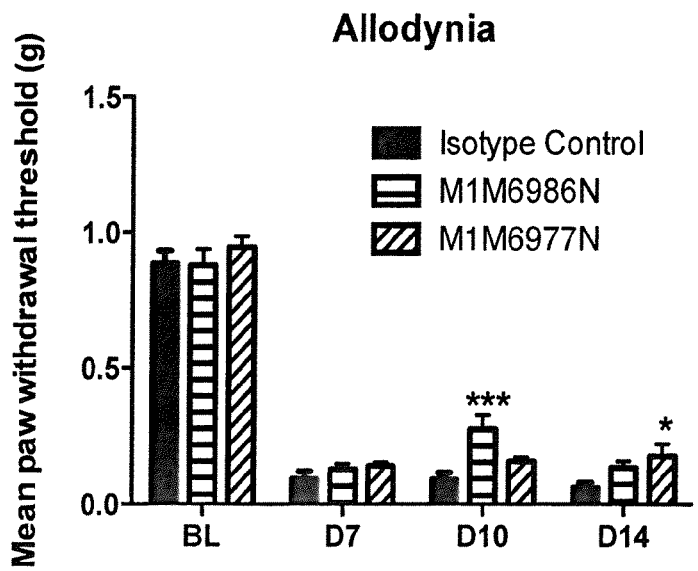
Figure 3:
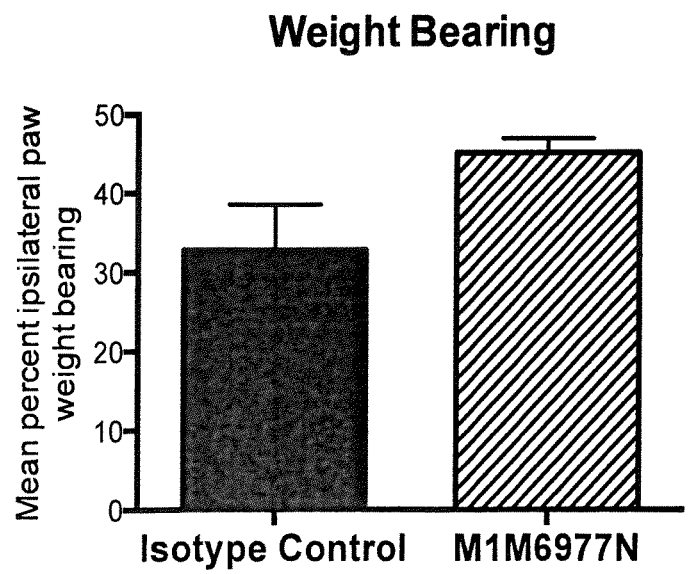
FIGS. 3A and 3B. Percent ipsilateral weight bearing in animals from two experiments (A & B) injected with fibrosarcoma and treated with isotype (negative) control (M2M180N) or M1M6977N or M1M6986N anti-mouse GFRα3 antibodies (n=8-11 per group).
Figure 3:
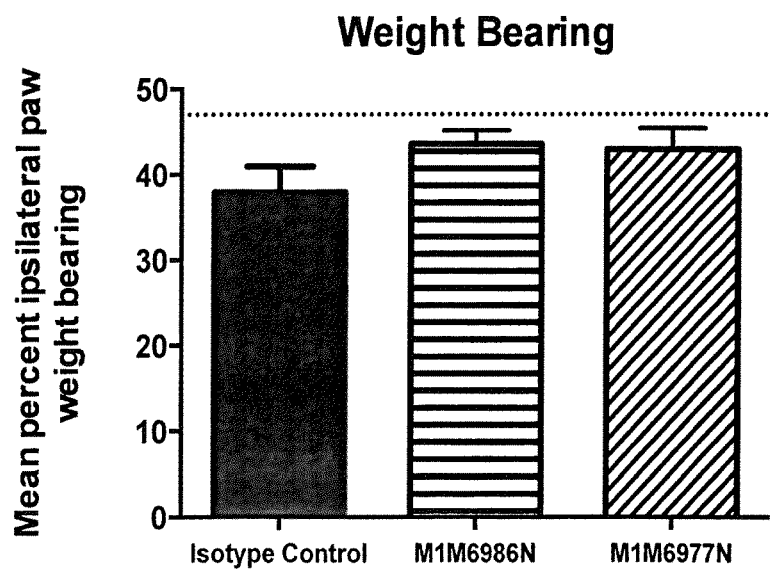
Figure 4:
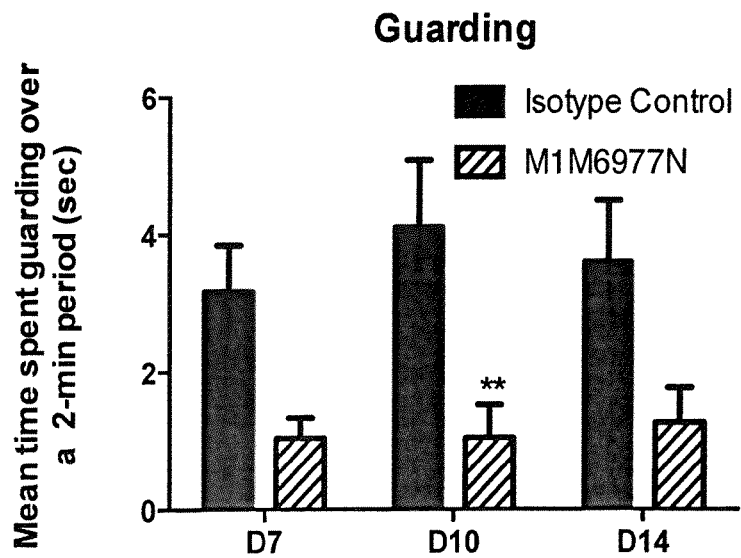
FIGS. 4A and 4B. Guarding scores in animals from two experiments (A & B) injected with fibrosarcoma cells and treated with isotype (negative) control (M2M180N) or M1M6977N or M1M6986N anti-mouse GFRα3 antibodies (n=8-11 per group). **$p<0.01$ compared to isotype control at the same time point.
Figure 4:
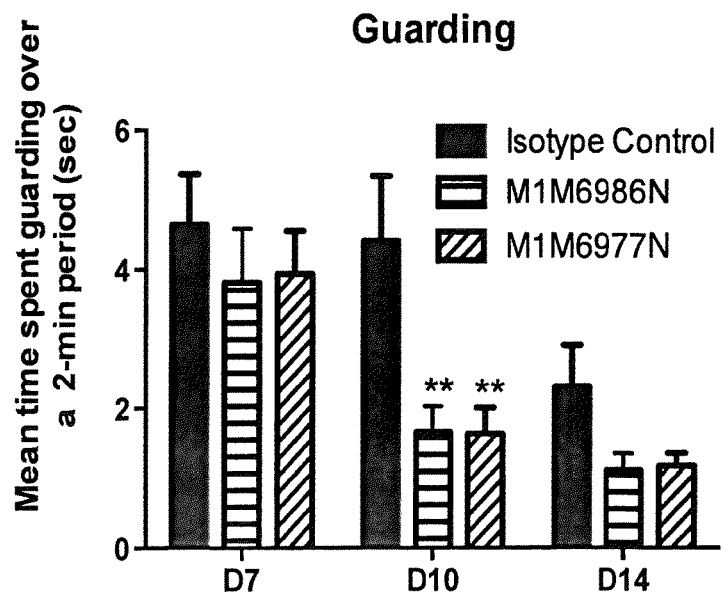

Methodology
Subjects
Adult male mice on a C57Bl6 background strain were used for two fibrosarcoma experiments at approximately 12 weeks of age. The experimenters measuring outcome data for this experiment were blind to treatment group of the animals throughout data collection, compilation, and analysis.
Bone Cancer Model
To induce bone cancer pain, the mice were anesthetized and then injected intrafemorally with $1.0 \times 10^6$ MC57G fibrosarcoma cells. These cells are derived from a C57Bl/6 mouse fibrosarcoma tumor line. Tumors typically grow aggressively in this model, such that bone destruction is evident by 14 days after tumor implantation. Radiographs were taken at days 7, and 10, and 14 after implantation to verify tumor growth and bone destruction. Bone destruction was scored on a three-point scale such that 0 represented no destruction and 3 represented complete destruction of the femur in the region of the tumor.
Antibody Treatment
Each animal received 30 mg/kg s.c. antibody injections administered the day before cancer cell implantation and again on day 7. Animals were pseudo-randomly assigned to one of two or three treatment groups: 1) M2M180N isotype (negative) control antibody in two separate experiments, 2) M1M6977N anti-mouse GFRα3 antibody in two separate experiments or 3) M1M6986N anti-mouse GFRα3 antibody in the second experiment only. M1M6986 blocks artemin's interaction with GFRα3, and is thereby considered a "direct" blocker of artemin's action. In contrast, M1M6977N inhibits artemin's action through the GFRα3/RET complex, and is therefore considered an "indirect" inhibitor.
Measures of Nociception
Nociceptive responses to the bone tumor were measured using the von Frey Hair test for evoked mechanical (tactile) allodynia, the dynamic weight bearing (DWB) test for willingness to bear weight on a limb, and guarding behavior. Von Frey test results are expressed as grams of pressure required for paw withdrawal. Weight bearing results are expressed as percent body weight placed on the ipsilateral limb. Guarding behavior is expressed as time spent guarding the limb over a two-minute period.
Results
Bone Destruction
There was no significant effect of antibody treatment on bone destruction score in either experiment suggesting that the antibody treatment had no impact on the severity of the bone cancer itself (data not shown).
Nociceptive Behavior
There was a statistically significant decrease in tactile allodynia with GFRα3 antibody treatment after fibrosarcoma injection in the first experiment ($F(1,20)=9.189$, $p=0.007$, FIG. 2A) and a statistical trend toward efficacy overall in the second experiment ($F(2,29)=3.069$, $p<0.062$, FIG. 2B), with individual comparisons sometimes achieving significance in the second study (FIG. 2B).
There was no statistically significant effect of GFRα3 antibodies on dynamic weight bearing on the ipsilateral limb measured 14 days after implantation of bone with fibrosarcoma cells in either experiment, although the first experiment revealed a statistical trend toward efficacy with M1M6977N treatment ($t(10)=2.047$, $p=0.068$, FIG. 3A; $F(2,28)=1.598$, $p=0.220$, FIG. 3B).
GFRα3 antibodies significantly reduced limb guarding after bone cancer implantation in both fibrosarcoma experiments ($F(1,20)=12.270$, $p=0.002$, FIG. 4A; $F(2,29)=3.576$, $p=0.041$, FIG. 4B).
Conclusion
Treatment with anti-mouse GFRα3 antibodies significantly reduced nociceptive behaviors in this bone cancer pain model as measured by evaluation of guarding and the von Frey Test of tactile allodynia. In addition, there was a statistical trend toward efficacy of the M1M6977N antibody in weight bearing differential in one experiment. Bone destruction scores were not different in groups receiving anti-mouse GFRα3 antibodies, suggesting that differences in pain-related measures could not be accounted for by differences in cancer severity. Therefore, our data suggest that neutralizing antibodies against GFRα3 could be efficacious against bone cancer pain. Because sarcoma cells are more often primary tumors than metastases in bone, and because most bone cancers derive from metastases of primary tumors from other sites, these antibodies were also tested in a model of breast (mammary) carcinoma-induced bone cancer pain. Breast and prostate tumors are among the most common tumors found to metastasize to bone.

Example 14

Breast Carcinoma Model of Bone Cancer Pain

Methodology
Subjects

Adult male mice on a Balb/c background strain were used for a mammary carcinoma bone cancer experiment at approximately 12 weeks of age. The experimenters measuring outcome data for this experiment were blind to treatment group of the animals throughout data collection, compilation, and analysis.

Bone Cancer Model

To induce bone cancer pain, the mice were anesthetized and then injected intrafemorally with 10,000 4T-1 mammary carcinoma cells. These cells are derived from a Balb/c mammary carcinoma tumor line. Tumors typically grow aggressively in this model, such that tumors are severe by 18 days after implantation. Radiographs were taken at days 10, 14, and 19 after implantation to verify tumor growth and bone destruction. Bone destruction was scored on a three-point scale such that 0 represented no destruction and 3 represented complete destruction of the femur in the region of the tumor.

Antibody Treatment

Each animal received 30 mg/kg s.c. antibody injections administered the day before cancer cell implantation and two times per week thereafter. Animals were pseudo-randomly assigned to one of three treatment groups: 1) M2M180N isotype (negative) control antibody, 2) M1M6977N anti-mouse GFRα3 antibody, or 3) M1M6986N anti-mouse GFRα3 antibody. M1M6986N blocks artemin's interaction with GFRα3, and is thereby considered a "direct" blocker of artemin's action. In contrast, M1M6977N inhibits artemin's action through the GFRα3/RET complex, and is therefore considered an "indirect" inhibitor.

Measures of Nociception

Nociceptive responses to the bone tumor were measured using the von Frey Hair test for evoked mechanical (tactile) allodynia, the dynamic weight bearing (DWB) test for willingness to bear weight on a limb, and guarding behavior. Von Frey test results are expressed as grams of pressure required for paw withdrawal. Weight bearing results are expressed as percent body weight placed on the ipsilateral limb. Guarding behavior is expressed as time spent guarding the limb over a two-minute period.

Results
Bone Destruction

There was no significant effect of antibody treatment on bone destruction score in this model, suggesting that the antibody treatment had no impact on the severity of the bone cancer itself.

Nociceptive Behavior

Figure 5:
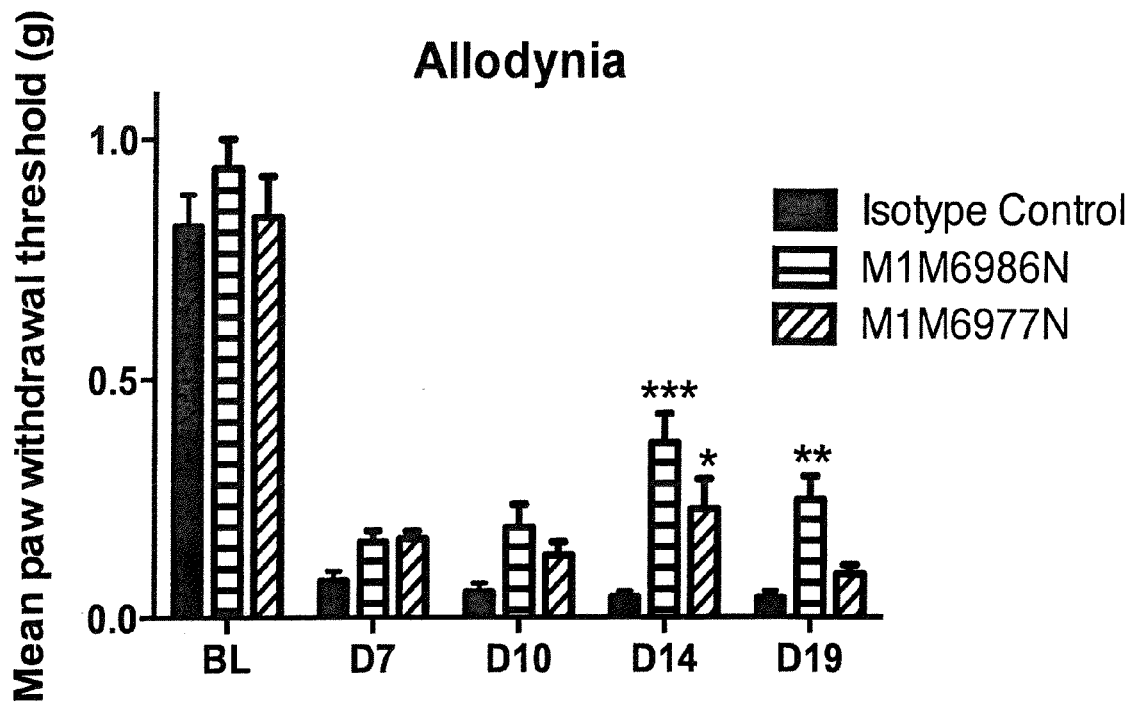
FIG. 5. Tactile allodynia measured by von Frey Hairs in animals injected with carcinoma and treated with isotype (negative) control (M2M180N) or M1M6977N or M1M6986N anti-mouse GFRα3 antibodies (n=9-10 per group). *$p<0.05$, $p<0.01$, or *$p<0.001$ compared to isotype (negative) control at the same time point.

There was a statistically significant decrease in tactile allodynia with GFRα3 antibody treatment after carcinoma ($F(2, 25)=8.626$, $p=0.001$, FIG. 5).

Figure 6:
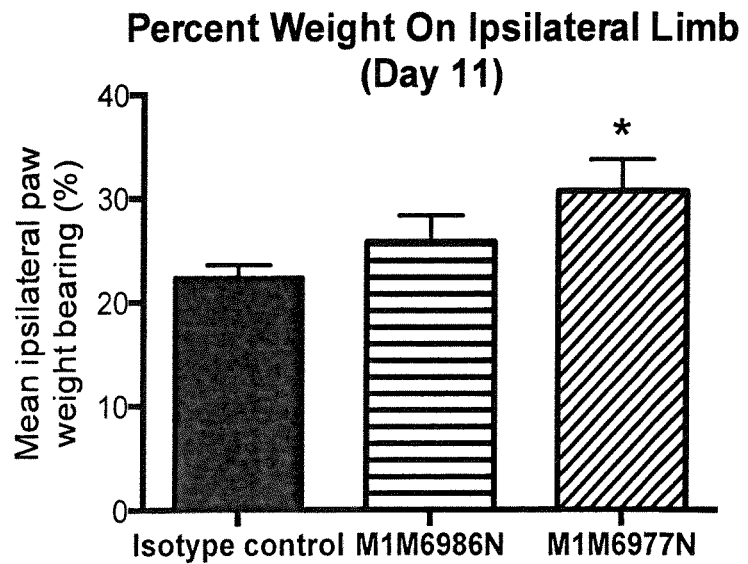
FIGS. 6A and 6B. Percent ipsilateral weight bearing at two time points (A=11 days & B=18 days) injected with carcinoma and treated with isotype (negative) control (M2M180N) or M1M6977N or M1M6986N anti-mouse GFRα3 antibodies (n=9-10 per group). *$p<0.05$ compared to isotype control antibody by post hoc Dunnett's analysis.
Figure 6:
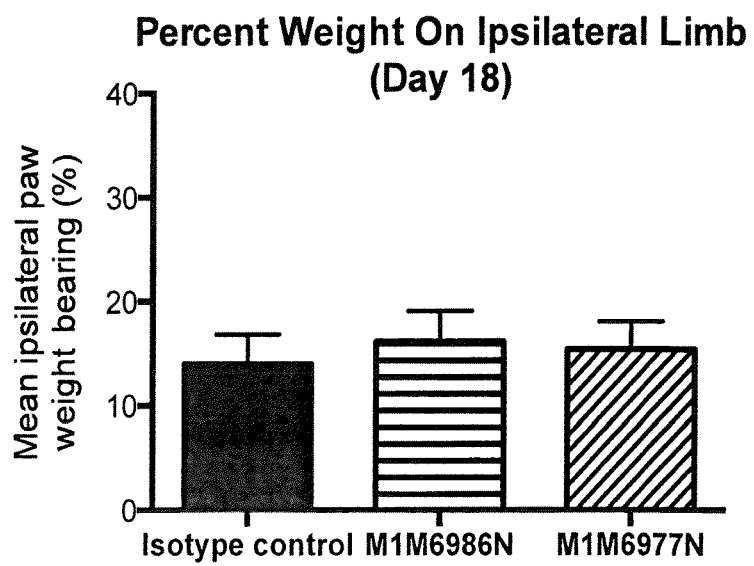

There were no statistically significant overall effects of GFRα3 antibodies on dynamic weight bearing on the ipsilateral limb, although the overall effect of treatment achieved a statistical trend and M1M6977N achieved significant efficacy on post hoc comparison at 11 days (A), but not 18 days (B), after implantation of bone with carcinoma cells (11 day $F(2,25)=2.939$, $p=0.071$, FIG. 6A; 18 day $F(2,25)=0.149$, $p=0.862$, FIG. 6B).

Figure 7:
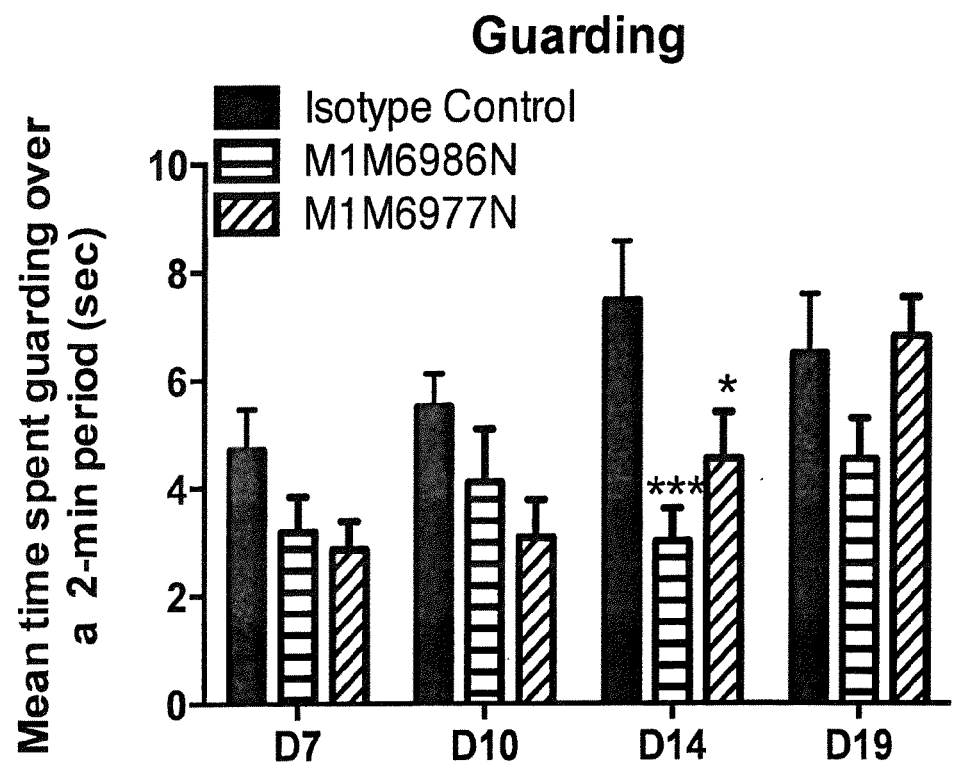
FIG. 7. Guarding scores in animals injected with carcinoma and treated with isotype (negative) control (M2M180N) or M1M6977N or M1M6986N anti-mouse GFRα3 antibodies (n=9-10 per group). *$p<0.05$, ***$p<0.001$ compared to isotype control at the same time point.

GFRα3 antibodies significantly reduced limb guarding after bone cancer implantation in this model ($F(2,25)=4.222$, $p=0.026$, FIG. 7).

Conclusion

Treatment with anti-mouse GFRα3 antibodies significantly reduced nociceptive behaviors in this bone cancer pain model as measured by evaluation of guarding and the von Frey Test of tactile allodynia. In addition, there was evidence of efficacy of the REGN1967 antibody in weight bearing differential at one time point. Bone destruction scores were not different in groups receiving anti-mouse GFRα3 antibodies, suggesting that differences in pain-related measures could not be accounted for by differences in cancer severity. Therefore, our data suggest that neutralizing antibodies against GFRα3 could be efficacious against bone cancer pain in this model of metastatic bone cancer pain.

Example 15

Destabilization of the Medial Meniscus (DMM) Model of Osteoarthritic Pain Methodology Subjects Adult male mice on a C57Bl6 background strain were used for the DMM experiment starting at approximately 12 weeks of age. The experimenters measuring outcome data for this experiment were blind to treatment group of the animals throughout data collection, compilation, and analysis.

DMM Model

In the DMM model, the medial meniscus of one knee is destabilized and the animal is allowed to develop disease for 16 weeks. During the 16 week period, animals develop tactile allodynia and increases in bone volume and bone mineral content in the injured knee resembling early human osteoarthritis. Tactile allodynia was verified in animals by von Frey Test at 16 weeks before the initiation of antibody treatment.

Antibody Treatment

Each animal received 30 mg/kg s.c. antibody injections administered weekly starting 16 weeks after DMM surgery. Animals were pseudo-randomly assigned to one of three treatment groups: 1) M2M180N isotype (negative) control antibody, 2) M1M6977N anti-mouse GFRα3 antibody, or 3) M1M6986N anti-mouse GFRα3 antibody. M1M6986N blocks artemin's interaction with GFRα3, and is thereby considered a "direct" blocker of artemin's action. In contrast, M1M6977N inhibits artemin's action through the GFRα3/RET complex, and is therefore considered an "indirect" inhibitor.

Measures of Nociception

Nociceptive responses to the knee pathology were measured using the von Frey Hair test for evoked mechanical (tactile) allodynia.

Results

Nociceptive Behavior

Figure 8:
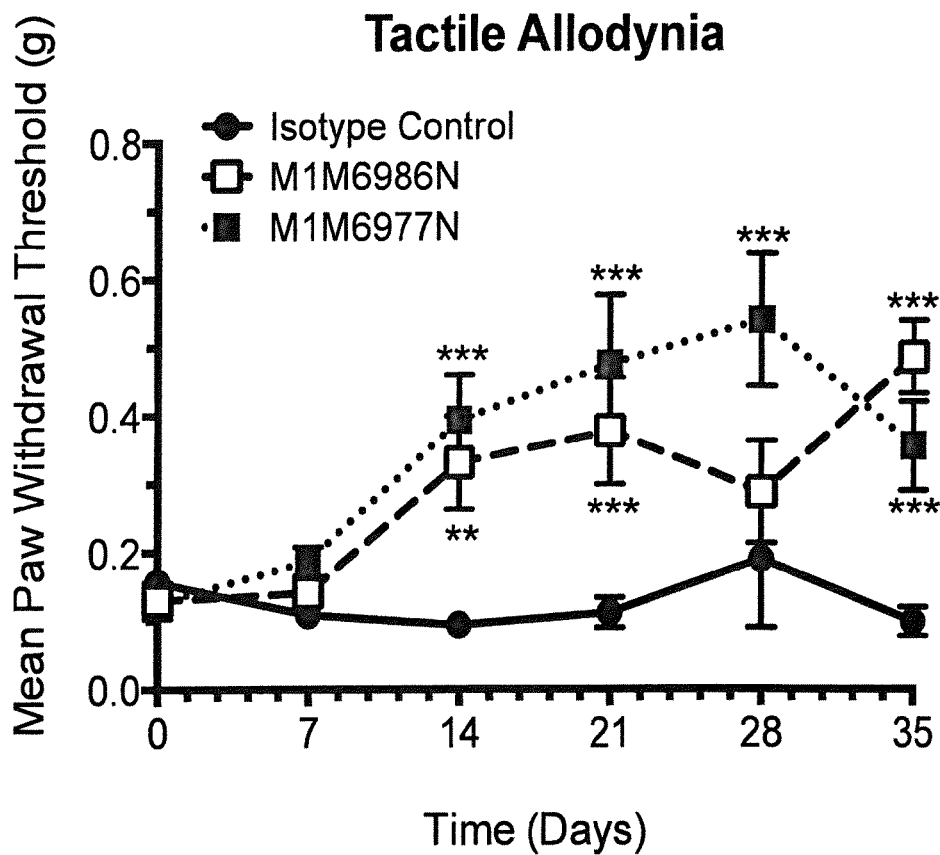
FIG. 8. Tactile allodynia measured by von Frey Hairs in animals with DMM treated with isotype (negative) control (M2M180N) or M1M6977N or M1M6986N anti-mouse GFRα3 antibodies (n=10 per group). $p<0.01$ or *$p<0.001$ compared to isotype control at the same time point.

There was a statistically significant decrease in tactile allodynia with GFRα3 antibody treatment after DMM ($F(2, 27)=21.68$, $p=0.0001$, FIG. 8).

Conclusion

Treatment with mouse GFRα3 antibodies had a statistically significant effect on tactile allodynia such that the groups treated with the two GFRα3 antibodies consistently showed less allodynia than the isotype control starting 14 days after the initiation of weekly treatment. These data suggest the possibility that GFRα3 antibodies will be efficacious against chronic human osteoarthritic pain.

Example 16

Cross-Competition Analysis of Anti-GFRα3 Antibodies

A cross-competition assay was conducted to assess the ability of select antibodies to compete with one another for binding to human GFRα3 using an Octet RED384 biosensor (Fortebio Inc.). The entire experiment was performed at 25° C. with the flow rate of 1000 rpm in Octet HBST buffer (0.01 M HEPES pH7.4, 0.15M NaCl, 3 mM EDTA, 0.05% v/v Surfactant P20, 0.1 mg/mL BSA). To assess whether 2 antibodies were able to compete with one another for binding to their respective epitopes on biotinylated recombinant human GFRα3 expressed with a C-terminal myc-myc-hexahistidine tag (biotin-hGFRα3-mmH; SEQ ID:370), around ~1.2 nm of biotin-hGFRα3-mmH was first captured onto streptavidin-coated Octet sensor tips (Fortebio Inc, #18-5019) by submerging the tips for 1 minute into a 10 µg/mL solution of biotin-hGFRα3-mmH. The antigen coated sensor tips were then placed into wells containing 25 µg/mL solution of a first anti-GFRα3 monoclonal antibody for 4 minutes to saturate the biotin-hGFRα3-mmH surface. The sensor tips were then subsequently dipped into wells containing 25 µg/mL solution of a second anti-GFRα3 monoclonal antibody. The sensor tips were washed in Octet HBST buffer in between every step of the experiment. The real-time binding response was monitored during the course of the experiment and the binding response at the end of every step was recorded as shown in FIG. 9. The response of mAb-2 binding to biotin-hGFRα3-mmH pre-complexed with the first antibody was compared and competitive/non-competitive behavior of different anti-GFRα3 monoclonal antibodies was determined.

As shown in FIG. 9, dark grey boxes with black font represent binding response for self-competition. Antibodies competing in both directions, independent of the order of binding are represented with black boxes and white font. No competition between antibodies that suggest distinct binding epitope is represented as white box with black font.

Nine antibodies (H4H2236N3, H4H2342P, H4H2295S, H4H2294S, H4H2291S, H4H2357S, H4H2355S, H4H2296S, and H4H2243N2) bi-directionally compete with each other for binding to biotin-hGFRα3-mmH. Eight of the 9 (H4H2236N3, H4H2342P, H4H2295S, H4H2294S, H4H2291S, H4H2357S, H4H2355S, and H4H2296S) do not compete with any other anti-GFRα3 antibody tested, while H4H2243N2 also bi-directionally competes with two additional anti-GFRα3 antibodies tested (H4H2212N and H4H2352S). H4H2212N and H4H2352S bi-directionally compete with each other and H4H2243N2 for binding to biotin-hGFRα3-mmH, but while H4H2212N does not compete with any other anti-GFRα3 antibodies tested, H4H2352S also bi-directionally competes with an additional anti-GFRα3 antibody tested (H4H2292S). One anti-GFRα3 antibody tested, H4H2350P, does not compete with any of the anti-GFRα3 antibodies tested for binding to biotin-hGFRα3-mmH.

What is claimed is:

1. A method for treating pain associated with osteoarthritis, the method comprising administering an isolated monoclonal antibody or antigen-binding fragment thereof that specifically binds to glial cell-line derived neurotrophic factor (GDNF) family receptor alpha 3 (GFRα3), or a composition comprising the antibody or antigen-binding fragment thereof, to a patient in need thereof, wherein the antibody comprises: (a) a heavy chain complementarity determining region (HCDR) 1 domain of SEQ ID NO: 148; (b) a HCDR2 domain of SEQ ID NO: 150; (c) a HCDR3 domain of SEQ ID NO: 152; (d) a light chain complementarity determining region (LCDR) 1 domain of SEQ ID NO: 156; (e) a LCDR2 domain of SEQ ID NO: 158; and (f) a LCDR3 domain of SEQ ID NO: 160; wherein the pain associated with the osteoarthritis is prevented from progression, ameliorated, or reduced in severity or frequency of occurrence.

2. The method of claim 1, wherein the antibody or antigen-binding fragment is administered to the patient in combination with a second therapeutic agent, wherein the second therapeutic agent is selected from the group consisting of an opioid, a COX-2 inhibitor, a local anesthetic, a cannabinoid receptor agonist, a VR1 antagonist, a substance P antagonist, a second GFRα3 antagonist, a cytokine or cytokine receptor antagonist, a nerve growth factor (NGF) inhibitor (a small molecular inhibitor or an anti-NGF antibody), an inhibitor of BDNF, TrkA, TrkB or p75, aspirin, a NSAID, a steroid, morphine, a selective serotonin reuptake inhibitor (SSRI), a serotonin norepinephrine reuptake inhibitor (SNRI), a tricyclic, an inhibitor of a voltage-gated sodium channel (Nav), a calcium channel inhibitor, a potassium channel inhibitor, a tumor necrosis factor (TNF) or TNF receptor inhibitor, an inhibitor of TWEAK (TNF-related WEAK inducer of apoptosis), an inhibitor of the receptor tyrosine kinase "rearranged during transfection" (RET), an inhibitor of a GDNF family ligand, an inhibitor of GFRα1, GFRα2 or GFRα4, an inhibitor of an acid sensing ion channel (ASIC1 or ASIC3), an anti-convulsant (gabapentin or pregabalin), an inhibitor of a prekineticin receptor (PROK1 and PROK2), a caspase inhibitor, a p38 inhibitor, an IKK1/2 inhibitor, CTLA-41q and a corticosteroid.

3. The method of claim 2, wherein the second GFRα3 antagonist is a small molecule inhibitor of GFRα3, a second antibody specific for GFRα3, a siRNA or an antisense molecule specific for GFRα3.

4. The method of claim 2, wherein the cytokine or cytokine receptor antagonist is an interleukin-1 (IL-1) antagonist, an IL-6 antagonist, or an IL-18 antagonist.

5. A method for treating pain associated with bone cancer, the method comprising administering an isolated monoclonal antibody or antigen-binding fragment thereof that specifically binds to GFRα3, or a composition comprising the antibody or antigen-binding fragment thereof, to a patient in need thereof, wherein the antibody comprises: (a) a heavy chain complementarity determining region (HCDR) 1 domain of SEQ ID NO: 148; (b) a HCDR2 domain of SEQ ID NO: 150; (c) a HCDR3 domain of SEQ ID NO: 152; (d) a light chain complementarity determining region (LCDR) 1 domain of SEQ ID NO: 156; (e) a LCDR2 domain of SEQ ID NO: 158; and (f) a LCDR3 domain of SEQ ID NO: 160; wherein the pain associated with bone cancer is prevented from progression, ameliorated, or reduced in severity or frequency of occurrence.

6. The method of claim 5, wherein the pain associated with bone cancer is associated with chemotherapy-induced neuropathic pain.

7. The method of claim 5, wherein the antibody or antigen-binding fragment is administered to the patient in combination with a second therapeutic agent, wherein the second therapeutic agent is selected from the group consisting of an opioid, a COX-2 inhibitor, a local anesthetic, a cannabinoid receptor agonist, a VR1 antagonist, a substance P antagonist, a second GFRα3 antagonist, a cytokine or cytokine receptor antagonist, a nerve growth factor (NGF) inhibitor (a small molecular inhibitor or an anti-NGF antibody), an inhibitor of BDNF, TrkA, TrkB or p75, aspirin, a NSAID, a steroid, morphine, a selective serotonin reuptake inhibitor (SSRI), a serotonin norepinephrine reuptake inhibitor (SNRI), a tricyclic, an inhibitor of a voltage-gated sodium channel (Nav), a calcium channel inhibitor, a potassium channel inhibitor, a tumor necrosis factor (TNF) or TNF receptor inhibitor, an inhibitor of TWEAK (TNF-related WEAK inducer of apoptosis), a RET inhibitor, an inhibitor of a GDNF family ligand, an inhibitor of GFRα1, GFRα2 or GFRα4, an inhibitor of an acid sensing ion channel (ASIC1 or ASIC3), an anti-convulsant (gabapentin or pregabalin), an inhibitor of a prekineticin receptor (PROK1 and PROK2), a caspase inhibitor, a p38 inhibitor, an IKK1/2 inhibitor, CTLA-41g and a corticosteroid.

8. The method of claim 7, wherein the second GFRα3 antagonist is a small molecule inhibitor of GFRα3, a second antibody specific for GFRα3, a siRNA or an antisense molecule specific for GFRα3.

9. The method of claim 7, wherein the cytokine or cytokine receptor antagonist is an interleukin-1 (IL-1) antagonist, an IL-6 antagonist, or an IL-18 antagonist.

* * * * *